United States Patent
Arora et al.

(10) Patent No.: US 7,074,809 B2
(45) Date of Patent: Jul. 11, 2006

(54) COMPOUNDS

(75) Inventors: Jalaj Arora, Cambridge (CA); Louise Edwards, Mississauga (CA); Methvin Isaac, Etobicoke (CA); Abdelmalik Slassi, Mississauga (CA); Tomislav Stefanac, Burlington (CA); David Wensbo, Sodertalje (SE); Tao Xin, Woodbridge (CA)

(73) Assignees: AstraZeneca AB, Sodertajle (SE); NPS Pharmaceuticals, Salt Lake City, UT (US)

( * ) Notice: Subject to any disclaimer, the term of this patent is extended or adjusted under 35 U.S.C. 154(b) by 51 days.

(21) Appl. No.: 10/636,977

(22) Filed: Aug. 8, 2003

(65) Prior Publication Data
US 2004/0106607 A1    Jun. 3, 2004

Related U.S. Application Data

(60) Provisional application No. 60/402,038, filed on Aug. 9, 2002.

(51) Int. Cl.
  *A61K 31/44*    (2006.01)
  *C07D 401/00*    (2006.01)
(52) U.S. Cl. .................................. 514/340; 546/268.1
(58) Field of Classification Search ................ 514/340; 546/268.1
  See application file for complete search history.

(56) References Cited

U.S. PATENT DOCUMENTS

| 3,647,809 | A | 3/1972 | Reiter et al. | |
|---|---|---|---|---|
| 3,740,434 | A | 6/1973 | Berkelhammer et al. | |
| 4,022,901 | A | 5/1977 | Narayanan et al. | |
| 4,476,128 | A | 10/1984 | Sakani et al. | |
| 5,631,269 | A | 5/1997 | Broughton et al. | |
| 6,770,661 | B1* | 8/2004 | Shao et al. | 514/336 |
| 6,800,647 | B1* | 10/2004 | Crocker et al. | 514/334 |
| 6,821,994 | B1* | 11/2004 | Tajima et al. | 514/340 |
| 6,864,268 | B1* | 3/2005 | Lafontaine et al. | 514/340 |
| 6,867,225 | B1* | 3/2005 | Dumaitre et al. | 514/365 |
| 6,875,779 | B1* | 4/2005 | Sakya et al. | 514/340 |

FOREIGN PATENT DOCUMENTS

| EP | 0 377 457 A1 | 7/1990 |
|---|---|---|
| EP | 0438 230 A2 | 7/1991 |
| WO | WO 00/35285 | 6/2000 |
| WO | WO 00/63204 | 10/2000 |
| WO | WO 01/12627 A1 | 2/2001 |
| WO | WO 01/26656 A2 | 4/2001 |
| WO | WO 02/24680 A1 | 3/2002 |
| WO | WO 02/36116 A2 | 5/2002 |
| WO | WO 02/46166 A1 | 6/2002 |
| WO | WO 03/002559 A2 | 1/2003 |
| WO | WO 03/008411 | 1/2003 |

OTHER PUBLICATIONS

International Search Report.
Huang, Y. et al., "Synthesis of 2- (2,3-dimethoxyphenyl) -4- (aminomethyl) imidazole analogues and their binding . . . ," Bioorganic & Medicinal Chemistry, 9 (2001), pp. 3313-3122.

* cited by examiner

*Primary Examiner*—Deborah C. Lambkin
(74) *Attorney, Agent, or Firm*—Birch, Stewart, Kolasch & Birch, LLP

(57) ABSTRACT

The present invention relates to new compounds of formula I,

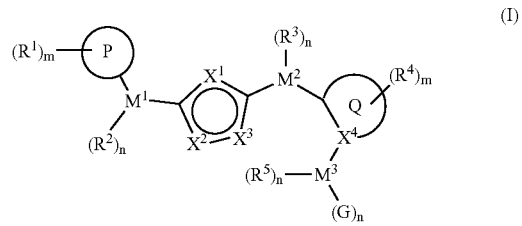

wherein P, Q, $X^1$, $X^2$, $X^3$, $X^4$, $X^5$, R, $R^1$, $R^2$, $R^3$, $R^4$, $R^5$, G, $M^1$, $M^2$, $M^3$, m and n, are defined as in formula I, a process for their preparation and new intermediates prepared therein, pharmaceutical formulations containing said compounds and to the use of said compounds in therapy.

12 Claims, No Drawings

COMPOUNDS

FIELD OF THE INVENTION

The present invention relates to a new class of compounds, to pharmaceutical formulations containing said compounds and to the use of said compounds in therapy. The present invention further relates to the process for the preparation of said compounds and to new intermediates prepared therein.

BACKGROUND OF THE INVENTION

Glutamate is the major excitatory neurotransmitter in the mammalian central nervous system (CNS). Glutamate produces its effects on central neurons by binding to and thereby activating cell surface receptors. These receptors have been divided into two major classes, the ionotropic and metabotropic glutamate receptors, based on the structural features of the receptor proteins, the means by which the receptors transduce signals into the cell, and pharmacological profiles.

The metabotropic glutamate receptors (mGluRs) are G protein-coupled receptors that activate a variety of intracellular second messenger systems following the binding of glutamate. Activation of mGluRs in intact mammalian neurons elicits one or more of the following responses: activation of phospholipase C; increases in phosphoinositide (PI) hydrolysis; intracellular calcium release; activation of phospholipase D; activation or inhibition of adenyl cyclase; increases or decreases in the formation of cyclic adenosine monophosphate (cAMP); activation of guanylyl cyclase; increases in the formation of cyclic guanosine monophosphate (cGMP); activation of phospholipase $A_2$; increases in arachidonic acid release; and increases or decreases in the activity of voltage- and ligand-gated ion channels. Schoepp et al., *Trends Pharmacol. Sci.* 14:13 (1993), Schoepp, *Neurochem. Int.* 24:439 (1994), Pin et al., *Neuropharmacology* 34:1 (1995), Bordi and Ugolini, *Prog. Neurobiol.* 59:55 (1999).

Eight distinct mGluR subtypes, termed mGluR1 through mGluR8, have been identified by molecular cloning. Nakanishi, *Neuron* 13:1031 (1994), Pin et al., *Neuropharmacology* 34:1 (1995), Knopfel et al., *J. Med. Chem.* 38:1417 (1995). Further receptor diversity occurs via expression of alternatively spliced forms of certain mGluR subtypes. Pin et al., *PNAS* 89:10331 (1992), Minakami et al., *BBRC* 199:1136 (1994), Joly et al., *J. Neurosci.* 15:3970 (1995).

Metabotropic glutamate receptor subtypes may be subdivided into three groups, Group I, Group II, and Group III mGluRs, based on amino acid sequence homology, the second messenger systems utilized by the receptors, and by their pharmacological characteristics. Group I mGluR comprises mGluR1, mGluR5 and their alternatively spliced variants. The binding of agonists to these receptors results in the activation of phospholipase C and the subsequent mobilization of intracellular calcium.

Attempts at elucidating the physiological roles of Group I mGluRs suggest that activation of these receptors elicits neuronal excitation. Various studies have demonstrated that Group I mGluRs agonists can produce postsynaptic excitation upon application to neurons in the hippocampus, cerebral cortex, cerebellum, and thalamus, as well as other CNS regions. Evidence indicates that this excitation is due to direct activation of postsynaptic mGluRs, but it also has been suggested that activation of presynaptic mGluRs occurs, resulting in increased neurotransmitter release. Baskys, *Trends Pharmacol. Sci.* 15:92 (1992), Schoepp, *Neurochem. Int.* 24:439 (1994), Pin et al., *Neuropharmacology* 34:1(1995), Watkins et al., *Trends Pharmacol. Sci.* 15:33 (1994).

Metabotropic glutamate receptors have been implicated in a number of normal processes in the mammalian CNS. Activation of mGluRs has been shown to be required for induction of hippocampal long-term potentiation and cerebellar long-term depression. Bashir et al., *Nature* 363:347 (1993), Bortolotto et al., *Nature* 368:740 (1994), Aiba et al., *Cell* 79:365 (1994), Aiba et al., *Cell* 79:377 (1994). A role for mGluR activation in nociception and analgesia also has been demonstrated. Meller et al., *Neuroreport* 4: 879 (1993), Bordi and Ugolini, *Brain Res.* 871:223 (1999). In addition, mGluR activation has been suggested to play a modulatory role in a variety of other normal processes including synaptic transmission, neuronal development, apoptotic neuronal death, synaptic plasticity, spatial learning, olfactory memory, central control of cardiac activity, waking, motor control and control of the vestibulo-ocular reflex. Nakanishi, *Neuron* 13: 1031 (1994), Pin et al., *Neuropharmacology* 34:1, Knopfel et al., *J. Med. Chem.* 38:1417 (1995).

Further, Group I metabotropic glutamate receptors and mGluR5 in particular, have been suggested to play roles in a variety of pathophysiological processes and disorders affecting the CNS. These include stroke, head trauma, anoxic and ischemic injuries, hypoglycemia, epilepsy, neurodegenerative disorders such as Alzheimer's disease and pain. Schoepp et al., *Trends Pharmacol. Sci.* 14:13 (1993), Cunningham et al., *Life Sci.* 54:135 (1994), Hollman et al., *Ann. Rev. Neurosci.* 17:31 (1994), Pin et al., *Neuropharmacology* 34:1 (1995), Knopfel et al., *J. Med. Chem.* 38:1417 (1995), Spooren et al., *Trends Pharmacol. Sci.* 22:331 (2001), Gasparini et al. *Curr. Opin. Pharmacol.* 2:43 (2002), Neugebauer *Pain* 98:1 (2002). Much of the pathology in these conditions is thought to be due to excessive glutamate-induced excitation of CNS neurons. Because Group I mGluRs appear to increase glutamate-mediated neuronal excitation via postsynaptic mechanisms and enhanced presynaptic glutamate release, their activation probably contributes to the pathology. Accordingly, selective antagonists of Group I mGluR receptors could be therapeutically beneficial, specifically as neuroprotective agents, analgesics or anticonvulsants.

Recent advances in the elucidation of the neurophysiological roles of metabotropic glutamate receptors generally and Group I in particular, have established these receptors as promising drug targets in the therapy of acute and chronic neurological and psychiatric disorders and chronic and acute pain disorders. Because of their physiological and pathophysiological significance, there is a need for new potent mGluR agonists and antagonists that display a high selectivity for mGluR subtypes, particularly the Group I receptor subtype, most particularly the mGluR5 subtype.

The object of the present invention is to provide compounds exhibiting an activity at metabotropic glutamate receptors (mGluRs), especially at the mGluR5 receptor.

SUMMARY OF THE INVENTION

Accordingly, the present invention provides a compound of formula I

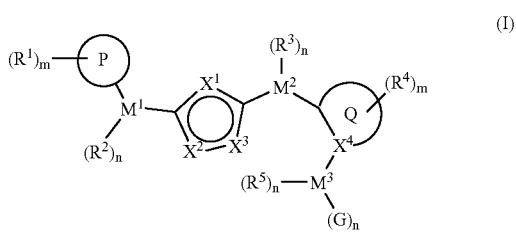

(I)

wherein:

P is selected from the group consisting of $C_{3-7}$alkyl and a 3- to 8-membered ring containing one or more atoms independently selected from C, N, O or S, wherein said ring may be fused with a 5- or 6-membered ring containing one or more atoms independently selected from C, N, O or S;

$R^1$ is selected from the group consisting of hydrogen, hydroxy, halo, nitro, $C_{1-6}$alkylhalo, $OC_{1-6}$alkylhalo, $C_{1-6}$alkyl, $OC_{1-6}$alkyl, $C_{2-6}$alkenyl, $OC_{2-6}$alkenyl, $C_{2-6}$alkynyl, $OC_{2-6}$alkynyl, $C_{0-6}$alkyl$C_{3-6}$cycloalkyl, $OC_{0-6}$alkyl$C_{3-6}$cycloalkyl, $C_{0-6}$alkylaryl, $OC_{0-6}$alkylaryl, (CO)$R^8$, O(CO)$R^8$, O(CO)O$R^8$, $C_{1-6}$alkylO$R^8$, $OC_{2-6}$alkylO$R^8$, $C_{1-6}$alkyl(CO)$R^8$, $OC_{1-6}$alkyl(CO)$R^8$, $C_{0-6}$alkylCO$_2R^8$, $OC_{1-6}$alkylCO$_2R^8$, $C_{0-6}$alkylcyano, $OC_{2-6}$alkylcyano, $C_{0-6}$alkylNR$^8R^9$, $OC_{2-6}$alkylNR$^8R^9$, $C_{1-6}$alkyl(CO)NR$^8R^9$, $OC_{1-6}$alkyl(CO)NR$^8R^9$, $C_{0-6}$alkylNR$^8$(CO)$R^9$, $OC_{2-6}$alkylNR$^8$(CO)$R^9$, $C_{0-6}$alkylNR$^8$(CO)NR$^8R^9$, $C_{0-6}$alkylSR$^8$, $OC_{2-6}$alkylSR$^8$, $C_{0-6}$alkyl(SO)$R^8$, $OC_{2-6}$alkyl(SO)$R^8$, $C_{0-6}$alkylSO$_2R^8$, $OC_{2-6}$alkylSO$_2R^8$, $C_{0-6}$alkyl(SO$_2$)NR$^8R^9$, $OC_{2-6}$alkyl(SO$_2$)NR$^8R^9$, $C_{0-6}$alkylNR$^8$(SO$_2$)$R^9$, $OC_{2-6}$alkylNR$^8$(SO$_2$)$R^9$, $C_{0-6}$alkylNR$^8$(SO$_2$)NR$^8R^9$, $OC_{2-6}$alkylNR$^8$(SO$_2$)NR$^8R^9$, (CO)NR$^8R^9$, O(CO)NR$^8R^9$, NR$^8$OR$^9$, $C_{0-6}$alkylNR$^8$(CO)OR$^9$, $OC_{0-6}$alkylNR$^8$(CO)OR$^9$, SO$_3R^8$ and a 5- or 6-membered ring containing one or more atoms independently selected from C, N, O or S, wherein said ring may be substituted by one or more A;

$M^1$ is selected from the group consisting of a bond, $C_{1-3}$alkyl, $C_{2-3}$alkenyl, $C_{2-3}$alkynyl, $C_{0-4}$alkyl(CO)$C_{0-4}$alkyl, $C_{0-3}$alkylOC$_{0-3}$alkyl, $C_{0-3}$alkyl(CO)NR$^8$, $C_{0-3}$alkyl(CO)NR$^8$C$_{1-3}$alkyl, $C_{0-4}$alkylNR$^8R^9$, $C_{0-3}$alkylSC$_{0-3}$alkyl, $C_{0-3}$alkyl(SO)$C_{0-3}$alkyl and $C_{0-3}$alkyl(SO$_2$)$C_{0-3}$alkyl; $R^2$ is selected from the group consisting of hydrogen, hydroxy, oxo, =NR$^8$, =NOR$^8$, $C_{1-4}$alkylhalo, halo, $C_{1-4}$alkyl, O(CO)$C_{1-4}$alkyl, $C_{1-4}$alkyl(SO)$C_{0-4}$alkyl, $C_{1-4}$alkyl(SO$_2$)$C_{0-4}$alkyl, (SO)$C_{0-4}$alkyl, (SO$_2$)$C_{0-4}$alkyl, OC$_{1-4}$alkyl, $C_{0-4}$alkylcyano, $C_{1-4}$alkylOR$^8$ and $C_{0-4}$alkylNR$^8R^9$;

$X^1$, $x^2$ and $X^3$ are independently selected from N, NR, O, CR, =O and S;

R is selected from the group consisting of hydrogen, $C_{0-3}$alkyl, halo, $C_{0-3}$alkylOR$^5$, $C_{0-3}$alkylNR$^5R^6$, $C_{0-3}$alkyl(CO)OR$^5$, $C_{0-3}$alkylNR$^5R^6$ and $C_{0-3}$alkylaryl;

$M^2$ is selected from the group consisting of a bond, $C_{1-3}$alkyl, $C_{2-3}$alkenyl, $C_{2-3}$alkynyl, $C_{0-4}$alkyl(CO)$C_{0-4}$alkyl, $C_{0-3}$alkylOC$_{0-3}$alkyl, $C_{0-3}$alkylNR$^8$C$_{1-3}$alkyl, $C_{0-3}$alkyl(CO)NR$^8$, $C_{0-4}$alkylNR$^8R^9$, $C_{0-3}$alkylSC$_{0-3}$alkyl, $C_{0-3}$alkyl(SO)$C_{0-3}$alkyl and $C_{0-3}$alkyl(SO$_2$)$C_{0-3}$alkyl;

$R^3$ is selected from the group consisting of hydrogen, hydroxy, oxo, =NR$^8$, =NOR$^8$, $C_{1-4}$alkylhalo, halo, $C_{1-4}$alkyl, O(CO)$C_{1-4}$alkyl, $C_{1-4}$alkyl(SO)$C_{0-4}$alkyl, $C_{1-4}$alkyl(SO$_2$)$C_{0-4}$alkyl, (SO)$C_{0-4}$alkyl, (SO$_2$)$C_{0-4}$alkyl, OC$_{1-4}$alkyl, $C_{0-4}$alkylcyano, $C_{1-4}$alkylOR$^8$ and $C_{0-4}$alkylNR$^8R^9$;

Q is a 4-, 5-, 6- or 7-membered ring containing one or more heteroatoms independently selected from N, O or S, wherein said ring may be fused with a 3-, 5- or 6-membered ring containing one or more atoms independently selected from C, N, O or S, and wherein the fused ring may be substituted by one or more A;

$X_4$ is selected from the group consisting of C, CR and N;

$R^4$ is selected from the group consisting of hydrogen, hydroxy, oxo, =NR$^8$, =NOR$^8$, $C_{1-4}$alkylhalo, halo, $C_{1-4}$alkyl, $OC_{0-6}$alkylaryl, O(CO)$C_{1-4}$alkyl, $C_{1-4}$alkyl(SO)$C_{0-4}$alkyl, $C_{1-4}$alkyl(SO$_2$)$C_{0-4}$alkyl, (SO)$C_{0-4}$alkyl, (SO$_2$)$C_{0-4}$alkyl, OC$_{1-4}$alkyl, $C_{1-4}$alkylOR$^8$, $C_{0-4}$alkylcyano and $C_{0-4}$alkylNR$^8R^9$;

$M_3$ is selected from the group consisting of a bond, $C_{1-4}$alkyl, $C_{0-4}$alkyl(CO)$C_{0-4}$alkyl, $C_{0-3}$alkylOC$_{0-3}$alkyl, $C_{0-4}$alkylNR$^8R^9$, $C_{0-3}$alkylNR$^8$C$_{1-3}$alkyl, $C_{0-3}$alkyl(CO)NR$^8$, $C_{0-3}$alkylSC$_{0-3}$alkyl, $C_{0-3}$alkyl(SO)$C_{0-3}$alkyl and $C_{0-3}$alkyl(SO$_2$)$C_{0-3}$alkyl;

$R^5$ is selected from the group consisting of hydrogen, hydroxy, oxo, =NR$^8$, =NOR$^8$, $C_{1-4}$alkylhalo, halo, $C_{1-4}$alkyl, O(CO)$C_{1-4}$alkyl, $C_{1-4}$alkyl(SO)$C_{1-4}$alkyl, $C_{1-4}$alkyl(SO$_2$)$C_{0-4}$alkyl, (SO)$C_{0-4}$alkyl, (SO$_2$)$C_{0-4}$alkyl, OC$_{1-4}$alkyl, $C_{0-4}$alkylcyano, $C_{1-4}$alkylOR$^8$ and $C_{0-4}$alkylNR$^8R^9$;

G is selected from the group consisting of $R^6$ and $R^7$;

$R^6$ is selected from the group consisting of hydrogen and a 5- or 6-membered ring containing one or more atoms independently selected from C, N, O or S, wherein said ring may be fused with a 5- or 6-membered ring containing one or more atoms independently selected from C, N, O or S, and wherein any of the rings may be substituted by one or more A;

$R^7$ is selected from the group consisting of hydrogen, $C_{0-4}$alkylcyano, C=NR$^8$(NR$^8R^9$), C=NOR$^8$(NR$^8R^9$), NR$^8$C=NR$^8$(NR$^8R^9$), NR$^8$(C=CCN)(NR$^8R^9$), NR$^8$(C=CNO$_2$)(NR$^8R^9$), NR$^8$(C=NCN)(NR$^8R^9$), CONR$^9$ and NR$^8$(CO)NR$^8R^9$;

$R^8$ and $R^9$ are independently selected from hydrogen, $C_{1-6}$alkyl, $C_{0-6}$alkyl$C_{3-6}$cycloalkyl, $C_{0-6}$alkylaryl, $C_{0-6}$alkylheteroaryl and a 5- or 6-membered ring containing one or more atoms independently selected from C, N, O or S, and wherein $R^8$ and $R^9$ may together form a 5- or 6-membered ring containing one or more atoms independently selected from C, N, O or S;

wherein any $C_{1-6}$alkyl, $C_{2-6}$alkenyl, $C_{2-6}$alkynyl, $C_{0-6}$alkyl$C_{3-6}$cycloalkyl, $C_{0-6}$alkylaryl, $C_{0-6}$alkylheteroary and 5- or 6-membered ring containing one or more atoms independently selected from C, N, O or S as defined under $R^1$, $R^2$, $R^3$, $R^4$, $R^5$, $R^6$, $R^7$, $R^8$, and $R^9$, may be substituted by one or more A;

A is selected from the group consisting of hydrogen, hydroxy, oxo, halo, nitro, $C_{1-6}$alkyl, $C_{0-6}$alkyl$C_{3-6}$cycloalkyl, $C_{1-6}$alkylhalo, $OC_{1-6}$alkylhalo, $C_{2-6}$alkenyl, $OC_{1-6}$alkyl, $C_{0-3}$alkylaryl, $C_{1-6}$alkylOR$^8$, $OC_{2-6}$alkylOR$^8$, $C_{1-6}$alkylSR$^8$, $OC_{2-6}$alkylSR$^8$, (CO)$R^8$, O(CO)$R^8$, $OC_{2-6}$alkylcyano, $C_{0-6}$alkylcyano, $C_{0-6}$alkylC$_2R^8$, $OC_{1-6}$alkylCO$_2R^8$, O(CO)OR$^8$OC$_{1-6}$alkyl(CO)$R^8$, $C_{1-6}$alkyl(CO)$R^8$, NR$^8$OR$^9$, $C_{0-6}$alkylNR$^8R^9$, $OC_{2-6}$alkylNR$^8R^9$, $C_{0-6}$alkyl(CO)NR$^8R^9$, $OC_{1-6}$alkyl(CO)NR$^8R^9$, $OC^{2-6}$alkylNR$^8$(CO)$R^9$, $C_{0-6}$alkylNR$^8R^9$, $C_{0-6}$alkylNR$^8$(CO)NR$^8R^9$, O(CO)NR$^8R^9$, NR$^8$(CO)OR$^9$, $C_{0-6}$alkyl(SO$_2$)NR$^8R^9$, $OC_{2-6}$alkyl(SO$_2$)NR$^8R^9$, $C_{0-6}$alkylNR$^8$(SO$_2$)$R^9$, $OC_{2-6}$alkylNR$^8$(SO$_2$)$R^9$, SO$_3R^8$, C$_{1-6}$alkylNR$^8$(SO$_2$)NR$^8$R$^9$, OC$_{2-6}$alkyl(SO$_2$)R$^8$, C$_{0-6}$alkyl(SO$_2$)R$^8$, C$_{0-6}$alkyl(SO)R$^8$ and OC$_{2-6}$alkyl(SO)R$^8$;

m is selected from 0, 1, 2, 3 or 4; and n is selected from 0, 1, 2 or 3;

or salt thereof.

In a further aspect of the invention there is provided pharmaceutical formulations comprising a therapeuticaly effective amount of a compound of formula I and a pharmaceutically acceptable diluent, excipients and/or inert carrier.

In yet a further aspect of the invention there is provided a pharmaceutical formulation including a compound of formula I for the treatment of mGluR5 receptor-mediated disorders, and particularly neurological disorders, psychiatric disorders, acute and chronic pain.

In still a further aspect of the invention there is provided a compound of formula I for use in therapy for the treatment of mGluR5 receptor-mediated disorders, and particularly neurological disorders, psychiatric disorders, acute and chronic pain.

In another aspect of the invention there is provided a process for the preparation of compound of formula I, and the intermediates provided therein.

These and other aspects of the present invention are described in greater detail herein below.

DETAILED DESCRIPTION OF THE INVENTION

Listed below are definitions of various terms used in the specification and claims to describe the present invention.

For the avoidance of doubt it is to be understood that where in this specification a group is qualified by 'hereinbefore defined', 'defined hereinbefore' or 'defined above' the said group encompasses the first occurring and broadest definition as well as each and all of the other definitions for that group.

For the avoidance of doubt it is to be understood that in this specification 'C$_{1-6}$' means a carbon group having 1, 2, 3, 4, 5 or 6 carbon atoms.

In this specification, unless stated otherwise, the term "alkyl" includes both straight and branched chain alkyl groups and may be methyl, ethyl, n-propyl, i-propyl, n-butyl, i-butyl, s-butyl, t-butyl, n-pentyl, i-pentyl, t-pentyl, neo-pentyl, n-hexyl or i-hexyl, t-hexyl. The term "C$_{1-3}$alkyl" refers to an alkyl group having 1 to 3 carbon atoms, and may be methyl, ethyl, n-propyl or i-propyl.

In this specification, unless stated otherwise, the term "cycloalkyl" refers to an optionally substituted, saturated cyclic hydrocarbon ring system. The term "C$_{3-7}$cycloalkyl" may be cyclopropyl, cyclobutyl, cyclopentyl, cyclohexyl or cycloheptyl.

In this specification, unless stated otherwise, the term "alkenyl" includes both straight and branched chain alkenyl groups. The term "C$_{2-6}$alkenyl" refers to an alkenyl group having 2 to 6 carbon atoms and one or two double bonds, and may be, but is not limited to vinyl, allyl, propenyl, i-propenyl, butenyl, i-butenyl, crotyl, pentenyl, i-pentenyl or hexenyl.

In this specification, unless stated otherwise, the term "alkynyl" includes both straight and branched chain alkynyl groups. The term "C$_{2-6}$alkynyl" refers to a group having 2 to 6 carbon atoms and one or two triple bonds, and may be, but is not limited to ethynyl, propargyl, butynyl, i-butynyl, pentynyl, i-pentynyl or hexynyl.

The term "aryl" refers to an optionally substituted monocyclic or bicyclic hydrocarbon ring system containing at least one unsaturated aromatic ring. Examples and suitable values of the term "aryl" are phenyl, naphthyl, 1,2,3,4-tetrahydronaphthyl, indyl and indenyl.

In this specification, unless stated otherwise, the term "heteroaryl" refers to an optionally substituted, unsaturated cyclic hydrocarbon ring system comprising at least one heteroatom and includes, but is not limited to furyl, isoxazolyl, isothiazolyl, oxazolyl, thiazolyl, pyrazinyl, pyridazinyl, pyridyl, pyrimidyl, pyrrolyl, thiazolyl, imidazolyl, imidazolinyl, pyrazolinyl, tetrahydropyranyl.

In this specification, unless stated otherwise, the term "5- or 6-membered ring containing one or more atoms independently selected from C, N, O or S" includes aromatic and heteroaromatic rings as well as carbocyclic and heterocyclic rings which may be saturated or unsaturated. Examples of such rings may be, but are not limited to furyl, isoxazolyl, isothiazolyl, oxazolyl, pyrazinyl, pyrazolyl, pyridazinyl, pyridyl, pyrimidyl, pyrrolyl, thiazolyl, thienyl, imidazolyl, imidazolidinyl, imidazolinyl, triazolyl, morpholinyl, piperazinyl, piperidyl, piperidonyl, pyrazolidinyl, pyrazolinyl, pyrrolidinyl, pyrrolinyl, tetrahydropyranyl, thiomorpholinyl, phenyl, cyclohexyl, cyclopentyl or cyclohexenyl.

In this specification, unless stated otherwise, the terms "3- to 8-membered ring containing one or more atoms independently selected from C, N, O or S" includes aromatic and heteroaromatic rings as well as carbocyclic and heterocyclic rings which may be saturated or unsaturated. Examples of such rings may be, but are not limited to imidazolidinyl, imidazolinyl, morpholinyl, piperazinyl, piperidyl, piperidonyl, pyrazolidinyl, pyrazolinyl, pyrrolidinyl, pyrrolinyl, tetrahydropyranyl or thiomorpholinyl, tetrahydrothiopyranyl, furyl, pyrrolyl, isoxazolyl, isothiazolyl, oxazolyl, oxazolidinonyl, pyrazinyl, pyrazolyl, pyridazinyl, pyridyl, pyrimidyl, pyrrolyl, thiazolyl, thienyl, imidazolyl, triazolyl, phenyl, cyclopropyl, aziridinyl, cyclobutyl, azetidinyl, cyclopentyl, cyclopentenyl, cyclohexyl, cyclohexenyl, cycloheptyl, cycloheptenyl, cyclooctyl, cyclooctenyl.

In this specification, unless stated otherwise, the term "3- to 8-membered ring containing one or more atoms independently selected from C, N, O or S, which group may optionally be fused with a 5- or 6-membered ring containing one or more atoms independently selected from C, N, O or S" includes aromatic and heteroaromatic rings as well as carbocyclic and heterocyclic rings which may be saturated or unsaturated. Examples of such rings may be, but are not limited to naphthyl, norcaryl, chromyl, isochromyl, indanyl, benzoimidazol or tetralinyl, benzooxazolyl, benzothiazolyl, benzofuryl, benzothienyl, benzotriazolyl, indolyl, azaindolyl, indazolyl, indolinyl, isoindolinyl, benzimidazolyl, oxadiazolyl, thiadiazolyl, quinolinyl, quinoxalinyl, benzotriazolyl.

In this specification, unless stated otherwise, the term "4-, 5-, 6- or 7-membered ring containing one or more heteroatoms independently selected from N, O or S, wherein said ring may be fused with a 3-, 5- or 6-membered ring containing one or more atoms independently selected from C, N, O or S" includes aromatic and heteroaromatic rings as well as carbocyclic and heterocyclic rings which may be saturated or unsaturated. Examples of such rings may be, but are not limited to pyridinyl, thiazolyl, benzoimidazolyl, quinolinyl, imidazolyl, oxadiazolyl, benzothiazolyl, pyrimidinyl, isoxazole, pyrazine, imidazolidinyl, imidazolinyl, morpholinyl, piperazinyl, piperidyl, piperidonyl, pyrazolidinyl, pyrazolinyl, pyrrolidinyl, pyrrolinyl, tetrahydropyranyl, thiomorpholinyl, naphthyl, indanyl or tetralinyl, phenyl, cyclohexyl, cyclopentyl, cyclohexenyl, cycloheptyl, cycloheptenyl, azetidinyl, homopiperazinyl or azepanyl.

In this specification, unless stated otherwise, the term "=$NR^5$" and "=$NOR^5$" include imino- and oximogroups carrying an $R^5$ substituent and may be, or be part of, groups is including, but not limited to iminoalkyl, iminohydroxy, iminoalkoxy, amidine, hydroxyamidine, alkoxyamidine.

In the case where a subscript is the integer 0 (zero) the group to which the subscript refers to indicates that the group is absent, i.e. there is a direct bond between the groups.

In this specification, unless stated otherwise, the term "bond" may be a saturated or unsaturated bond.

In this specification, unless stated otherwise, the term "halo" may be fluoro, chloro, bromo or iodo.

In this specification, unless stated otherwise, the term "alkylhalo" means an alkyl group as defined above, which is substituted with one or more halo. The term "$C_{1-6}$alkylhalo" may include, but is not limited to fluoromethyl, difluoromethyl, trifluoromethyl, fluoroethyl, difluoroethyl, bromopropyl. The term "$OC_{1-6}$alkylhalo" may include, but is not limited to fluoromethoxy, difluoromethoxy, trifluoromethoxy, fluoroethoxy, difluoroethoxy.

Embodiments of the present invention include compounds of claim 1 where P is selected from the group consisting of $C_{3-7}$alkyl and a 3- to 8-membered ring containing one or more atoms independently selected from C, N, O or S, wherein said ring may be fused with a 5- or 6-membered ring containing one or more atoms independently selected from C, N, O or S. In a preferred embodiment of the invention, P is selected from $C_{3-7}$alkyl and a 3- to 8-membered ring containing one or more atoms independently selected from C, N, O or S. In a more preferred embodiment P is selected from a 3- to 8-membered ring containing one or more atoms independently selected from C, N, O or S, wherein said ring may be fused with a 5- or 6-membered ring containing one or more atoms independently selected from C, N, O or S.

In yet a more peferred embodiment P is selected from a 5- or 6- membered aromatic and heteroaromatic ring. In another preferred embodiment of the invention P is phenyl.

P is optionally subsituted with 0, 1, 2, 3 or 4 groups $R^1$, wherein the number of groups $R^1$ is designated by the term m. In preferred embodiment of the invention m is 0, 1 or 2. In more preferred embodiments m is1.

In suitable embodiments of the invention $R^1$ is selected from hydrogen, hydroxy, halo, nitro, $C_{1-6}$alkylhalo, $OC_{1-6}$alkylhalo, $C_{1-6}$alkyl, $OC_{1-6}$alkyl, $C_{2-6}$alkenyl, $OC_{2-6}$alkenyl, $C_{2-6}$alkynyl, $OC_{2-6}$alkynyl, $C_{0-6}$alkyl$C_{3-6}$cycloalkyl, $OC_{0-6}$alkyl$C_{3-6}$cycloalkyl, $C_{0-6}$alkylaryl, $OC_{0-6}$alkylaryl, $(CO)R^8$, $O(CO)R^8$, $O(CO)OR^8$, $C_{1-6}$alkyl$OR^8$, $OC_{2-6}$alkyl$OR^8$, $C_{1-6}$alkyl$(CO)R^8$, $OC_{1-6}$alkyl$(CO)R^8$, $C_{0-6}$alkyl$CO_2R^8$, $OC_{1-6}$alkyl$CO_2R^8$, $C_{0-6}$alkylcyano, $OC_{2-6}$alkylcyano, $C_{0-6}$alkyl$NR^8R^9$, $OC_{2-6}$alkyl$NR^8R^9$, $C_{1-6}$alkyl$(CO)NR^8R^9$, $OC_{1-6}$alkyl$(CO)NR^8R^9$, $C_{0-6}$alkyl$NR^8(CO)R^9$, $OC_{2-6}$alkyl$NR^8(CO)R^9$, $C_{0-6}$alkyl$NR^8(CO)NR^8R^9$, $C_{0-6}SR^8$, $OC_{2-6}$alkyl$SR^8$, $C_{0-6}$alkyl$(SO)R^8$, $OC_{2-6}$alkyl$(SO)R^8$, $C_{0-6}$alkyl$SO_2R^8$, $OC_{2-6}$alkyl$SO_2R^8$, $C_{0-6}$alkyl$(SO_2)NR^8R^9$, $OC_{2-6}$alkyl$(SO_2)NR^8R^9$, $C_{0-6}$alkyl$NR^8(SO_2)R^9$, $OC_{2-6}$alkyl$NR^8(SO_2)R^9$, $C_{0-6}$alkyl$NR^8(SO_2)NR^8R^9$, $OC_{2-6}$alkyl$NR^8(SO_2)NR^8R^9$, $(CO)NR^8R^9$, $O(CO)NR^8R^9$, $NR^8OR^9$, $C_{0-6}$alkyl$NR^8(CO)OR^9$, $OC_{0-6}$alkyl$NR^8(CO)OR^9$, $SO_3R^8$ and a 5- or 6-membered ring containing one or more atoms independently selected from C, N, O or S, wherein said ring may be substituted by one or more A.

In a more suitable embodiment of the invention $R^1$ is selected from hydrogen, hydroxy, halo, nitro, $OC_{1-6}$alkylhalo, $C_{1-6}$alkyl, $OC_{1-6}$alkyl, $C_{2-6}$alkenyl, $OC_{2-6}$alkenyl, $C_{2-6}$alkynyl, $OC_{2-6}$alkynyl, $C_{0-6}$alkyl$C_{3-6}$cycloalkyl, $OC_{0-6}$alkyl$C_{3-6}$cycloalkyl, $C_{0-6}$alkylaryl, $OC_{0-6}$alkylaryl, $(CO)R^8$, $O(CO)R^8$, $O(CO)OR^3$, $C_{1-6}$alkyl$OR^8$, $OC_{2-6}$alkyl$OR^8$, $C_{1-6}$alkyl$(CO)R^8$, $OC_{1-6}$alkyl$(CO)R^8$, $C_{0-6}$alkyl$CO_2R^8$, $OC_{1-6}$alkyl$CO_2R^8$, $C_{0-6}$alkylcyano, $C_{0-6}$alkyl$NR^8R^9$, $OC_{2-6}$alkyl$NR^8R^9$, $C_{1-6}$alkyl$(CO)NR^8R^9$, $OC_{1-6}$alkyl$(CO)NR^8R^9$, $C_{0-6}$alkyl$NR^8(CO)R^9$, $OC_{2-6}$alkyl$NR^8(CO)R^9$, $C_{0-6}$alkyl$NR^8(CO)NR^8R^9$, $C_{0-6}$alkyl$SR^3$, $OC_{2-6}$alkyl$SR^8$, $C_{0-6}$alkyl$(SO)R^8$, $OC_{2-6}$alkyl$(SO)R^8$, $C_{0-6}$alkyl$SO_2R^8$, $OC_{2-6}$alkyl$SO_2R^8$, $C_{0-6}$alkyl$NR^8(SO_2)R^9$, $OC_{2-6}$alkyl$NR^8(SO_2)R^9$, $(CO)NR^8R^9$, $NR^8OR^9$, $C_{0-6}$alkyl$NR^8(CO)OR^9$ and a 5- or 6-membered ring containing one or more atoms independently selected from C, N, O or S, wherein said ring may be substituted by one or more A.

In yet a more suitable embodiment $R^1$ is selected from hydrogen, halo, $C_{0-6}$alkylcyano, $OC_{1-6}$alkyl, a 5-or 6 member aromatic group or a 5- or 6 membered heteroaromatic group.

In yet a more suitable embodiment $R^1$ is selected from F, cyano, methyl, ethyl, methoxy, and imidazole.

In a more suitable embodiment $R^1$ is cyano.

Embodiments of the invention further include compounds of formula I wherein $M^1$ is either a direct bond between P and the core ring or $M^1$ is selected from $C_{1-3}$alkyl, $C_{2-3}$alkenyl, $C_{2-3}$alkynyl, $C_{0-4}$alkyl$(CO)C_{0-4}$alkyl, $C_{0-3}$alkyl$OC_{0-3}$alkyl, $C_{0-3}$alkyl$(CO)NR^8$, $C_{0-3}$alkyl$(CO)NR^8C_{1-3}$alkyl, $C_{0-4}$alkyl$NR^8R^9$, $C_{0-3}$alkyl$SC_{0-3}$alkyl, $C_{0-3}$alkyl$(SO)C_{0-3}$alkyl and $C_{0-3}$alkyl$(SO_2)C_{0-3}$alkyl.

In preferred embodiment $M^1$ is selected from a bond, $C_{1-3}$alkyl, $C_{2-3}$alkenyl, $C_{2-3}$alkynyl, $C_{0-4}$alkyl$(CO)C_{0-4}$alkyl, $C_{0-3}$alkyl$(CO)NR^8$ and $C_{0-3}$alkyl$(CO)NR^8C_{1-3}$alkyl. In a more preferred embodiment $M^1$ is a bond.

When $M^1$ is not a bond $M^1$ may be substituted with 0, 1, 2 or 3 substituents $R^2$ wherein the number of substituents $R^2$ is designated by the term n. The substituents $R^2$ may be independently selected from hydrogen, hydroxy, oxo, =$NR^8$, =$NOR^8$, $C_{1-4}$alkylhalo, halo, $C_{1-4}$alkyl, $O(CO)C_{1-4}$alkyl, $C_{1-4}$alkyl$(SO)C_{0-4}$alkyl, $C_{1-4}$alkyl$(SO_2)C_{0-4}$alkyl, $(SO)C_{0-4}$alkyl, $(SO_2)C_{0-4}$alkyl, $OC_{1-4}$alkyl, $C_{0-4}$alkylcyano, $C_{1-4}$alkyl$OR^8$ and $C_{0-4}$alkyl$NR^8R^9$. In a preferred embodiment $R^2$ is selected from hydrogen, hydroxy, oxo, $C_{1-4}$alkyl, $OC_{1-4}$alkyl, $C_{0-4}$alkylcyano, $C_{1-4}$alkyl$OR^8$ and $C_{0-4}$alkyl$NR^8R^9$.

Suitable embodiments of the invention include compounds of formula 1 where $X^1$, $X^2$ and $X^3$ are independently selected from N, NR, O, CR, =O and S, and R is selected from hydrogen, $C_{0-3}$alkyl, halo, $C_{0-3}$alkyl$OR^5$, $C_{0-3}$alkyl$NR^5R^6$, $C_{0-3}$alkyl$(CO)OR^5$, $C_{0-3}$alkyl$NR^5R^6$ and $C_{0-3}$alkylaryl. In a more suitable embodiment $X^1$, $X^2$ and $X^3$ are independently selected from CR, N, NR, O and S.

In yet a more suitable embodiment $X_1$, $X^2$ and $X^3$ are independently selected from N, O and S. In another suitable embodiment $X^1$ is N.

In yet another suitable embodiment $X^2$ and $X^3$, are independently selected from N and O. In another embodiment $X_1$ and $X^2$ are N and $X^3$ is O. In yet a further suitable embodiment $X^2$ is N and $X^3$ is O and in another embodiment $X^2$ is O and $X^3$ is N.

Embodiments of the invention include those wherein $M^2$ is a direct bond from the core ring to the ring Q, and those where $M^2$ is a linker group between the core ring and the ring Q selected from $C_{1-3}$alkyl, $C_{2-3}$alkenyl, $C_{2-3}$alkynyl, $C_{0-4}$alkyl$(CO)C_{0-4}$alkyl, $C_{0-3}$alkyl$OC_{0-3}$alkyl, $C_{0-3}$alkyl$NR^8C_{1-3}$alkyl, $C_{0-3}$alkyl$(CO)NR^8$, $C_{0-4}$alkyl$NR^8R^9$, $C_{0-3}$alkyl$SC_{0-3}$alkyl, $C_{0-3}$alkyl$(SO)C_{0-3}$alkyl and $C_{0-3}$alkyl$(SO_2)C_{0-3}$alkyl. In a preferred embodiment $M^2$ is selected from a bond, $C_{1-3}$alkyl, $C_{0-4}$alkyl(CO)$C_{0-4}$alkyl and $C_{0-3}$alkylNR$^8$C$_{1-3}$alkyl. In a more preferred embodiment $M^2$ is a bond.

When $M^2$ is not a bond $M^2$ may be further substituted with 0, 1, 2 or 3 substituents $R^3$, wherein the number of substituents $R^3$ is designated by the term n. In a preferred embodiment n is 0. The substituents $R^3$ may be selected from of hydrogen, hydroxy, oxo, =NR$^8$, =NOR$^8$, $C_{1-4}$alkylhalo, halo, $C_{1-4}$alkyl, O(CO)$C_{1-4}$alkyl, $C_{1-4}$alkyl(SO)$C_{0-4}$alkyl, $C_{1-4}$alkyl(SO$_2$)$C_{0-4}$alkyl, (SO)$C_{0-4}$alkyl, (SO$_2$)$C_{0-4}$alkyl, OC$_{1-4}$alkyl, $C_{0-4}$alkylcyano, $C_{1-4}$alkylOR$^8$ and $C_{0-4}$alkylNR$^8$R$^9$.

In a preferred embodiment $R^3$ is selected from hydrogen, oxo, $C_{1-4}$alkylOR$^8$ and $C_{0-4}$alkylNR$^8$R$^9$.

In a suitable embodiment of the invention there are provided compounds of formula 1 wherein Q is a 4-, 5-, 6- or 7-membered ring containing one or more heteroatoms independently selected from N, O or S, wherein said ring may be fused with a 3-, 5- or 6-membered membered ring containing one or more atoms independently selected from C, N, O or S, and wherein the fused ring may be substituted by one or more A.

In a preferred embodiment of the invention Q is selected from 5- and 6-membered carbocyclic and heterocyclic rings containing one or more heteroatoms independently selected from N, O or S wherein said ring may be fused with a 3-, 5- or 6-membered ring containing one or more atoms independently selected from C, N, O or S, and wherein the fused ring may be substituted by one or more A.

In a more preferred embodiment Q is piperidine, pyrolidine, thiazole and morpholine.

The ring Q contains a variable $X^4$, wherein $X^4$ is selected from C, CR and N. In a preferred embodiment $X^4$ is N.

The ring Q may be substituted with 0, 1, 2, 3 or 4 substituents $R^4$ wherein the number of substituents $R^4$ is designated by the term m. The substituent $R^4$ is selected from the group consisting of hydrogen, hydroxy, oxo, =NR$^8$, =NOR$^8$, $C_{1-4}$alkylhalo, halo, $C_{1-4}$alkyl, OC$_{0-6}$alkylaryl, O(CO)$C_{1-4}$alkyl, $C_{1-4}$alkyl(SO)$C_{0-4}$alkyl, $C_{1-4}$alkyl(SO$_2$)$C_{0-4}$alkyl, (SO)$C_{0-4}$alkyl, (SO$_2$)$C_{0-4}$alkyl, OC$_{1-4}$alkyl, $C_{1-4}$alkylOR$^8$, $C_{0-4}$alkylcyano and $C_{0-4}$alkylNR$^8$R$^9$.

In a preferred embodiment m is 0, 1 or 2. In a further preferred embodiment m is 2 and $R^4$ is halo.

The variable $X^4$ is substitued with the group $M^3$ wherein $M^3$ is selected from a bond, $C_{1-4}$alkyl, $C_{0-4}$alkyl(CO)$C_{0-4}$alkyl, $C_{0-3}$alkylOC$_{0-3}$alkyl, $C_{0-4}$alkylNR$^8$R$^9$, $C_{0-3}$alkylNR$^8$C$_{1-3}$alkyl, $C_{0-3}$alkyl(CO)NR$^8$, $C_{0-3}$alkylSC$_{0-3}$alkyl, $C_{0-3}$alkyl(SO)$C_{0-3}$alkyl and $C_{0-3}$alkyl(SO$_2$)$C_{0-3}$ alkyl. In a preferred embodiment of the invention $M^3$ is a direct bond between the ring Q and a group G.

In another preferred embodiment $M^3$ is a linker group between the ring Q and a group G, wherein the linker $M^3$ is selected from $C_{1-4}$alkyl, $C_{0-4}$alkyl(CO)$C_{0-4}$alkyl, $C_{0-3}$alkylOC$_{0-3}$alkyl, $C_{0-4}$alkylNR$^8$R$^9$, $C_{0-3}$alkylNR$^8$C$_{1-3}$alkyl, $C_{0-3}$alkyl(CO)NR$^8$, $C_{0-3}$alkylSC$_{0-3}$alkyl, $C_{0-3}$alkyl(SO)$C_{0-3}$alkyl and $C_{0-3}$alkyl(SO$_2$)$C_{0-3}$alkyl. In a further preferred embodiment $M_3$ is selected from $C_{1-4}$alkyl, $C_{0-4}$alkyl(CO)$C_{0-4}$alkyl, $C_{0-3}$alkylOC$_{0-3}$alkyl and $C_{0-4}$alkylNR$^8$R$^9$. In still a more preferred embodiment $M^3$ is $C_1$alkyl.

When $M^3$ is not a direct bond $M^3$ can be further substituted with 0, 1, 2 or 3 substituents $R^5$ wherein the number of substituents $R^5$ is designated by the variable n. The substituent $R^5$ is selected from the group consisting of hydrogen, hydroxy, oxo, =NR$^8$, =NOR$^8$, $C_{1-4}$alkylhalo, halo, $C_{1-4}$alkyl, O(CO)$C_{1-4}$alkyl, $C_{1-4}$alkyl(SO)$C_{0-4}$alkyl, $C_{1-4}$alkyl(SO$_2$)$C_{0-4}$alkyl, (SO)$C_{0-4}$alkyl, (SO$_2$)$C_{0-4}$alkyl, OC$_{1-4}$alkyl, $C_{0-4}$alkylcyano, $C_{1-4}$alkylOR$^8$ and $C_{0-4}$alkylNR$^8$R$^9$.

In a preferred embodiment $R^5$ is selected from hydrogen, hydroxy, oxo and $C_{0-4}$alkylNR$^8$R$^9$.

In suitable embodiments of the invention the group G is selected from $R^6$ and $R^7$ wherein $R^6$ is selected from hydrogen and a 5- or 6-membered ring containing one or more atoms independently selected from C, N, O or S, wherein said ring may be fused with a 5- or 6-membered ring containing one or more atoms independently selected from C, N, O or S, and wherein any of the rings may be substituted by one or more A, and $R^7$ is selected from hydrogen, $C_{0-4}$alkylcyano, C=NR$^8$(NR$^8$R$^9$), C=NOR$^8$(N$^8$R$^9$), NR$^8$C=NR$^8$(NR$^8$R$^9$), NR$^8$(C=CCN)(NR$^8$R$^9$), NR$^8$(C=CNO$_2$)(N$^8$R$^9$), NR$^8$(C=NCN)(NR$^8$R$^9$), CONR$^8$R$^9$ and NR$^8$(CO)NR$^8$R$^9$.

In a more preferred embodiment of the invention G is selected from the group consisting of 5- or 6-membered ring containing one or more atoms independently selected from C, N, O or S, wherein said ring may be fused with a 5- or 6-membered ring containing one or more atoms independently selected from C, N, O or S, and wherein any of the rings may be substituted by one or more A.

In a more preferred embodiment of the invention G is selected from 5- and 6 membered heteroaryl rings and benzofused heteroaryl rings.

In a further preferred embodiment of the invention G is selected from the group consisting of optionally substituted pyridine, optionally substituted thiazole, optionally substituted imidazole, optionally substituted pyrimidine, optionally substituted oxazole, quinoline, optionally substituted benzoimidazole, optionally substituted pyrazine, optionally substituted prymidine, optionally substituted oxadiazole, optionally substituted benzothiazole, optionally substituted isoxazole and optionally substituted thiophene. Wherein the optional substituent is A, and A is selected from the group consisting of hydrogen, hydroxy, oxo, halo, nitro, $C_{1-6}$alkyl, $C_{0-6}$alkylC$_{3-6}$cycloalkyl, $C_{1-6}$alkylhalo, OC$_{1-6}$alkylhalo, $C_{2-6}$alkenyl, OC$_{1-6}$alkyl, $C_{0-3}$alkylaryl, $C_{1-6}$alkylOR$^8$, OC$_{2-6}$ alkylOR$^8$, $C_{1-6}$alkylSR$^8$, OC$_{2-6}$alkylSR$^8$, (CO)R$^8$, O(CO)R$^8$, OC$_{2-6}$alkylcyano, $C_{0-6}$alkylcyano, $C_{0-6}$alkylCO$_2$R$^8$, OC$_{1-6}$alkylCO$_2$R$^8$, O(CO)OR$^8$, OC$_{1-6}$alkyl(CO)R$^8$, $C_{1-6}$alkyl(CO)R$^8$, NR$^8$OR$^9$, $C_{0-6}$alkylNR$^8$R$^9$, OC$_{2-6}$ alkylNR$^8$R$^9$, $C_{0-6}$alkyl(CO)NR$^8$R$^9$, OC$_{1-6}$alkyl(CO)NR$^8$R$^9$, OC$_{2-6}$alkylNR$^8$(CO)R$^9$, $C_{0-6}$alkylNR$^8$(CO)R$^9$, $C_{0-6}$alkylNR$^8$(CO)NR$^8$R$^9$, O(CO)NR$^8$R$^9$, NR$^8$(CO)OR$^9$, $C_{0-6}$alkyl(SO$_2$)NR$^8$R$^9$, OC$_{2-6}$alkyl(SO$_2$)NR$^8$R$^9$, $C_{0-6}$alkylNR$^8$(SO$_2$)R$^9$, OC$_{2-6}$alkylNR$^8$(SO$_2$)R$^9$, SO$_3$R$^8$, $C_{1-6}$alkylNR$^8$(SO$_2$)NR$^8$R$^9$, OC$_{2-6}$alkyl(SO$_2$)R$^8$, $C_{0-6}$alkyl(SO$_2$)R$^8$, C$^{0-6}$alkyl(SO)R$^8$ and OC$_{2-6}$alkyl(SO)R$^8$.

In a preferred embodiment of the invention A is selected from hydrogen, halo, $C_{1-6}$alkyl, OC$_{1-6}$alkyl and $C_{0-6}$alkylcyano.

In a further preferred embodiment G is pyridine. In yet a further preferred embodiment G is optionally substituted pyridine, wherein the substituents are selected from hydrogen, halo, methyl, methoxy and cyano.

A further aspect of the invention relates to compounds of formula I, wherein:
P is selected from the group consisting of $C_{3-7}$alkyl and a 3- to 8-membered ring containing one or more atoms independently selected from C, N, O or S;
$R^1$ is selected from the group consisting of hydrogen, hydroxy, halo, nitro, OC$_{1-6}$alkylhalo, $C_{1-6}$alkyl, OC$_{1-6}$alkyl, $C_{2-6}$alkenyl, OC$_{2-6}$alkenyl, $C_{2-6}$alkynyl, OC$_{2-6}$alkynyl, $C_{0-6}$alkylC$_{3-6}$cycloalkyl, OC$_{0-6}$alkylC$_{3-6}$cycloalkyl, $C_{0-6}$alkylaryl, $OC_{0-6}$alkylaryl, (CO)$R^8$, O(CO)$R^8$, O(CO)O$R^8$, $C_{1-6}$alkylO$R^8$, $OC_{2-6}$alkylO$R^8$, $C_{1-6}$alkyl(CO)$R^8$, $OC_{1-6}$alkyl(CO)$R^8$, $C_{0-6}$alkylCO$_2R^8$, $OC_{1-6}$alkylCO$_2R^8$, $C_{0-6}$alkylcyano, $C_{0-6}$alkylN$R^8R^9$, $OC_{2-6}$alkylN$R^8R^9$, $C_{1-6}$alkyl(CO)N$R^8R^9$, $OC_{1-6}$alkyl(CO)N$R^8R^9$, $C_{0-6}$alkylN$R^8$(CO)$R^9$, $OC_{2-6}$alkylN$R^8$(CO)$R^9$, $C_{0-6}$alkylN$R^8$(CO)N$R^8R^9$, $C_{0-6}$alkylS$R^8$, $OC_{2-6}$alkylS$R^8$, $C_{0-6}$alkyl(SO)$R^8$, $OC_{2-6}$alkyl(SO)$R^8$, $C_{0-6}$alkylSO$_2R^8$, $OC_{2-6}$alkylSO$_2R^8$, $C_{0-6}$alkylN$R^8$(SO$_2$)$R^9$, $OC_{2-6}$alkylN$R^8$(SO$_2$)$R^9$, (CO)N$R^8R^9$, N$R^8$O$R^9$, $C^{0-6}$alkylN$R^8$(CO)O$R^9$ and a 5- or 6-membered ring containing one or more atoms independently selected from C, N, O or S, wherein said ring may be substituted by one or more A;

$M^1$ and a bond, $C_{1-3}$alkyl, $C_{2-3}$alkenyl, $C_{2-3}$alkynyl, $C_{0-4}$alkyl(CO)$C_{0-4}$alkyl, $C_{0-3}$alkyl(CO)N$R^8$ and $C_{0-3}$alkyl(CO)N$R^8C_{1-3}$alkyl;

$R^2$ is selected from the group consisting of hydrogen, hydroxy, oxo, $C_{1-4}$alkyl, O$C_{1-4}$alkyl, $C_{0-4}$alkylcyano, $C^{1-4}$alkylO$R^8$ and $C_{0-4}$alkylN$R^8R^9$;

$X^1$, $X^2$ and $X^3$ are independently selected from N, O, C, =O and S;

R is selected from the group consisting of $C_{0-3}$alkyl, halo, $C_{0-3}$alkylO$R^5$, $C_{0-3}$alkylN$R^5R^6$, $C_{0-3}$alkyl(CO)O$R^5$, $C^{0-3}$alkylN$R^5R^6$ and $C_{0-3}$alkylaryl;

$M^2$ is selected from the group consisting of a bond, $C_{1-3}$alkyl, $C_{0-4}$alkyl(CO)$C_{0-4}$alkyl and $C_{0-3}$alkylN$R^8C_{1-3}$alkyl;

$R^3$ is selected from the group consisting of hydrogen, oxo, $C_{1-4}$alkylO$R^8$ and $C_{0-4}$alkylN$R^8R^9$;

Q is a 4-, 5-, 6- or 7-membered ring containing one or more heteroatoms independently selected from N, O or S, wherein said ring may be fused with a 3-, 5- or 6-membered ring containing one or more atoms independently selected from C, N, O or S, and wherein the fused ring may be substituted by one or more A;

$R^4$ is selected from the group consisting of hydrogen, hydroxy, oxo, halo, $C_{1-4}$alkyl, $C_{1-4}$alkylO$R^8$, $C_{0-4}$alkylcyano and $C_{0-4}$alkylN$R^8R^9$;

$M^3$ is selected from the group consisting of a bond, $C_{1-4}$alkyl, $C_{0-4}$alkyl(CO)$C_{0-4}$alkyl, $C_{0-3}$alkylO$C_{0-3}$alkyl and $C_{0-4}$alkylN$R^8R^9$;

$R^5$ is selected from the group consisting of hydrogen, hydroxy, oxo and $C_{0-4}$alkylN$R^8R^9$;

G is $R^6$ or $R^7$;

$R^6$ is selected from the group consisting of hydrogen and a 5- or 6-membered ring containing one or more atoms independently selected from C, N, O or S, wherein said ring may be fused with a 5- or 6-membered ring containing one or more atoms independently selected from C, N, O or S, and wherein any of the rings may be substituted by one or more A;

$R^7$ is selected from the group consisting of hydrogen, $C_{0-4}$alkylcyano, C=N$R^8$(N$R^8R^9$), C=NO$R^8$(N$R^8R^9$), N$R^8$C=N$R^8$(N$R^8R^9$), N$R^8$(C=CCN)(N$R^8R^9$), N$R^8$(C=CNO$_2$)(N$R^8R^9$), N$R^8$(C=NCN)(N$R^8R^9$), CONR$^8R^9$ and N$R^8$(CO)N$R^8R^9$;

$R^8$ and $R^9$ are independently selected from hydrogen, $C_{1-6}$alkyl, $C_{0-6}$alkyl$C_{3-6}$cycloalkyl, $C_{0-6}$alkylaryl, $C_{0-6}$alkylheteroaryl and a 5- or 6-membered ring containing one or more atoms independently selected from C, N, O or S, and wherein $R^8$ and $R^9$ may together form a 5- or 6-membered ring containing one or more atoms independently selected from C, N, O or S;

A is selected from the group consisting of hydrogen, hydroxy, oxo, halo, $C_{1-6}$alkyl, $C_{1-6}$alkylhalo, O$C_{1-6}$alkylhalo, O$C_{1-6}$alkyl, $C_{0-3}$alkylaryl, $C_{1-6}$alkylO$R^8$, $C_{0-6}$alkylcyano and $C_{0-6}$alkylN$R^8R^9$;

m is 0, 1, 2 or 3; and n is 0, 1 or 2;

or salt thereof.

In yet another aspect of the invention relates to compounds of formula I, wherein:

$M^1$ is selected from the group consisting of a bond, $C_{1-3}$alkyl, $C_{2-3}$alkenyl, $C_{2-3}$alkynyl, $C_{0-4}$alkyl(CO)$C_{0-4}$alkyl, $C_{0-3}$alkyl(CO)N$R^8$ and $C_{0-3}$alkyl(CO)N$R^8C_{1-3}$alkyl;

$R^2$ is selected from the group consisting of hydrogen, hydroxy, oxo, $C_{1-4}$alkyl, O$C_{1-4}$alkyl, $C_{0-4}$alkylcyano, $C^{1-4}$alkylO$R^8$ or $C_{0-4}$alkylN$R^8R^9$;

$M^2$ is selected from the group consisting of a bond, $C_{1-3}$alkyl, $C_{0-4}$alkyl(CO)$C_{0-4}$alkyl andr $C_{0-3}$alkylN$R^8R^9C_{1-3}$alkyl;

$R^3$ is selected from the group consisting of hydrogen, oxo, $C_{1-4}$alkylO$R^8$ and $C_{0-4}$alkylN$R^8R^9$;

$M^3$ is selected from the group consisting of a bond, $C_{1-4}$alkyl, $C_{0-4}$alkyl(CO)$C_{0-4}$alkyl, $C_{0-3}$alkylO$C_{0-3}$alkyl and $C_{0-4}$alkylN$R^8R^9$;

$R^5$ is selected from the group consisting of hydrogen, hydroxy, oxo and $C_{0-4}$alkylN$R^8R^9$.

One aspect of the invention relates to compounds of formula I, wherein:

$X^1$, $X^2$ and $X^3$ are independently selected from N, O, C, =O and S;

R is selected from the group consisting of $C_{0-3}$alkyl, halo, $C_{0-3}$alkylO$R^5$, $C_{0-3}$alkylN$R^5R^6$, $C_{0-3}$alkyl(CO)O$R^5$, $C^{0-3}$alkylN$R^5R^6$ and $C_{0-3}$alkylaryl.

In one aspect of the invention G is pyridine, thiazole, benzoimidazole, quinoline, imidazole, oxadiazole, benzothiazole, pyrimidine, isoxazole or pyrazine.

Yet a further aspect of the nvention relates to compounds of formula I, wherein:

$R^4$ is selected from the group consisting of hydrogen, hydroxy, oxo, halo, $C_{1-4}$alkyl, $C_{1-4}$alkylO$R^8$, $C_{0-4}$alkylcyano and $C_{0-4}$alkylN$R^8R^9$.

One aspect of the nvention relates to compounds of formula I, wherein:

$R^6$ is selected from the group consisting of hydrogen and a 5- or 6-membered ring containing one or more atoms independently selected from C, N, O or S, wherein said ring may be fused with a 5- or 6-membered ring containing one or more atoms independently selected from C, N, O or S, and wherein any of the rings may be substituted by one or more A;

$R^7$ is selected from the group consisting of hydrogen, $C_{0-6}$alkylcyano, C=N$R^8$(N$R^8R^9$), C=NO$R^8$(N$R^8R^9$), N$R^8$C=N$R^8$(N$R^8R^9$), N$R^8$(C=CCN)(N$R^8R^9$), N$R^8$(C=CNO$_2$)(N$R^8R^9$), N$R^8$(C=NCN)(N$R^8R^9$), CONR$^8R^9$ and N$R^8$(CO)N$R^8R^9$.

Still another aspect of the invention relates to compounds of formula I in which:

$X^1$ and $X^2$ are N;

$X^3$ is O; and $X^4$ is N;

$M^2$ is a bond;

$M^3$ is $C_{1-3}$alkyl;

P is a 5- or 6-membered ring containing one or more atoms independently selected from C, N, O or S, wherein said ring may be fused with a 5- or 6-membered ring containing one or more atoms independently selected from C, N, O or S; and Q is a 5- or 6-membered ring containing one or more atoms independently selected from C, N, O or S, wherein said ring may be fused with a 5- or 6-membered ring containing one or more atoms independently selected from C, N, O or S.

Specific embodiments of the invention include,

3-[5-(1-Pyridin-2-ylmethyl-piperidin-2-yl)-[1,2,4]oxadiazol-3-yl]-benzonitrile,
3-[3-(1-Pyridin-2-ylmethyl-piperidin-2-yl)-[1,2,4]oxadiazol-5-yl]-benzonitrile,
3-[5-(1-Thiazol-2-ylmethyl-piperidin-2-yl)-[1,2,4]oxadiazol-3-yl]-benzonitrile,
3-{5-[1-(1-Methyl-1H-imidazol-2-ylmethyl)-piperidin-2yl]-[1,2,4]oxadiazol-3-yl}-benzonitrile,
3-{5-[1-(6-Methyl-pyridin-2-ylmethyl)-piperidin-2-yl]-[1,2,4]oxadiazol-3-yl}-benzonitrile,
3-[3-(1-Thiazol-2-ylmethyl-piperidin-2-yl)-[1,2,4]oxadiazol-5-yl]-benzonitrile,
3-[5-(1-Thiazol-2-ylmethyl-pyrrolidin-2-yl)-[1,2,4]oxadiazol-3-yl]-benzonitrile,
3-{5-[1-(5-Chloro-pyridin-2-ylmethyl)-piperidin-2-yl]-[1,2,4]oxadiazol-3-yl}-benzonitrile,
2-[2-(5-m-Tolyl-[1,2,4]oxadiazol-3-yl)-piperidin-1-ylmethyl]-pyridine,
3-{5-[1-(5-Fluoro-pyridin-2-ylmethyl)-piperidin-2-yl]-[1,2,4]oxadiazol-3-yl}-benzonitrile,
3-[5S-(3-Pyridin-2-ylmethyl-thiazolidin-4-yl)-[1,2,4]oxadiazol-3-yl]-benzonitrile,
3-{5-[1-(3-Methyl-pyridin-2-ylmethyl)-piperidin-2-yl]-[1,2,4]oxadiazol-3-yl}-benzonitrile,
3-{5-[1-(4-Methyl-pyridin-2-ylmethyl)-piperidin-2-yl]-[1,2,4]oxadiazol-3-yl}benzonitrile,
3-{5-[1-(5-Methyl-pyridin-2-ylmethyl)-piperidin-2-yl]-[1,2,4]oxadiazol-3-yl}benzonitrile,
3-{5-[1-(1-Methyl-1H-benzoimidazol-2-ylmethyl)-piperidin-2-yl]-[1,2,4]oxadiazol-3-yl}-benzonitrile,
3-[5-(6-Methyl-1-pyridin-2-ylmethyl-piperidin-2-yl)-[1,2,4]oxadiazol-3-yl]-benzonitrile,
3-[5-(4,4-Difluoro-1-pyridin-2-ylmethyl-piperidin-2-yl)-[1,2,4]oxadiazol-3-yl]-benzonitrile,
3-[5-(4,4-Difluoro-1-thiazol-2-ylmethyl-piperidin-2-yl)-[1,2,4]oxadiazol-3-yl]-benzonitrile,
3-[5-(1-Quinolin-2-ylmethyl-piperidin-2-yl)-[1,2,4]oxadiazol-3-yl]-benzonitrile,
3-{5-[1-(1H-Benzimidazole-2-ylmethyl)-piperidin-2-yl]-[1,2,4]oxadiazol-3-yl}-benzonitrile,
3-{5-[1-(2-Methyl-thiazol-4-ylmethyl)-piperidin-2-yl]-[1,2,4]oxadiazol-3-yl}benzonitrile,
3-{5-[1-(1-Benzyl-1H-imidazol-2-ylmethyl)-piperidin-2-yl]-[1,2,4]oxadiazol-3-yl}-benzonitrile,
3-[5-(4-Pyridine-2-ylmethyl-morpholin-3-yl)-[1,2,4]oxadiazol-3-yl)-benzonitrile,
3-{5-[1-(6-Bromo-pyridin-2-ylmethyl)-piperidin-2-yl]-[1,2,4]oxadiazol-3-yl}-benzonitrile,
3-{5-[1-(4-Methoxy-3,5-dimethyl-pyridin-2-ylmethyl)-piperidin-2-yl]-[1,2,4]oxadiazol-3-yl}-benzonitrile,
3-{5-[1-(6-Chloro-pyridin-2-ylmethyl)-piperidin-2-yl]-[1,2,4]oxadiazol-3-yl}-benzonitrile,
3-[5-(1-Pyrazin-2-ylmethyl-piperidin-2-yl)-[1,2,4]oxadiazol-3-yl]-benzonitrile,
3-[5-(1-Pyrimidin-4-ylmethyl-piperidin-2-yl)-[1,2,4]oxadiazol-3-yl]-benzonitrile,
3-{5-[1-(5-Methyl-[1,2,4]oxadiazol-3-ylmethyl)-piperidin-2-yl]-[1,2,4oxadiazol-3-yl}-benzonitrile,
3-{5-[1-(4-Chloro-pyridin-2-ylmethyl)-piperidin-2-yl]-[1,2,4]oxadiazol-3-yl}-benzonitrile,
2-{2-[3-(3-Cyano-phenyl)-[1,2,4]oxadiazol-5-yl]-piperidin-1-ylmethyl}-thiazole-4-carbonitrile,
3-[5-(1-Benzothiazol-2-ylmethyl-piperidin-2-yl)-[1,2,4]oxadiazol-3-yl]benzonitrile,
6-{2-[3-(3-Cyano-phenyl)-[1,2,4]oxadiazol-5-yl]-piperidin-1-ylmethyl}-nicotinonitrile,
3-{5-[1-(5-Methyl-isoxazol-3-ylmethyl)-piperidin-2-yl]-[1,2,4]oxadiazol-3-yl}-benzonitrile,
3-Methoxy-5-[3-(1-pyridin-2-ylmethyl-piperidin-2-yl)-[1,2,4]oxadiazol-5-yl]-benzonitrile,
2-{2-[5-(3-Methoxy-phenyl)-[1,2,4]oxadiazol-3-yl]-piperidin-1-ylmethyl}-pyridine,
3-[5-(1-Pyridin-2-ylmethyl-pyrrolidin-2-yl)-[1,2,4]oxadiazol-3-yl]-benzonitrile,
2-{2-[3-(3-Methoxy-phenyl)-[1,2,4]oxadiazol-5-yl]-piperidin-1-ylmethyl}-pyridine,
(RS)-2-[2-(3-Thiophen-2-yl-[1,2,4]oxadiazol-5-yl)-piperidin-1-ylmethyl]-pyridine,
2-[2-(3-Phenyl-[1,2,4]oxadiazol-5-yl)-piperidin-1-ylmethyl]-pyridine,
2-[2-(3-m-Tolyl-[1,2,4]oxadiazol-5-yl)-piperidin-1-ylmethyl]-pyridine,
(RS)-2-[2-(3-m-Tolyl-[1,2,4]oxadiazol-5-yl)-piperidin-1-ylmethyl]-pyridine,
(RS)-2-{2-[3-(3-Fluoro-5-imidazol-1-yl-phenyl)-[1,2,4]oxadiazol-5-yl]-piperidin-1-ylmethyl}-pyridine or
2-{2-[3-(3-Ethyl-phenyl)-[1,2,4]oxadiazol-5-yl]-piperidin-1-ylmethyl}-pyridine, or salt thereof.

Further specific embodiments of the invention include:
(R)- and (S)-3-[5-(1-Pyridin-2-ylmethyl-piperidin-2-yl)-[1,2,4]oxadiazol-3-yl]-benzonitrile;
(S)-3-[5-(1-Thiazol-2-ylmethyl-piperidin-2-yl)-[1,2,4]oxadiazol-3-yl]-benzonitrile;
3-[5S-(3-Thiazol-2-ylmethyl-thiazolidin-4-yl)-[1,2,4]oxadiazol-3-yl]-benzonitrile;
(S)-3-[5-(1-Thiazol-2-ylmethyl-pyrrolidin-2-yl)-[1,2,4]oxadiazol-3-yl]-benzonitrile;
(S)-3-[5-(1-Pyridin-2-ylmethyl-pyrrolidin-2-yl)-[1,2,4]oxadiazol-3-yl]-benzonitrile;
(S)-3-[5-(1-Pyridin-2-ylmethyl-2,5-dihydro-1H-pyrrol-2-yl)-[1,2,4]oxadiazol-3-yl]-benzonitrile;
Trans-3-[5-(5-methyl-1-pyridin-2-ylmethyl-piperidin-2-yl)-[1,2,4]oxadiazol-3-yl]-benzonitrile;
Cis-3-[5-(5-methyl-1-pyridin-2-ylmethyl-piperidin-2-yl)-[1,2,4]oxadiazol-3-yl]-benzonitrile;
Cis-3-[5-(5-methyl-1-thiazol-2-ylmethyl-piperidin-2-yl)-[1,2,4]oxadiazol-3-yl]-benzonitrile;
Cis-2-{2-[3-(3-chloro-phenyl)-[1,2,4]oxadiazol-5-yl]-4-methyl-piperidin-1-ylmethyl}-pyridine;
Cis-3-[5-(3-Methyl-1-pyridin-2-ylmethyl-piperidin-2-yl)-[1,2,4]oxadiazol-3-yl]-benzonitrile;
Trans-3-[5-(3-Methyl-1-pyridin-2-ylmethyl-piperidin-2-yl)-[1,2,4]oxadiazol-3-yl]-benzonitrile;
Cis-3-[5-(3-Methyl-1-thiazol-2-ylmethyl-piperidin-2-yl)-[1,2,4]oxadiazol-3-yl]-benzonitrile;
3-[5-(4-Thiazol-2-ylmethyl-morpholin-3-yl)-[1,2,4]oxadiazol-3-yl]-benzonitrile;
3-{5-[4-(4-Methyl-pyridin-2-ylmethyl)-morpholin-3-yl]-[1,2,4]oxadiazol-3-yl}-benzonitrile;
3-[3-(3-Chloro-phenyl)-[1,2,4]oxadiazol-5-yl]-4-pyridin-2-ylmethyl-morpholine;
3-[3-(3-Chloro-phenyl)-[1,2,4]oxadiazol-5-yl]-4-thiazol-2-ylmethyl-morpholine;
2-{2-[3-(3-Chloro-phenyl)-[1,2,4]oxadiazol-5-yl]-piperidin-1-ylmethyl}-pyridine;
2-[3-(3-Chloro-phenyl)-[1,2,4]oxadiazol-5-yl]-1-thiazol-2-ylmethyl-piperidine; or a salt thereof.

The present invention relates to the use of compounds of formula I as hereinbefore defined as well as to the salts thereof. Salts for use in pharmaceutical formulations will be pharmaceutically acceptable salts, but other salts may be useful in the production of the compounds of formula I.

Examples of pharmaceutically acceptable salts may be, but are not limited to hydrochloride, 4-aminobenzoate, anthranilate, 4-aminosalicylate, 4-hydroxybenzoate, 3,4-dihydroxybenzoate, 3-hydroxy-2-naphthoate, nitrate and trifluoroacetate. Other pharmaceutically acceptable salts and methods of preparing these salts may be found in, for example, Remington's Pharmaceutical Sciences (18$^{th}$ Edition, Mack Publishing Co.).

Some compounds of formula I may have chiral centres and/or geometric isomeric centres (E- and Z-isomers), and it is to be understood that the invention encompasses all such optical, diastereoisomers and geometric isomers.

The invention relates to any and all tautomeric forms of the compounds of formula I.

The invention relates to the following compounds, which may be used as intermediates in the preparation of a compound of formula I;
3-cyano-5-methoxybenzoic acid,
3-Fluoro-5-cyano-(1H-imidazol-1-yl)-benzene,
2-Cyano-piperidine-1-carboxylic acid tert-butyl ester,
2-(N-Hydroxycarbamimidoyl)-piperidine-1-carboxylic acid tert-butyl ester,
N-Hydroxy-thiophene-2-carboxamidine,
3-Ethyl-N-hydroxy-benzamidine,
3-Fluoro-5-(1H-imidazol-1-yl)phenyl-amidoxime,
5-Methyl -pyridine-2-carbaldehyde,
4-Methyl-pyridine-2-carbaldehyde,
3-Methyl-pyridine-2-carbaldehyde,
5-Fluoro-pyridine-2-carbaldehyde,
5-Chloro-pyridine-2-carbaldehyde,
3-Chloromethyl-5-methyl-[1,2,4]oxadiazole,
1-Pyridin-2-ylmethyl-piperidine-2-carboxylic acid methyl ester,
(S)-1-Pyridin-2-ylmethyl-piperidine-2-carboxylic acid methyl ester,
6-Methyl-piperidine-2-carboxylic acid,
4-Hydroxy-piperidine-2-carboxylic acid methyl ester,
Piperidine-1,2-dicarboxylic acid-1-tert-butyl ester,
Pyrrolidine-1,2-dicarboxylic acid 1-tert-butyl ester,
6-Methyl-piperidine-1,2-dicarboxylic acid 1-tert-butyl ester,
Morpholine-3,4-dicarboxylic acid-4-tert-butyl ester,
4-Hydroxy-piperidine-1,2-dicarboxylic acid 1-tert-butyl ester 2-methyl ester,
4-Oxo-piperidine-1,2-dicarboxylic acid 1-tert-butyl ester 2-methyl ester,
4,4-Difluoro-piperidine-1,2-dicarboxylic acid 1-tert-butyl ester,
2-[3-(3-Cyano-phenyl)-[1,2,4]oxadiazol-5-yl]-piperidine-1-carboxylic acid tert-butyl ester,
2-[3-(3-Cyano-phenyl)-[1,2,4]oxadiazol-5-yl]-6-methyl-piperidine-1-carboxylic acid tert-butyl ester,
3-[3-(3-Cyano-phenyl)-[1,2,4]oxadiazol-5-yl]-morpholine-4-carboxylic acid tert-butyl ester,
2-[5-(3-Cyano-phenyl)-[1,2,4]oxadiazol-3-yl]-piperidine-1-caboxylic acid tert-butyl ester,
2-[5-(3-Methoxy-phenyl)-[1,2,4]oxadiazol-3-yl]-piperidine-1-caboxylic acid tert-butyl ester,
2-[5-(3-Cyano-5-methoxy-phenyl)-[1,2,4]oxadiazol-3-yl]-piperidine-1-carboxylic acid tert-butyl ester,
2-(5-m-Tolyl-[1,2,4]oxadiazol-3-yl)-piperidine-1-carboxylic acid tert-butyl ester,
2-[3-(3-Cyano-phenyl)-[1,2,4]oxadiazol-5-yl]-4,4-difluoro-piperidine-1-carboxylic acid tert-butyl ester,
2-[3-(3-Cyano-phenyl)-[1,2,4]oxadiazol-5-yl]-pyrrolidine-1-carboxylic acid tert-butyl ester,
3-(5-Piperidin-2-yl-[1,2,4]oxadiazol-3-yl)-benzonitrile,
3-(3-Piperidin-2-yl-[1,2,4]oxadiazol-5-yl)-benzonitrile,
2-[5-(3-Methoxy-phenyl)-[1,2,4]oxadiazol-3-yl]-piperidine,
3-[5-(4,4-Difluoro-piperidin-2-yl)-[1,2,4]oxadiazol-3-yl]-benzonitrile,
3-[5-(6-Methyl-piperidin-2-yl)-[1,2,4]oxadiazol-3-yl]-benzonitrile hydrochloride,
3-Methoxy-5-[3-(1-pyridin-2-ylmethyl-piperidin-2-yl)-[1,2,4]oxadiazol-5-yl]-benzonitrile,
2-[5-m-Tolyl-[1,2,4]oxadiazol-3-yl]-piperidine,
3-(5-Pyrrolidin-2-yl-[1,2,4]oxadiazol-3-yl)-benzonitrile or
3-(5-Morpholin-3-yl-[1,2,4]oxadiazol-3-yl)-benzonitrile.

Pharmaceutical Formulations

According to one aspect of the present invention, a pharmaceutical formulation is provided that comprises a compound of formula I or salt thereof, for use in the prevention and/or treatment of a disorder. This disorder is mediated by metabotropic glutamate receptor subtype 5 (mGluR5) and is illustrated by the disorders listed below.

The composition may be in a form suitable for oral administration, for example as a tablet, pill, syrup, powder, granule or capsule, for parenteral injection (including intravenous, subcutaneous, intramuscular, intravascular or infusion) as a sterile solution, suspension or emulsion, for topical administration as an ointment, patch or cream or for rectal administration as a suppository.

In general the above compositions may be prepared in a conventional manner using one or more conventional excipients, pharmaceutical diluents and/or inert carriers.

According to another aspect of the invention, a pharmaceutical formulation is provided that comprises, as active ingredient, a therapeutically effective amount of a formula I compound in association with one or more pharmaceutically acceptable diluent, excipients and/or inert carrier.

Suitable daily doses of the compounds of formula I in the treatment of a mammal, including man are approximately 0.01 to 250 mg/kg bodyweight at peroral administration and about 0.001 to 250 mg/kg bodyweight at parenteral administration. The typical daily dose of the active ingredients varies within a wide range and will depend on various factors such as the relevant indication, the route of administration, the age, weight and sex of the patient and may be determined by a physician.

Medical Use

It has been found that the compounds according to the present invention, or salts thereof, exhibit a high degree of potency and selectivity for individual metabotropic glutamate receptor (mGluR) subtypes. In particular there are compounds according to the present invention that are potent and selective for the mGluR Group I receptor and more particularly for mGluR5. Accordingly, the compounds of the present invention are expected to be useful in the prevention and/or treatment of conditions associated with excitatory activation of an mGluR Group I receptor and for inhibiting neuronal damage caused by excitatory activation of an mGluR Group I receptor, specifically when the mGluR Group I receptor is mGluR5. The compounds may be used to produce an inhibitory effect of mGluR Group I, especially mGluR5, in mammals, including man.

mGluR5 is highly expressed in the central and peripheral nervous system and in other tissues. Thus, it is expected that the compounds of the invention are well suited for the prevention and/or treatment of mGluR5 receptor-mediated disorders such as acute and chronic neurological and psychiatric disorders and chronic and acute pain disorders.

Further disorders are Alzheimer's disease senile dementia, AIDS-induced dementia, Parkinson's disease, amyotrophic lateral sclerosis, Huntington's Chorea, migraine, epilepsy, schizophrenia, depression, anxiety, acute anxiety, obsessive compulsive disorder, ophthalmological disorders such as retinopathies, diabetic retinopathies, glaucoma, auditory neuropathic disorders such as tinnitus, chemotherapy induced neuropathies, post-herpetic neuralgia and trigeminal neuralgia, tolerance, dependency, addiction and craving disorders, neurodevelopmental disorders including Fragile X, autism, mental retardation, schizophrenia and Down's Syndrome.

The compounds are also well suited for the prevention and/or treatment of pain related to migraine, inflammatory pain, neuropathic pain disorders such as diabetic neuropathies, arthritis and rheumatitiod diseases, low back pain, post-operative pain and pain associated with various conditions including angina, renal or billiary colic, menstruation, migraine and gout.

Other disorders are stroke, head trauma, anoxic and ischemic injuries, hypoglycemia, cardiovascular diseases and epilepsy.

The dose required for the therapeutic or preventive treatment of a particular disorder will necessarily be varied depending on the host treated, the route of administration and the severity of the illness being treated.

The invention relates to compounds of formula I as defined hereinbefore, for use in therapy.

The invention relates to compounds of formula I as defined hereinbefore, for use in prevention and/or treatment of neurological disorders.

The invention relates to compounds of formula I as defined hereinbefore, for use in prevention and/or treatment of psychiatric disorders.

The invention relates to compounds of formula I as defined hereinbefore, for use in prevention and/or treatment of chronic and acute pain disorders.

The invention relates to compounds of formula I as defined hereinbefore, for use in prevention and/or treatment of mGluR5 receptor-mediated disorders.

The invention relates to compounds of formula I as defined hereinbefore, for use in prevention and/or treatment of Alzheimer's disease senile dementia, AIDS-induced dementia, Parkinson's disease, amylotropic lateral sclerosis, Huntington's Chorea, migraine, epilepsy, schizophrenia, depression, anxiety, acute anxiety, ophthalmological disorders such as retinopathies, diabetic retinopathies, glaucoma, auditory neuropathic disorders such as tinnitus, chemotherapy induced neuropathies, post-herpetic neuralgia and trigeminal neuralgia, tolerance, dependency, Fragile X, autism, mental retardation, schizophrenia and Down's Syndrome.

The invention relates to compounds of formula I as defined hereinbefore, for use in prevention and/or treatment of pain related to migraine, inflammatory pain, neuropathic pain disorders such as diabetic neuropathies, arthritis and rheumatitiod diseases, low back pain, post-operative pain and pain associated with various conditions including angina, renal or billiary colic, menstruation, migraine and gout.

The invention relates to compounds of formula I as defined hereinbefore, for use in prevention and/or treatment of stroke, head trauma, anoxic and ischemic injuries, hypoglycemia, cardiovascular diseases and epilepsy.

The present invention relates also to the use of a compound of formula I as defined hereinbefore, in the manufacture of a medicament for the prevention and/or treatment of mGluR5 receptor-mediated disorders and any disorder listed above.

The invention also provides a method of treatment and/or prevention of mGluR5 receptor-mediated disorders and any disorder listed above, in a patient suffering from, or at risk of, said condition, which comprises administering to the patient an effective amount of a compound of formula I, as hereinbefore defined.

In the context of the present specification, the term "therapy" includes treatment as well as prevention, unless there are specific indications to the contrary. The terms "therapeutic" and "therapeutically" should be construed accordingly.

In this specification, unless stated otherwise, the term 'antagonist' means a compound that by any means, partly or completely, blocks the transduction pathway leading to the production of a response by the ligand.

The term "disorder", unless stated otherwise, means any condition and disease associated with metabotropic glutamate receptor activity.

Non-Medical Use

In addition to their use in therapeutic medicine, the compounds of formula I or salt thereof, are also useful as pharmacological tools in the development and standardisation of in vitro and in vivo test systems for the evaluation of the effects of inhibitors of mGluR related activity in laboratory animals such as cats, dogs, rabbits, monkeys, rats and mice, as part of the search for new therapeutics agents.

Pharmacology

The pharmacological properties of the compounds of the invention can be analyzed using standard assays for functional activity. Examples of glutamate receptor assays are well known in the art as described in for example Aramori et al., *Neuron* 8:757 (1992), Tanabe et al., *Neuron* 8:169 (1992), Miller et al., *J. Neuroscience* 15: 6103 (1995), Balazs, et al., *J. Neurochemistry* 69:151 (1997). The methodology described in these publications is incorporated herein by reference. Conveniently, the compounds of the invention can be studied by means of an assay that measures the mobilization of intracellular calcium, $[Ca^{2+}]_i$, in cells expressing mGluR5.

For FLIPR analysis, cells expressing human mGluR5d were seeded on collagen coated clear bottom 96-well plates with black sides and analysis of $[Ca^{2+}]_i$ mobilization was done 24 hours after seeding.

FLIPR experiments were done using a laser setting of 0.800 W and a 0.4 second CCD camera shutter speed. Each FLIPR experiment was initiated with 160 μL of buffer present in each well of the cell plate. After each addition of the compound, the fluorescence signal was sampled 50 times at 1 second intervals followed by 3 samples at 5 second intervals. Responses were measured as the peak height of the response within the sample period. $EC_{50}$ and $IC_{50}$ determinations were made from data obtained from 8-point concentration response curves (CRC) performed in duplicate. Agonist CRC were generated by scaling all responses to the maximal response observed for the plate. Antagonist block of the agonist challenge was normalized to the average response of the agonist challenge in 14 control wells on the same plate.

We have validated a secondary functional assay for mGluR5d based on Inositol Phosphate ($IP_3$) turnover. $IP_3$ accumulation is measured as an index of receptor mediated phospholipase C turnover. GHEK cells stably expressing the human mGluR5d receptors were incubated with [3H] myo-inositol overnight, washed three times in HEPES buffered saline and pre-incubated for 10 minutes with 10 mM LiCl. Compounds (agonists) were added and incubated for 30 minutes at 37° C. Antagonist activity was determined by pre-incubating test compounds for 15 minutes, then incubating in the presence of glutamate (80 µM) or DHPG (30 µM) for 30 minutes. Reactions were terminated by the addition of perchloric acid (5%). Samples were collected and neutralized, and inositol phosphates were separated using Gravity-Fed Ion-Exchange Columns.

A detailed protocol for testing the compounds of the invention is provided below in Pharmaceutical Examples.

One aspect of the invention relates to a method for inhibiting activation of mGluR5 receptors, comprising treating a cell containing said receptor with an effective amount of a compound of formula I.

Abbreviations

| | |
|---|---|
| FLIPR | Fluorometric Imaging Plate reader |
| CCD | Charge Coupled Device |
| CRC | Concentration Response Curve |
| GHEK | Human Embrionic Kidney expressing Glutamate Transporter |
| HEPES | 4-(2-hydroxyethyl)-1-piperazineethanesulfonic acid (buffer) |
| $IP_3$ | inositol triphosphate |
| DHPG | 3,5-dihydroxyphenylglycine; |
| BSA | Bovine Serum Albumin |
| EDTA | Ethylene Diamine Tetraacetic Acid |

Methods of Preparation

Another aspect of the present invention provides a process for preparing a compound of formula I or salt thereof.

Throughout the following description of such processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis," T. W. Green, P. G. M. Wuts, Wiley-Interscience, New York, 1999.

Throughout the following description of such processes it is to be understood that cross-couplings can be performed in a manner that will be readily understood by one skilled in the art of organic synthesis. Conventional procedures for cross-coupling are described, for example, in "Organicmetallics in Syntheses", M. Schlosser (Ed.), John Wiley and Sons Unless specified otherwise, P, Q, $X^1$, $X^2$, $X^3$, $X^4$, $X^5$, R, $R^1$, $R^2$, $R^3$, $R^4$, $R^5$, $R^6$, $R^7$, $R^8$, $R^9$, G, $M^1$, $M^2$, $M^3$, m and n, are defined as in formula I.

All starting materials are commercially available or earlier described in the literature. $^1$H NMR spectra were recorded on Bruker 300 at 300 MHz. The mass spectra were recorded utilising electrospray (MS only using QTOF Global Micromass or LC-MS; LC:Waters 2790, column XTerra MS $C_8$ 2.5 µm 2.1×30 mm, buffer gradient $H_2O+0.1\%TFA:CH_3CN+0.04\%TFA$, MS: micromass ZMD) ionisation technique. Chem Elut Extraction Column (Varian, cat #1219–8002) and Mega BE-SI (Bond Elut Silica) SPE Columns (Varian, cat #12256018; 12256026; 12256034) were used during purification of the products.

Abbreviations:

| | |
|---|---|
| DMF | N,N-dimethylformamide |
| DMSO | dimethylsulfoxide |
| EDCI | 1-(3-dimethylaminopropyl)-3-ethylcarbodiimide hydrochloride |
| HOBt | 1-hydroxybenzotriazole hydrate |
| THF | tetrahydrofuran |
| TFA | trifluoroacetic acid |
| Et | ethyl |
| Ac | acetyl |
| DIBAL | diisobutylaluminum hydride |
| M, N | molar and normal |
| HBTU | O-Benzotriazol-1-yl-N,N,N',N'-tetramethyluronium hexafluorophosphate |
| Boc | tert-butoxycarbonyl |
| Cbz | benzyloxycarbonyl |
| MCPBA | meta-chloroperoxybenzoic acid |
| SPE | solid phase extraction |
| AIBN | 2,2'azobisisobutyronitrile |
| NBS | N-bromosuccinimide |
| DAST | (Diethyamino)sulfur trifluoride |

Synthesis of Nitriles and Acids for Use in Preparation of Compounds of Formula II & III:

Aryl nitrites are available by a variety of methods including cyanation of an aryl halide or triflate under palladium or nickel catalysis using an appropriate cyanide source such as zinc cyanide in an appropriate solvent such as N,N-dimethylformamide. The corresponding acid is available from the nitrile by hydrolysis under either acidic or basic conditions in an appropriate solvent such as aqueous alcohols. Aryl acids are also available from a variety of other sources, including iodo- or bromo-lithium exchange followed by trapping with $CO_2$ to give directly the acid.

The acid may be converted to the primary amide using any compatible method to activate the acid, including via the acid chloride or mixed anhydride, followed by trapping with any source of ammonia, including ammonium chloride in the presence of a suitable base, ammonium hydroxide, methanolic ammonia or ammonia in an aprotic solvent such as dioxane. This amide intermediate may be converted to the nitrile using a variety of dehydration reagents such as oxalyl chloride or thionyl chloride. This reaction sequence to convert an acid into a nitrile may also be applied to non-aromatic acids, including suitably protected amino acid derivatives. A suitable protecting group for an amine, in an amino acid or in a remote position of any other acid starting material, may be any group which removes the basicity and nucleophilicity of the amine functionality, including such carbamate protecting group as Boc.

Some acids are more easily prepared taking advantage of commercially available analogs. For example, 6-methylpyridine-4-carboxylic acid is prepared by dechlorination of 2-chloro-6-methylpyridine-4-carboxylic acid. Certain types of substituted fluoro-benzonitriles and benzoic acids are available from bromo-difluoro-benzene via displacement of one fluoro group with a suitable nucleophile such as imidazole in the presence of a base such as potassium carbonate in a compatible solvent such as N,N-dimethylformamide at elevated temperatures (80–120° C.) for extended periods of time. The bromo group may subsequently be elaborated into the acid or nitrile as above. 1,3-Disubsituted and 1,3,5-trisubstituted benzoic acids and benzonitriles may be prepared by taking advantage of readily available substituted isophthalic acid derivatives. Monohydrolysis of the diester allows selective reaction of the acid with a variety of reagents, most typically activating agents such as thionyl chloride, oxalyl chloride or isobutyl chloroformate and the like. From the activated acid, a number of products are available. In addition to the primary amide used to form the nitrile by dehydration as mentioned above, reduction to the hydroxymethyl analog may be carried out on the mixed anhydride or acid chloride using a variety of reducing agents such as sodium borohydride in a compatible solvent such as tetrahydrofuran. The hydroxymethyl derivative may be further reduced to the methyl analog using catalytic hydrogenation with an appropriate source of catalyst such as palladium on carbon in an appropriate solvent such as ethanol. The hydroxymethyl group may also be used in any reaction suitable for benzylic alcohols such as acylation, alkylation, transformation to halogen and the like. Halomethylbenzoic acids of this type may also be obtained from bromination of the methyl derivative when not commercially available. Ethers obtained by alkylation of the hydroxymethyl derivatives may also be obtained from the halomethylaryl benzoate derivatives by reaction with the appropriate alcohol using an appropriate base such as potassium carbonate or sodium hydroxide in an appropriate solvent such as tetrahydrofuran or the alcohol. When other substituents are present, these may also be employed in standard transformation reactions. Treatment of an aniline with acid and sodium nitrite may yield a diazonium salt, which may be transformed into a halide such as fluoride using tetrafluoroboric acid. Phenols react in the presence of a suitable base such as potassium carbonate with alkylating agents to form aromatic ethers.

Preparation of Starting Materials for Use in Introducing the $M_3$-$(G)_n$ Group of Formula I Aldehyde precursors are available from a variety of methods, including reaction of a carbanion such as an arylmagnesium in an appropriate solvent such as tetrahydrofuran or ether with N,N-dimethylformamide or other formyl transfer reagent; reduction of an aryl ester with DIBAL in a suitable solvent such as dichloromethane, tetrahydrofuran or toluene. Halomethyl heteroaromatic compounds not commercially available can be prepared by a number of text-book routes, including halogenation of a benzylic methyl group with a reagent such as N-halosuccinimides in the presence of a reagent such as AIBN using a suitable solvent such as carbon tetrachloride or benzene or conversion of an benzylic alcohol to a halogen as mentioned above.

General Syntheses of Compounds of Formula V

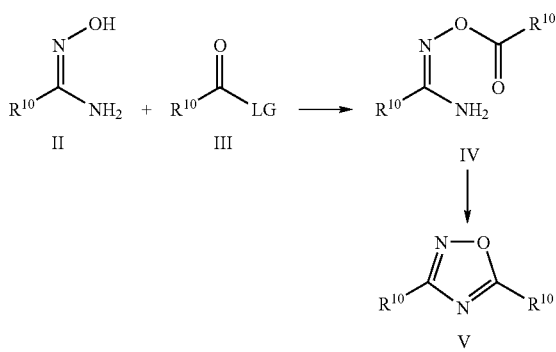

A compound of formula V, wherein $R^{10}$ is independently selected from a group consisting of $M_1(R^2)_n$—$P(R^1)_m$, $M_2(R^3)_n$—$Q(R^4)_m$—$M_3(R^5)_n$—$(G)_n$ and $M_2(R^3)_n$—$Q(R^4)_m$—Z ; Z is a recognized protecting group for $X^4$ when $X^4$ is N such as Boc, Cbz or benzyl, may be prepared through cyclization of compound of formula IV formed from a suitably activated is compound of formula III, wherein LG is a leaving group, with a compound of formula II. The compound of formula II may be prepared from a suitable nitrile by addition of hydroxylamine in a suitable solvent such as, methanol, ethanol, water or mixture thereof, using an appropriate base such as hydroxide, carbonate or acetate. The compound of formula III may be activated as follows; i) as the acid chloride formed from the acid using a suitable reagent such as oxalyl chloride or thionyl chloride; ii) as an anhydride or mixed anhydride formed from treatment with a reagent such as alkyl chloroformate; iii) using traditional methods to activate acids in amide coupling reactions such as EDCI with HOBt or uronium salts like HBTU; iv) as an alkyl ester when the hydroxyamidine is deprotonated using a strong base like sodium tert-butoxide or sodium hydride in a solvent such as ethanol or toluene at elevated temperatures (80–110° C.); v) by any other suitable method of activation for the desired substrate.

The ester formation to give intermediate IV may be accomplished using an appropriate aprotic solvent such as dichloromethane, tetrahydrofuran, N,N-dimethylformamide or toluene, with optionally an appropriate organic base such as triethylamine, diisopropylethylamine and the like or an inorganic base such sodium bicarbonate or potassium carbonate.

The cyclization of IV to form an oxadiazole may be carried out on the crude ester, with evaporation and replacement of the solvent with a higher boiling solvent such as DMF, or with aqueous extraction to provide a semi-purified material or with material purified by standard chromatographic methods. The cyclization may be accomplished by heating conventionally or by microwave irradiation (100–180° C.), in a suitable solvent such as pyridine or N,N-dimethylformamide or using a lower temperature method employing reagents like tetrabutylammonium fluoride in tetrahydrofuran or by any other suitable known literature method.

Further examples of the above described reactions can be found in Poulain et al., Tetrahedron Lett., 2001, 42, 1495–98, Ganglott et al., Tetrahedron Lett. 2001, 42, 1441–43, which are hereby incorporated by reference.

Introduction of $M_3(R^5)_n$—$(G)_n$ Group when $X^4$ is N:

When $R^{10}$ is $M_2(R^3)_n$—$Q(R^4)_m$—Z such that $X^4$ is N substituted with a protecting group Z, this group may be cleaved to reveal the secondary amine to allow subsequent reactions with the amine moiety. When Z=Boc, intermediates of formula V may be deprotected under any standard conditions for removal of an acid labile protecting group, including by treatment with trifluoroacetic acid in dichloromethane at room temperature or by treatment with neat formic acid at slighlty elevated temperatures (40–50° C.).

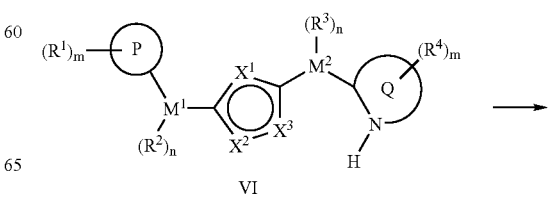

-continued

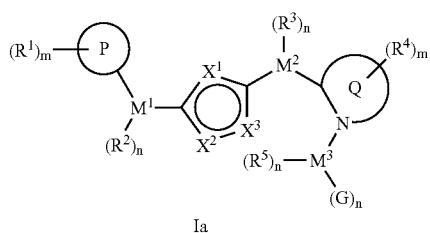
Ia

The secondary amines of formula VI thus formed may be substituted with a group $M^3(R^5)_n$—$(G)_n$ by a number of methods appropriate to the choice of $M^3$, $R^5$ and G. When M is C and $R^5$ and G are not excessively sterically hindered, several methods to introduce the substituent may be employed. One possibility is reductive amination with a reagent consisting of G—$C(R^5)$=O using an appropriate reducing agent such as Raney Nickel, sodium triacetoxyborohydride or sodium cyanoborohydride in an appropriate solvent such as 1,2-dichloroethane, methanol, tetrahydrofuran or toluene. Another possible method is direct alkylation of the secondary amine using an appropriate alkylaryl halide in the presence of a base such as triethylamine or potassium carbonate in a solvent such as acetonitrile or DMF at ambient or elevated temperatures.

The $M^3(R^5)_n$—$(G)_n$ group can also be introduced prior to cyclization to intermediate compound of formula Ib. In this case, the preferred method is using the conditions described in conditions iv) with compounds of formula VIII and IX wherein $X^5$ is selected from a group consisting of O, and N—OH, and $X^6$ is selected from the group consisting of $OC_{1-3}$alkyl and $NH_2$.

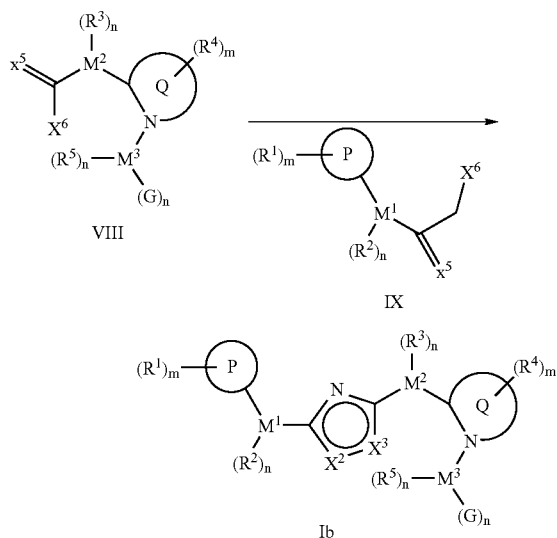

EXAMPLES

The following examples will now be illustrated by the following non-limiting examples.

Example 1

3-cyano-5-methoxybenzoic acid

A solution of dimethyl-5-hydroxyisophthalate (6 g, 28.6 mmol) and potassium carbonate (9 g, 65.4 mmol) in acetone (120 mL) was prepared. To this, methyl iodide (4 mL, 63.7 mmol) was added and the reaction was left stirring overnight at room temperature. The reaction mixture was filtered and then concentrated. The residue was dissolved in ethyl acetate and washed with water and brine, dried over anhydrous sodium sulfate, filtered and concentrated in vacuo to yield 6.4 g (quantitative) of dimethyl-5-methoxy-isophthalate as an off-white solid. $^1$H NMR (CDCl$_3$), δ(ppm): 8.28 (s, 1H), 7.75 (s, 2H), 3.95 (s, 6H), 3.90 (s, 3H).

A suspension of dimethyl-5-methoxy-isophthalate (6.4 g, 28.5 mmol) in methanol (143 mL) was treated with 1 N sodium hydroxide (25.6 mL, 25.6 mmol). The reaction was left stirring overnight at room temperature. After the solution was concentrated, the residue was dissolved in water and transferred to a separatory funnel. The aqueous layer was washed with dichloromethane (3 times) and then acidified with 1 N HCl to pH 2. Ethyl acetate was used to extract the precipitate, which was then washed with brine and dried over anhydrous sodium sulfate. After removal of solvent in vacuo, 4.5 g (75%) of 5-methoxyisophthalic acid monomethyl ester was isolated as a white solid. $^1$H NMR (DMSO), δ(ppm): 8.17 (m, 1H), 7.60 (m, 2H), 3.80 (s, 3H), 3.76 (s, 3H).

A suspension of 5-methoxyisophthalic acid monomethyl ester (4.5 mg, 21.3 mmol) in thionyl chloride (25 mL) was heated at reflux for 3 h. The excess thionyl chloride was then removed in vacuo and the intermediate acid chloride dissolved in dichloromethane (20 mL). After cooling to 0° C. the solution was treated with 0.5 M ammonia in 1,4-dioxane (102 mL) and then allowed to warm to room temperature. After 1.5 h of stirring the solvent was removed in vacuo and the residue was triturated with water. The precipitate was collected, washed with water and dried in vacuo to afford 4.0 g (90%) of 5-methoxy-isophthalamic acid methyl ester as an off-white solid. $^1$H NMR (CDCl$_3$), δ(ppm): 8.11 (s, 1H), 7.68 (m, 2H), 3.95 (s, 3H), 3.91 (s, 3H).

A suspension of 5-methoxy-isophthalamic acid methyl ester (4.0 g, 19.1 mmol) in a dichloromethane (80 mL) at 0° C. was treated with pyridine (6.3 mL, 77.0 mmol) and then trifluoroacetic anhydride drop-wise (6.5 mL, 46 mmol). The reaction was stirred at 0° C. for 20 min. and then stirred overnight at room temperature. The reaction mixture was washed with water, 1.0 N HCl and brine, dried over anhydrous sodium sulfate, filtered and concentrated to afford 3.6 g (98%) of 3-cyano-5-methoxy-benzoic acid methyl ester as a white solid.

A solution of 3-cyano-5-methoxy-benzoic acid methyl ester (3.4 g, 18.7 mmol) in THF (45 mL) was treated with 0.5 N lithium hydroxide (45 mL, 22.4 mmol). The reaction was stirred at 75° C. for 2 h and then the solvent was removed in vacuo. The residue was dissolved in a small amount of water and then acidified (pH 2) by the addition of 1 N HCl. Ethyl acetate was used to extract the precipitate, which was then washed with brine and dried over anhydrous sodium sulfate. After removal of solvent in vacuo, 2.5 g (77%) of 3-cyano-5-methoxybenzoic acid was isolated as a white solid. $^1$H NMR (DMSO), δ(ppm): 7.86 (s, 1H), 7.71 (m, 2H), 3.87 (s, 3H).

Example 2

3-Fluoro-5-cyano-(1H-imidazol-1-yl)-benzene

1-Bromo-3,5-difluorobenzene (1.00 g, 5.18 mmol) was dissolved in anhydrous DMF (10 mL). The solution was chilled in an ice bath. Imidazole (0.36 g, 5.18 mmol) and $K_2CO_3$ (0.72 g, 5.18 mmol) were added. The reaction mixture was stirred at room temperature for 16 h, and at 80° C. for 24 h. The reaction mixture was poured into water (100 mL) and extracted with EtOAc. The organic phase was washed with brine, dried ($MgSO_4$), filtered and concentrated. The intermediate 3-fluoro-5-bromo-(1H-imidazol-1-yl)-benzene was used directly in the next step.

A solution of 3-fluoro-5-bromo-(1H-imidazol-1-yl)-benzene in DMF (36 mL) was treated with zinc cyanide and tetrakis(triphenylphosphine)palladium(0). The reaction mixture was heated under an argon atmosphere for 18 h at 80° C. when GC-MS indicated complete disappearance of starting bromide and presence of product molecular ion ($M^+$ 187). The reaction mixture was partitioned between ethyl acetate and water, filtered to remove insoluble material, and the layers obtained in the filtrate were separated. The organic layer was washed with brine, dried over magnesium sulfate and concentrated in vacuo. 3-Fluoro-5-cyano-(1H-imidazol-1-yl)-benzene was obtained as a colourless solid and used without further purification.

Example 3

2-Cyano-piperidine-1-carboxylic acid tert-butyl ester

Piperidine-1,2-dicarboxylic acid-1-tert-butyl ester (12.8 g, 55.6 mmol) and THF (170 mL) were added to a 500 mL round bottom flask equipped with stir bar. The solution was cooled to −20° C. and triethylamine (10.1 mL, 72.3 mmol) was added followed by ethyl chloroformate (5.32 mL, 55.6 mmol). The resulting white precipitate was left stirring at −10° C. for 1 h. Aqueous ammonia (22.6 mL, 1168 mmol) was added to the above reaction mixture and the clear reaction mixture was stirred at room temperature overnight. The reaction mixture was concentrated in vacuo and the isolated residue was dissolved in ethyl acetate (300 mL). The organic phase was successively washed with water (300 mL) and brine (200 mL), dried (sodium sulfate), filtered and concentrated in vacuo to isolate a clear gum. The gum was triturated with hexanes to isolate the title compound (9.4 g, 74%) as a white solid. $^1$H-NMR ($CDCl_3$), δ(ppm): 6.03 (bs, 1H), 5.55 (bs, 1H), 4.77 (bs, 1H), 4.05 (bs, 1H), 2.81 (t, 1H), 2.27 (bs, 1H), 1.47 (m, 14H).

Acetonitrile (220 mL) and DMF (3.82 mL, 49.4 mmol) were added to a 500 mL round bottom flask equipped with stir bar. Cooled the mixture down to −5° C. and to it added oxalyl chloride (24.7 mL, 49.4 mmol, 2 M dichloromethane). The resulting mixture was stirred for 15 min. This was followed by addition of solution of 2-carbamoyl-piperidine-1-carboxylic acid tert-butyl ester (9.4 g, 41.2 mmol) in acetonitrile (50 mL) and pyridine (8.3 mL, 103 mmol). Reaction mixture was left stirring at room temperature overnight. The reaction mixture was concentrated in vacuo and the residue was dissolved in ethyl acetate (300 mL). The organic phase was successively washed with water (300 mL) and brine (200 mL), dried (sodium sulfate), filtered and concentrated in vacuo to isolate the title compound (8.44 g, 97%) as a yellow solid. $^1$H-NMR ($CDCl_3$), δ(ppm): 5.23 (bs, 1H), 4.03 (bs, 1H), 2.93 (t, 1H), 1.75 (m, 5H), 1.46 (m, 10H).

Example 4

2-(N-Hydroxycarbamimidoyl)-piperidine-1-carboxylic acid tert-butyl ester

Hydroxylamine hydrochloride (13.2 g, 190 mmol), sodium carbonate (20.2 g, 190 mmol) and water (360 mL) were added to a 1000 mL round bottom flask, equipped with stir bar. To this stirred mixture was added a solution of 2-cyano-piperidine-1-carboxylic acid tert-butyl ester (8 g, 38 mmol) in ethyl alcohol (300 mL). The resulting reaction mixture was left stirring at 65° C. overnight. The reaction mixture was cooled to room temperature and concentrated in vacuo. The residue was dissolved in ethyl acetate (150 mL) and washed with water (300 mL). The separated aqueous phase was further extracted with ethyl acetate (3×150 mL). The combined organic phase was washed with brine (200 mL), dried (sodium sulfate), filtered and concentrated in vacuo. The crude residue was purified on silica gel using 50% ethyl acetate in hexanes to isolate the title compound (7.8 g, 85%) as a white solid. $^1$H-NMR ($CDCl_3$), δ(ppm): 8.40 (bs, 1H), 4.82 (bd, 3H), 3.97 (d, 1H), 2.74 (t, 1H), 2.09 (d, 1H), 1.56 (m, 14H).

Examples 5 to 7 were Prepared as Described for Example 4.

Example 5

N-Hydroxy-thiophene-2-carboxamidine

To an ethanol (5 mL) solution of 2-thiophenecarbonitrile (525.5 mg, 5 mmol), 5 M hydroxylamine hydrochloride (1.1 mL) and 1 M sodium hydroxide (5.5 mL) were added. After the reaction mixture was heated at 80° C. for 3 h, water and dichloromethane were added. The organic layer was dried, concentrated and triturated with hexanes to give a white solid 625.8 mg (88%). $^1$H NMR (DMSO-$d_6$), δ(ppm): 9.6 (s, 1H), 7.46 (m, 2H), 7.05 (t, 1H), 5.93 (bs, 2H).

Example 6

3-Ethyl-N-hydroxy-benzamidine

3-Ethyl-benzonitrile (400 mg, 3.05 mmol) with 5 M hydroxylamine hydrochloride (0.61 mL) and 1 M sodium hydroxide (3.05 mL) in ethanol (3 mL) were stirred at room temperature for 60 h. Work up as in example 4 afforded 230 mg (46%) of 3-ethyl-N-hydroxy-benzamidine.

Example 7

3-Fluoro-5-(1H-imidazol-1-yl)phenyl-amidoxime

3-Fluoro-5-(1H-imidazol-1-yl)benzonitrile (950 mg, 5.08 mmol) and 5 M hydroxylamine hydrochloride (1.02 mL, 5.08 mmol) in ethanol (5 mL) and 1 N sodium hydroxide (5.08 mL, 5.08 mmol) were heated at reflux for 1 hour and 20 min. Work up as in example 4 afforded 901 mg (81.4%) of 3-bromo-5-fluorophenylamidoxime.

Example 8

5-Methyl-pyridine-2-carbaldehyde

To the 0.25 M 5-methyl-2-pyridinylmagnesium bromide of THF solution (20 mL, 5 mmol), DMF (0.773 mL, 10 mmol) was added at room temperature under argon. The reaction mixture was stirred for 10 min. and concentrated in vacuo. The residue was quenched with saturated ammonium chloride and dichloromethane. The organic layer was dried and the product was purified by silica gel column chromatography with 20% ethyl acetate in hexanes to give 379 mg (62.6%) of the title compound. GC-MS (M+): 121.

Examples 9 to 10 were prepared as described for Example 8.

Example 9

4-Methyl-pyridine-2-carbaldehyde

4-Methyl-pyridine-2-carbaldehyde (433 mg, 71.5%) was obtained from 0.25 M 4-methyl-2-pyridinylmagnesium bromide of THF solution (20 mL, 5 mmol) with DMF (0.773 mL, 10 mmol) at room temperature under argon.

Example 10

3-Methyl-pyridine-2-carbaldehyde

3-Methyl-pyridine-2-carbaldehyde (200 mg, 33.0%) was obtained from 0.25 M 3-methyl-2-pyridinylmagnesium bromide of THF solution (20 mL, 5 mmol) with DMF (0.773 mL, 10 mmol) at room temperature under argon.

Example 11

5-Fluoro-pyridine-2-carbaldehyde

5-Fluoro-pyridine-2-carboxylic acid (200 mg, 1.13 mmol) was mixed with ethanol (6 mL) and 4 M HCl in dioxane (0.5 mL) at 90° C. for 20 h. The mixture was concentrated and mixed with saturated sodium carbonate and dichloromethane. The dichloromethane layer was washed with brine, dried to give 94 mg (49.3%) of 5-fluoro-pyridine-2-carboxylic acid ethyl ester.

To 5-fluoro-pyridine-2-carboxylic acid ethyl ester (94 mg, 0.556 mmol) in dichloromethane (4.0 mL), 1 M DIBAL in toluene (1.23 mL, 1.23 mmol) was added at room temperature and the mixture was stirred for 30 min. The reaction mixture was quenched with 2 M sodium carbonate and extracted with dichloromethane. The dichloromethane was dried and concentrated to give 39 mg (54.7%) of crude 5-fluoro-pyridine-2-carbaldehyde which could be used for the next step reaction without further purification. GC-MS (M+): 125

Example 12

5-Chloro-pyridine-2-carbaldehyde

5-Chloro-pyridine-2-carboxylic acid ethyl ester (146 mg, 76.3%) was obtained obtained as described in Example 11 from 5-chloro-pyridine-2-carboxylic acid (200 mg, 1.03 mmol) with ethanol (3 mL) and 4M HCl in dioxane (0.5 mL) at 90° C. for 20 h. 5-Chloro-pyridine-2-carbaldehyde (58 mg, 52%) was obtained as described in Example 11 from 5-chloro-pyridine-2-carboxylic acid ethyl ester (146 mg, 0.786 mmol) with 1 M DIBAL in toluene (1.74 mL, 1.74 mmol) in dichloromethane (4.0 mL) 20 min. GC-MS (M+): 141

Example 13

3-Chloromethyl-5-methyl-[1,2,4]oxadiazole

2-Chloro-N-hydroxy-acetamidine (217 mg, 2 mmol) was mixed with acetic anhydride (224.4 mg, 2.2 mmol) in dichloromethane (2 mL) at room temperature for 1 hour. Then DMF (1 mL) was added in and the reaction mixture was heated at 130° C. for 2 h. The reaction was quenched with saturated sodium carbonate and extracted with ethyl acetate. The organic layer was dried and concentrated to give 59 mg (22.2%) of the title compounds as a crude yellow oil, which could be used for the next step reaction without further purification. $^1$H NMR (CDCl$_3$), δ(ppm): 4.51 (s, 2H), 2.55 (s, 3H).

Example 14

1-Pyridin-2-ylmethyl-piperidine-2-carboxylic acid methyl ester

Methyl pipecolinate hydrochloride (9.0 g, 50 mmol) was mixed with pyridine-2-carbaldehyde (5.4 g, 50 mmol) and triethylamine (5.05 g, 50 mmol) in dichloroethane (180 mL) at room temperature. Sodium triacetoxyborohydride (14.8 g, 70 mmol) was added in one portion. After the reaction mixture was stirred at room temperature for 1.5 h, saturated sodium carbonate was added. Then the mixture was extracted with ethyl acetate. The organic layer was washed with brine, dried with sodium sulfate, filtered and concentrated to give 10.9 g (93.6%) of the title compound as a pale brown oil. $^1$H NMR (CDCl$_3$), δ(ppm): 8.53 (d, 1H), 7.65 (td, 1H), 7.49 (d, 1H), 7.14 (t, 1H), 3.89 (d, 1H), 3.73 (s, 3H), 3.68 (d, 1H), 3.25 (dd, 1H), 2.97 (m, 1H), 2.25 (m, 1H), 1.85 (m, 2H), 1.30-1.76(m, 4H).

Example 15

(S)-1-Pyridin-2-ylmethyl-piperidine-2-carboxylic acid methyl ester (S)-1-Pyridin-2-ylmethyl-piperidine-2-carboxylic acid methyl ester (2.25 g, 100%) was obtained as described in Example 14 from (S)-methyl pipecolinate hydrochloride (1.68 g, 9.37 mmol) reacted with pyridine-2-carbaldehyde (1.0 g, 9.37 mmol) and sodium triacetoxyborohydride (2.78 g, 13.1 mmol) in triethylamine (946 mg, 9.37 mmol) in dichloroethane (20 mL) at room temperature. $^1$H NMR (CDCl$_3$), δ(ppm): 8.53 (d, 1H), 7.65 (td, 1H), 7.49 (d, 1H), 7.14 (t, 1H), 3.89 (d, 1H), 3.73 (s, 3H), 3.68 (d, 1H), 3.25 (dd, 1H), 2.97 (m, 1H), 2.25 (m, 1H), 1.85 (m, 2H), 1.30–1.76 (m, 4H).

Example 16

6-Methyl-piperidine-2-carboxylic acid

6-Methyl-pyridine-2-carboxylic acid (4.11 g, 30 mmol) was mixed with platinum(IV) oxide (35 mg, 0.154 mmol) in ethanol (50 mL) and water (25 mL) and stirred under hydrogen for 3 days. The reaction mixture was filtered through the celite and concentrated to dry. The residue was triturated with diethyl ether to give 4.1 g (98.3%) of the title compound as a white solid. $^1$H NMR (CDCl$_3$), δ(ppm): 3.39 (dd,1H), 3.11 (m, 1H), 2.28 (d, 1H), 1.88 (m, 2H), 1.35–1.67 (m, 3H), 1.32 (d, 3H).

Example 17

4-Hydroxy-piperidine-2-carboxylic acid methyl ester

To a solution of 4-bromobutene (5.0 g, 37.0 mmol) in THF (50 mL) was added potassium carbonate (10.2 g, 74.0 mmol) followed by benzylamine (4.0 g, 37.0 mmol). The resulting mixture was then heated to 70° C. for 16 h. On cooling to room temperature, ethyl acetate was added followed by washing with water. The organic extract was then washed with brine and dried over MgSO$_4$ (anhydrous) and the solvent was removed in vacuo. The residue was then purified by flash column silica gel chromatography with ethyl acetate as eluant affording 3.1 g (52%) of the product as a light yellow oil. $^1$H-NMR (CDCl$_3$), δ(ppm): 7.30 (m, 5H), 5.81 (m, 1H), 5.10 (m, 2H), 3.82 (s, 2H), 2.72 (t, 2H), 2.37 (m, 2H), To a solution of benzyl-but-3-enyl-amine (3.1 g, 19.2 mmol) in acetonitrile (50 mL) and water (50 mL) was added glyoxalic acid monohydrate (1.94 g, 21.1 mmol). The resulting solution was allowed to stir at room temperature for 24 h. The mixture was then concentrated in vacuo and the aqueous residue was made basic with 1 N NaOH and the product was extracted with CH$_2$Cl$_2$. The organic extract was then washed with brine and dried over MgSO$_4$ (anhydrous) and the solvent was removed in vacuo to give 3.0 g (72%) of the crude residue as a light yellow oil. $^1$H-NMR (CDCl$_3$), δ(ppm): 7.30 (m, 5H), 4.82 (t, 1H), 3.71 (d, 1H), 3.61 (d, 1H), 3.29 (d, 1H), 3.02 (dd, 1H), 2.46 (dt, 1H), 2.24 (m, 1H), 2.05–1.80 (m, 3H).

To a solution of the crude residue in methanol under argon was added 10% Pd/C and the mixture was hydrogenated at 50 psi of hydrogen for 24 h. The mixture was then filtered through celite and the filtrate was concentrated in vacuo to give the title compound as a colourless oil (2.2 g, 100%). $^1$H-NMR (CDCl$_3$), δ(ppm): 3.75 (s, 3H), 3.74 (m, 1H), 3.34 (dd, 1H), 3.18 (td, 1H), 2.62 (dt, 1H), 2.29 (m, 1H), 1.92 (m, 1H), 1.83 (br, 2H), 1.38 (m, 2H).

Example 18

Piperidine-1,2-dicarboxylic acid-1-tert-butyl ester

A solution of DL-pipecolinic acid (13 g, 100 mmol), potassium carbonate (55.2 g, 400 mmol), di-tert-butyl dicarbonate (28.4 g, 130 mmol) in acetone (30 mL) and water (100 mL) was stirred at room temperature overnight. The reaction mixture was brought to pH 3 using hydrochloric acid (1 N aqueous) and then extracted with ethyl acetate (350 mL). The organic phase was separated, sequentially washed with water (200 mL) and brine (200 mL), dried (sodium sulfate), filtered and concentrated in vacuo. The isolated solid was triturated with hexanes to yield 22.7 g (99%) of the title compound as a white solid. $^1$H-NMR (CDCl$_3$), δ(ppm): 9.3 (bs, 1H), 4.84 (bd, 1H), 3.94 (m, 1H), 2.93 (m, 1H), 2.22 (m, 1H), 1.67 (m, 3H), 1.45 (m, 11H).

Examples 19 to 22 were prepared as described for Example 18.

Example 19

Pyrrolidine-1,2-dicarboxylic acid 1-tert-butyl ester

Pyrrolidine-1,2-dicarboxylic acid 1-tert-butyl ester (4.16 g, 22%) was obtained from pyrrolidine-2-carboxylic acid (10.0 g, 85.2 mmol) with di-tert-butyl dicarbonate (19 g, 87 mmol) and potassium carbonate (25.5 g, 185 mmol) in water (250 mL). Work up was carried out as in Example 18 and the product was used without further purification.

Example 20

6-Methyl-piperidine-1,2-dicarboxylic acid 1-tert-butyl ester

6-Methyl-piperidine-1,2-dicarboxylic acid 1-tert-butyl ester (2.3 g, 67.8%) was obtained from 6-methyl-piperidine-2-carboxylic acid (2.0 g, 14 mmol) with di-tert-butyl dicarbonate (3.98 g, 18.16 mmol) and potassium carbonate (7.71 g, 55.88 mmol) in acetone (5 mL) and water (20 mL). Work up was carried out as in Example 18 and the product was used without further purification. $^1$H NMR (CDCl$_3$), δ(ppm): 4.73 (d,1H), 4.32 (m, 1H), 2.28 (d, 1H), 1.45–1.70 (m & s, 14H), 1.13 (d, 3H)

Example 21

Morpholine-3,4-dicarboxylic acid-4-tert-butyl ester

Morpholine-3,4-dicarboxylic acid-4-tert-butyl ester (1.5 g, 85%, white solid) was obtained from DL-morpholine carboxylic acid (1.0 g, 7.6 mmol), potassium carbonate (5.5 g, 39.8 mmol), di-tert-butyl dicarbonate (2.5 g, 11.4 mmol) in acetone (30 mL) and water (100 mL). Work up was carried out as in Example 18 and the product was used without further purification. The solid was triturated with 30% ethyl acetate in hexanes. $^1$H-NMR (CDCl$_3$), δ(ppm): 8.18 (br, 1H), 4.55 (d, 1H), 4.40 (dd, 1H), 3.89 (dd, 1H), 3.73 (dd, 1H), 3.66 (dd, 1H), 3.48 (m, 1H), 3.32 (m, 1H), 1.45 (s, 9H).

Example 22

4-Hydroxy-piperidine-1,2-dicarboxylic acid 1-tert-butyl ester 2-methyl ester

4-Hydroxy-piperidine-1,2-dicarboxylic acid 1-tert-butyl ester 2-methyl ester (3.1 g, 87%) was obtained from 4-hydroxy-piperidine-2-carboxylic acid methyl ester (2.2 g, 13.8 mmol) in dioxane (40 mL) and water (20 mL) at 0° C. with triethylamine (4.2 g, 40.2 mmol) and di-tert-butyl dicarbonate (4.5 g, 20.6 mmol). Work up was carried out as in Example 18 and the product was used without further purification.

Example 23

4-Oxo-piperidine-1,2-dicarboxylic acid 1-tert-butyl ester 2-methyl ester

To a mixture of oxalyl chloride ((15 mL, 30 mmol, 2 M dichloromethane) in CH$_2$Cl$_2$ (100 mL) cooled to −78° C. was added DMSO (4.5 mL, 63.4 mmol). The mixture was stirred at this temperature for 1 h, after which 4-hydroxy-piperidine-1,2-dicarboxylic acid 1-tert-butyl ester 2-methyl ester (2.0 g, 7.71 mmol dissolved in CH$_2$Cl$_2$) as added. The mixture stirred for a further 1 h and Et₃N (20 mL) was then added and the mixture stirred for another 30 min. The mixture was then allowed to warm to −40° C. and poured into a solution of 10% NaHSO₄. The reaction mixture was then extracted with ethyl acetate. The organic extract was then washed with brine and dried over MgSO4 (anhydrous) and the solvent was removed in vacuo and the crude residue was purified by silica gel flash column chromatography giving 1.75 g (88%) of the product as a yellow oil. $^1$H-NMR (CDCl₃), δ(ppm): 4.85 (br, d, 1H), 4.02 (m, 1H), 3.61 (s, 3H), 3.58 (br, 1H), 2.75 (m, 2H), 2.44 (br, 2H), 1.43 (br, s, 9H).

Example 24

4,4-Difluoro-piperidine-1,2-dicarboxylic acid 1-tert-butyl ester

4-Oxo-piperidine-1,2-dicarboxylic acid 1-tert-butyl ester (0.83 g, 3.4 mmol) was prepared as described for Example 23 by mixing with DAST (1.1 g, 6.8 mmol) in THF under argon at −70° C. The reaction mixture was slowly warmed to −20° C. and concentrated in vacuo. The residue was quenched with water and extracted with dichloromethane. The organic layer was washed with brine, dried to give 0.86 g (95%) of the title product as a yellow oil which was used without further purification.

Example 25

2-[3-(3-Cyano-phenyl)-[1,2,4]oxadiazol-5-yl]-piperidine-1-carboxylic acid tert-butyl ester To a mixture of piperidine-1,2-dicarboxylic acid 1-tert-butyl ester (5.32 g, 23.2 mmol) and triethylamine (4.04 g, 40 mmol) in THF (50 mL), isobutyl chloroformate (3.0 mL, 25.5 mmol) was added dropwise. After the mixture was stirred at room temperature for 45 min, 3-cyano-N-hydroxybenzamidine (3.7 g, 23.2 mmol) and DMF (40 mL) were added. After being stirred for another hour, the reaction mixture was heated to 130~135° C. for 1.5 h. Then the solution was cooled to room temperature and poured into water. Dichloromethane was used to extract the product. The organic layer was dried with sodium sulfate and concentrated in vacuo to give 8.1 g (98.4%) of the title compound as a thick brown oil.

Example 26

2-[3-(3-Cyano-phenyl)-[1,2,4]oxadiazol-5-yl]-6-methyl-piperidine-1-carboxylic acid tert-butyl ester 2-[3-(3-Cyano-phenyl)-[1,2,4]oxadiazol-5-yl]-6-methyl-piperidine-1-carboxylic acid tert-butyl ester (340 mg, 46.2%) was prepared according to the procedure in Example 25 from 6-methyl-piperidine-1,2-dicarboxylic acid 1-tert-butyl ester (486 mg, 2 mmol) with isobutyl chloroformate (273.16 mg, 2.0 mmol) and triethylamine (1.14 g, 8 mmol) in THF (6 mL). Then 3-cyano-N-hydroxy-benzamidine (306 mg, 1.9 mmol) and DMF (5 mL) were added and the mixture was heated at 130~135° C. for 3 h. $^1$H NMR (CDCl₃), δ(ppm): 8.38 (d, 1H), 8.32 (dd, 1H), 7.77 (dd, 1H), 7.61 (t, 1H), 5.58 (d, 1H), 4.43 (m, 1H), 2.55 (m, 1H), 1.50–1.98 (m & s, 14H), 0.96 (d, 3H).

Example 27

3-[3-(3-Cyano-phenyl)-[1,2,4]oxadiazol-5-yl]-morpholine-4-carboxylic acid tert-butyl ester Isobutylchloroformate (166 mg, 1.23 mmol), Et₃N (0.3 mL, 2.2 mmol) and morpholine-3,4-dicarboxylic acid-4-tert-butyl ester (189 mg, 0.82 mmol) in THF (5 mL) were stirred at room temperature for 3 h. 3-Cyano-N-hydroxybenzamidine (132 mg, 0.82 mmol) was added and the resulting mixture was stirred overnight at room temperature. The mixture was partitioned between ethyl acetate and water, and the organic extracts were washed with brine and dried over magnesium sulfate. Flash chromatography on silica gel using ethyl acetate in hexane yielded 182 mg (59%) of the acyclic intermediate as a colorless oil. A solution of the intermediate (182 mg, 0.49 mmol) in DMF (2 mL) was heated at 127° C. for 5 h. The mixture was partitioned between ethyl acetate and water, and the organic extracts were washed with brine and dried over magnesium sulfate. Flash chromatography on silica gel using ethyl acetate in hexane yielded 144 mg (82%) of the title compound as a colorless oil. $^1$H-NMR (CDCl₃), δ(ppm): 8.42 (s, 1H), 8.29 (d, 1H), 7.76 (dd, 1H), 7.57 (dd, 1H), 5.30 (br, d, 1H), 4.45 (m, 1H), 3.86 (m, 3H), 3.56 (t, 1H),3.45 (m, 1H), 1.45 (s, 9H).

Example 28

2-[5-(3-Cyano-phenyl)-[1,2,4]oxadiazol-3-yl]-piperidine-1-caboxylic acid tert-butyl ester In a 50 mL round bottom flask equipped with stir bar, added 2-(N-hydroxycarbamimidoyl)-piperidine-1-carboxylic acid tert-butyl ester (327 mg, 1.34 mmol), dichloromethane (5 mL) and triethylamine (0.56 mL, 4.03 mmol). To this stirred mixture was added a solution of 3-cyanobenzoyl chloride (222 mg, 1.34 mmol) in dichloromethane (3 mL). The resulting reaction mixture was stirred at room temperature for 2 h. DMF (5 mL) was added to the reaction mixture and stirred at 120° C. for 2 h. The reaction mixture was cooled to room temperature and diluted with ethyl acetate (50 mL). The organic phase was successively washed with water (30 mL) and brine (20 mL), dried (sodium sulfate), filtered and concentrated in vacuo. The crude residue was purified on silica gel using 20% ethyl acetate in hexanes to isolate 106 mg of the title compound as a white solid. $^1$H-NMR (CDCl₃), δ(ppm): 8.42 (s, 1H), 8.35 (d, 1H), 7.86 (dd, 1H), 7.67 (t, 1H), 5.56 (bs, 1H), 4.11 (bd, 1H), 3.04 (bs, 1H), 2.32 (d, 1H), 1.97 (m, 1H), 1.69 (t, 1H), 1.48 (m, 12H).

Example 29

2-[5-(3-Methoxy-phenyl)-[1,2,4]oxadiazol-3-yl]-piperidine-1-caboxylic acid tert-butyl ester 2-[5-(3-Methoxy-phenyl)-[1,2,4]oxadiazol-3-yl]-piperidine-1-caboxylic acid tert-butyl ester (220 mg, 75%, clear oil) was obtained as described for Example 28 from 2-(N-hydroxycarbamimidoyl)-piperidine-1-carboxylic acid tert-butyl ester (200 mg, 0.82 mmol) and 3-methoxybenzoyl chloride (0.12 mL, 0.82 mmol). $^1$H-NMR (CDCl₃), δ(ppm): 7.63 (d, 1H), 7.53 (bs, 1H), 7.33 (t, 1H), 7.03 (dd, 1H), 5.48 (bs, 1H), 4.11 (m, 1H), 3.78 (s, 3H), 2.97 (bs, 1H), 2.26 (bd, 1H), 1.82 (m, 1H), 1.59 (m, 2H), 1.46 (m, 11H).

Example 30

2-[5-(3-Cyano-5-methoxy-phenyl)-[1,2,4]oxadiazol-3-yl]-piperidine-1-carboxylic acid tert-butyl ester DMF (2.0 mL) was added to a mixture of cyano-5-methoxybenzoic acid (160 mg, 0.90 mmol), EDCI (176 mg, 0.92 mmol), HOBt (124.3 mg, 0.92 mmol) and 2-(N-hydroxycarbamimidoyl)-piperidine-1-carboxylic acid tert-butyl ester (224 mg, 0.92 mmol) at room temperature and stirred overnight. The reaction mixture was diluted with ethyl acetate, washed with water (3 times) and brine, dried anhydrous sodium sulfate, filtered and concentrated. DMF (3 mL) was added to the residue and then heated 135° C. for 2.5 h to effect cyclization to oxadiazole. The reaction mixture was diluted with ethyl acetate, washed with water (3 times) and brine, dried over anhydrous sodium sulfate, filtered, and concentrated. Purification by flash chromatography on silica gel, eluted with a mixture of ethyl acetate in hexanes afforded 179 mg (56%) of the title compound as a colorless oil. $^1$H NMR (CDCl$_3$), δ(ppm): 7.99 (s, 1H), 7.84 (d, 1H), 7.35 (s, 1H), 5.56 (bs, 1H), 4.06 (m, 1H), 3.93 (s, 3H), 3.01 (m, 1H), 2.84 (m, 1H), 1.92 (m, 1H), 1.70 (m, 2H), 1.49 (m, 11H).

Examples 31 to 33 were prepared as described for Example 30.

Example 31

2-(5-m-Tolyl-[1,2,4]oxadiazol-3-yl)-piperidine-1-carboxylic acid tert-butyl ester 2-(5-m-Tolyl-[1,2,4]oxadiazol-3-yl)-piperidine-1-carboxylic acid tert-butyl ester (194 mg, yellow oil) was obtained from 2-(N-hydroxycarbamimidoyl)-piperidine-1-carboxylic acid tert-butyl ester (200 mg, 0.82 mmol), EDCI (158 mg, 0.82 mmol), HOBt (111 mg, 0.82 mmol) and 3-methyl benzoic acid (102 mg, 0.75 mmol) in DMF (2 mL) and then heated in DMF (2 mL) at 120° C. overnight.

Example 32

2-[3-(3-Cyano-phenyl)-[1,2,4]oxadiazol-5-yl]-4,4-difluoro-piperidine-1-carboxylic acid tert-butyl ester 2-[3-(3-Cyano-phenyl)-[1,2,4]oxadiazol-5-yl]-4,4-difluoro-piperidine-1-carboxylic acid (440 mg, 34.8%) was obtained from 4,4-difluoro-piperidine-1,2-dicarboxylic acid 1-tert-butyl ester (0.86 g, 3.2 mmol), 3-cyano-N-hydroxy-benzamidine (547 mg, 3.4 mmol), EDCI (649 mg, 3.4 mmol) and HOBt (459 mg, 3.4 mmol) in DMF (5 mL). The second step was carried out at 130° C. for 6 h in DMF (5mL).

Example 33

2-[3-(3-Cyano-phenyl)-[1,2,4]oxadiazol-5-yl]-pyrrolidine-1-carboxylic acid tert-butyl ester 2-[3-(3-Cyano-phenyl)-[1,2,4]oxadiazol-5-yl]-pyrrolidine-1-carboxylic acid tert-butyl ester (240 mg, 29%) was obtained from pyrrolidine-1,2-dicarboxylic acid 1-tert-butyl ester (523.7 mg, 2.43 mmol), 3-cyano-N-hydroxy-benzamidine (393 mg, 2.44 mmol), EDCI (467 mg, 2.44 mmol) and HOBt (335 mg, 2.48 mmol) in DMF (6 mL). The second step was carried out at 120° C. for 24 h in DMF (5 mL).

Work up was carried out as in Example 30, with flash purification of the title compound on silica with a mixture of ethyl acetate in dichloromethane and hexane. $^1$H-NMR (CDCl$_3$), δ(ppm): 8.38 (br s, 1H), 8.31 (d, 1H), 7.78 (m, 1H), 7.61 (m, 1H), 5.2+5.08 (2-m rotomers, 1H), 3.4–3.8 (2-m, 2H), 2.4 (m, 1H), 2.0–2.2 (m, 3H), 1.47+1.29 (2-s, 9H).

Example 34

3-(5-Piperidin-2-yl-[1,2,4]oxadiazol-3-yl)-benzonitrile

2-[3-(3-Cyano-phenyl)-[1,2,4]oxadiazol-5-yl]-piperidine-1-carboxylic acid tert-butyl ester (8.1 g) was mixed with 96% formic acid (80 mL) and heated at 45° C. for 1 h. The reaction mixture was concentrated in vacuo. The residue was quenched with saturated sodium bicarbonate and extracted with dichloromethane. The organic layer was dried with sodium sulfate and concentrated again. The residue was triturated with hexanes to give 4.5 g (73.4%) of the title compounds as a white solid. $^1$H NMR (CDCl$_3$), δ(ppm): 8.41 (s, 1H), 8.33 (d, 1H), 7.78 (dd, 1H), 7.61 (t, 1H), 4.15 (dd, 1H), 3.20 (m, 1H), 2.84 (m, 1H), 2.14 (m, 1H), 1.55–2.00 (m, 5H).

Examples 35 to 38 were prepared as described for Example 34.

Example 35

3-(3-Piperidin-2-yl-[1,2,4]oxadiazol-5-yl)-benzonitrile 3-(3-Piperidin-2-yl-[1,2,4]oxadiazol-5-yl)-benzonitrile (70 mg, yellow oil) was obtained from 2-[5-(3-cyano-phenyl)-[1,2,4]oxadiazol-3-yl]-piperidine-1-caboxylic acid tert-butyl ester (100 mg, 0.28 mmol) and 98% formic acid (3 mL) at 45° C.

Example 36

2-[5-(3-Methoxy-phenyl)-[1,2,4]oxadiazol-3-yl]-piperidine

2-[5-(3-Methoxy-phenyl)-[1,2,4]oxadiazol-3-yl]-piperidine (131 mg, 83%, yellow oil) was obtained from 2-[5-(3-methoxy-phenyl)-[1,2,4]oxadiazol-3-yl]-piperidine-1-caboxylic acid tert-butyl ester (220 mg, 0.61 mmol) and 98% formic acid (3 mL) at 45° C.

Example 37

3-[5-(4,4-Difluoro-piperidin-2-yl)-[1,2,4]oxadiazol-3-yl]-benzonitrile

3-[5-(4,4-Difluoro-piperidin-2-yl)-[1,2,4]oxadiazol-3-yl]-benzonitrile (90 mg, 27.5%) was obtained from 2-[3-(3-cyano-phenyl)-[1,2,4]oxadiazol-5-yl]-4,4-difluoro-piperidine-1-carboxylic acid tert-butyl ester (440 mg, 1.13 mmol) with 96% formic acid (4.5 mL) at 45° C. $^1$H NMR (CDCl$_3$), δ(ppm): 8.36 (s, 1H), 8.29 (d, 1H), 7.77 (dd, 1H), 7.60 (t, 1H), 4.32 (dd, 1H), 3.30 (m, 1H), 3.02 (td, 1H), 2.59 (m, 1H), 1.85–2.30 (m, 4H), LC-MS MH$^+$:2.91.

Example 38

3-[5-(6-Methyl-piperidin-2-yl)-[1,2,4]oxadiazol-3-yl]-benzonitrile hydrochloride 3-[5-(6-Methyl-piperidin-2-yl)-[1,2,4]oxadiazol-3-yl]-benzonitrile hudrochloride (257 mg, 91%) was obtained from 2-[3-(3-cyano-phenyl)-[1,2,4]oxadiazol-5-yl]-6-methyl-piperidine-1-carboxylic acid tert-butyl ester (340 mg, 0.923 mmol) with 96% formic acid (3.5 mL) at 45° C. and then treated with 1 M hydrochloric acid in ether (1 mL). $^1$H NMR (CDCl$_{3+DMSO-d6}$), δ(ppm): 11.10 (bs, 1H), 10.08 (bs, 1H), 8.39 (s, 1H), 8.35 (d, 1H), 7.83 (d, 1H), 7.65 (t, 1H), 4.59 (t, 1H), 3.40(m, 1H), 2.37 (d, 1H), 2.10 (m, 2H), 1.85 (m, 3H), 1.58 (d, 3H).

Example 39

3-Methoxy-5-[3-(1-pyridin-2-ylmethyl-piperidin-2-yl)-[1,2,4]oxadiazol-5-yl]-benzonitrile To a solution of 2-[5-(3-cyano-5-methoxy-phenyl)-[1,2,4]oxadiazol-3-yl]-piperidine-1-carboxylic acid tert-butyl ester (162 mg, 0.42 mmol) in dichloromethane (4 mL) cooling in an ice-bath was added trifluoroacetic acid (2 mL). The ice-bath was removed after 30 min. and then left stirring for an additional hour. After the solvent was removed in vacuo, the residue was dissolved in ethyl acetate and then washed with saturated sodium bicarbonate, dried over anhydrous sodium sulfate, filtered and concentrated in vacuo 113 mg (94%) of the title compound as a white solid. $^1$H NMR (CDCl$_3$), δ(ppm): 7.99 (s, 1H), 7.84 (d, 1H), 7.35 (s, 1H), 5.56 (bs, 1H), 4.06 (m 1H), 3.93 (s, 3H), 3.01 (m, 1H), 2.84 (m, 1H), 1.92 (m, 1H), 1.70 (m, 2H), 1.49 (m 1H).

Examples 40 to 42 were prepared as described for Example 39.

Example 40

2-[5-m-Tolyl-[1,2,4]oxadiazol-3-yl]-piperidine

2-[5-m-Tolyl-[1,2,4]oxadiazol-3-yl]-piperidine (97.4 mg, as brown oil) was obtained from 2-(5-m-tolyl-[1,2,4]oxadiazol-3-yl)-piperidine-1-carboxylic acid tert-butyl ester (194 mg) in dichloromethane (4 mL) and trifluoroacetic acid (2 mL) at room temperature for 5 h.

Example 41

3-(5-Pyrrolidin-2-yl-[1,2,4]oxadiazol-3-yl)-benzonitrile 3-(5-Pyrrolidin-2-yl-[1,2,4]oxadiazol-3-yl)-benzonitrile (157.8 mg, 93%) was obtained from 2-[3-(3-cyano-phenyl)-[1,2,4]oxadiazol-5-yl]-pyrrolidine-1-carboxylic acid tert-butyl ester (239 mg, 0.70 mmol) in dichloromethane (5 mL) and trifluoroacetic acid (1 mL) at room temperature for 4 h. $^1$H-NMR (CDCl$_3$), δ(ppm): 8.40 (br s, 1H), 8.33 (d, 1H), 7.78 (d, 1H), 7.61 (t, 1H), 4.58 (m, 1H), 3.14 (m, 1H), 3.23 (m, 1H), 2.33 (m, 1H), 2.15 (m, 1H), 1.95 (m, 2H), 1.57 (br s, 1H).

Example 42

3-(5-Morpholin-3-yl-[1,2,4]oxadiazol-3-yl)-benzonitrile 3-(5-Morpholin-3-yl-[1,2,4]oxadiazol-3-yl)-benzonitrile (75 mg, 73%, colorless oil) was obtained from 3-[3-(3-cyano-phenyl)-[1,2,4]oxadiazol-5-yl]-morpholine-4-carboxylic acid tert-butyl ester (144 mg, 0.4 mmol) with trifluoroacetic acid (3 mL) in dichloromethane (3 mL) at 0° C. for 60 min. Purification was performed by flash column silica gel chromatography with 5% (2 M ammonia methanol) in dichloromethane. $^1$H-NMR (CDCl$_3$), δ(ppm): 8.37 (s, 1H), 8.30 (d, 1H), 7.77 (dd, 1H), 7.58 (dd, 1H), 4.32 (dd, 1H), 4.16 (dd, 1H), 3.95 (dd, 1H), 3.84 (dd, 1H),3.75 (m, 1H), 3.16 (m, 1H), 3.02 (m, 1H), 2.27 (br, 1H).

Example 43

3-[5-(1-Pyridin-2-ylmethyl-piperidin-2-yl)-1,2,4]oxadiazol-3-yl]-benzonitrile To the mixture of 3-(5-piperidin-2-yl-[1,2,4]oxadiazol-3-yl)-benzonitrile (50.8 mg, 0.2 mmol) and pyridine-2-carbaldehyde (42.8 mg, 0.4 mmol) in methanol (0.5 mL) and acetic acid (0.2 mL), 1 M sodium cyanoborohydride (0.2 mL, 0.2 mmol) was added. After 15 min, the reaction mixture was diluted with 2 M sodium carbonate and extracted with dichloromethane. The organic layer was dried with sodium sulfate and purified by column chromatography with 50/50 ethyl acetate/hexanes to give 47 mg (68%) of the title compound. $^1$H NMR (CDCl$_3$), δ(ppm): 8.48 (d, 1H), 8.39 (s, 1H), 8.32 (d, 1H), 7.77 (d, 1H), 7.62 (m,2H), 7.46 (d, 1H), 7.12 (t, 1H), 4.13 (t, 1H), 3.73 (q, 2H), 3.02 (m, 1H), 2.44 (m, 1H), 1.99–2.14 (m, 2H), 1.50–1.80 (m, 4H). LC-MS MH$^+$: 346.2

Examples 44 to 60 were prepared as described for Example 43.

Example 44

3-[3-(1-Pyridin-2-ylmethyl-piperidn-2-yl)-[1,2,4]oxadiazol-5-yl]-benzonitrile 3-[3-(1-Pyridin-2-ylmethyl-piperidn-2-yl)-[1,2,4]oxadiazol-5-yl]-benzonitrile (21.6 mg, 22%, clear oil) was obtained from 3-(3-piperidin-2-yl-[1,2,4]oxadiazol-5-yl)-benzonitrile (70 mg, 0.28 mmol) and pyridine-2-carbaldehyde (50 µL, 0.55 mmol) in methanol (1 mL) and acetic acid (0.28 mL) at 0° C. to room temperature with sodium cyanoborohydride (0.41 mL, 0.41 mmol, 1M THF). $^1$H-NMR (CDCl$_3$), δ(ppm): 8.46 (dd, 2H), 8.37 (dd, 1H), 7.85 (dd, 1H), 7.64 (m, 2H), 7.46 (d, 1H), 7.11 (dd,1H), 3.88 (dd, 1H), 3.80 (d, 1H), 3.52 (d, 1H), 3.01 (m, 1H), 2.30 (m, 1H), 1.99 (m, 3H), 1.69 (m, 2H), 1.42 (m, 1H). LC-MS$^+$ 346.2.

Example 45

3-[5-(1-Thiazol-2-ylmethyl-piperidin-2-yl)-j1,2,4]oxadiazol-3-yl]-benzonitrile 3-[5-(1-Thiazol-2-ylmethyl-piperidin-2-yl)-[1,2,4]oxadiazol-3-yl]-benzonitrile (61 mg, 86.9%) was obtained from 3-(5-piperidin-2-yl-[1,2,4]oxadiazol-3-yl)-benzonitrile (50.8 mg, 0.2 mmol) with thiazole-2-carbaldehyde (27.1 mg, 0.24 mmol) and sodium triacetoxyborohydride (59.3 mg, 0.28 mmol) and dichloroethane (1 mL) at room temperature for 2 h. $^1$H NMR (CDCl$_3$), δ(ppm): 8.40 (d, 1H), 8.32 (dd, 1H), 7.78 (m, 1H), 7.72 (d, 1H), 7.67 (t, 11H), 7.26 (d, 11H), 4.26 (t, 1H), 4.03 (t, 2H), 3.09 (m, 1H), 2.60 (m, 1H), 2.07 (m, 2H), 1.45–1.80 (m, 4H).

Example 46

3-{5-[1-(1-Methyl-1H-imidazol-2-ylmethyl)-piperidin-2yl]-[1,2,4]oxadiazol-3-yl}-benzonitrile 3-{5-[1-(1-Methyl-1H-imidazol-2-ylmethyl)-piperidin-2yl]-[1,2,4]oxadiazol-3-yl}-benzonitrile (49 mg, 70.4%) was obtained from 3-(5-piperidin-2-yl-[1,2,4]oxadiazol-3-benzonitrile (50.8 mg, 0.2 mmol) with 1-methyl-1H-imidazole-2-carbaldehyde (26.4 mg, 0.24 mmol) and sodium triacetoxyborohydride (59.3 mg, 0.28 mmol) and dichloroethane (1 mL) at room temperature for 2 h. $^1$H NMR (CDCl$_3$), δ(ppm): 8.39 (s, 1H), 8.32 (d, 1H), 7.80 (d, 1H), 7.61 (t, 1H), 6.87 (s, 1H), 6.82 (s, 1H), 3.96 (t, 1H), 3.75(s, 3H),3.67 (dd, 2H), 3.95 (m, 1H), 2.36 (m, 1H), 1.98 (m, 2H), 1.45–1.84 (m, 4H).

Example 47

3-{5-[1-(6-Methyl-pyridin-2-ylmethyl)-piperidin-2-yl]-[1,2,4]oxadiazol-3-yl}-benzonitrile 3-{5-[1-(6-Methyl-pyridin-2-ylmethyl)-piperidin-2-yl]-[1,2,4]oxadiazol-3-yl}-benzonitrile (55 mg, 76.6%) was obtained from 3-(5-piperidin-2-yl-[1,2,4]oxadiazol-3-yl)-benzonitrile (50.8 mg, 0.2 mmol) with 6-methyl-pyridine-2-carbaldehyde (29.04 mg, 0.24 mmol) and sodium triacetoxyborohydride (59.3 mg, 0.28 mmol) and dichloroethane (1 mL) at room temperature for 2 h. $^1$H NMR (CDCl$_3$), δ(ppm): 8.39 (s, 11H), 8.33 (d, 1H), 7.76 (dd, 1H), 7.59 (t, 1H), 7.53 (t,1H), 7.29 (d, 1H), 6.97 (d, 1H), 4.14 (t, 1H), 3.71(dd, 2H), 3.03 (m, 1H), 2.44(m, 4H), 2.00 (m, 2H), 1.45–1.90 (m, 4H).

Example 48

3-[3-(1-Thiazol-2-ylmethyl-piperidin-2-yl)-[1,2,4]oxadiazol-5-yl]-benzonitrile

3-[3-(1-Thiazol-2-ylmethyl-piperidin-2-yl)-[1,2,4]oxadiazol-5-yl]-benzonitrile (55.2 mg, 79%, white solid) was obtained from 3-(3-piperidin-2-yl-[1,2,4]oxadiazol-5-yl)-benzonitrile (50 mg, 0.20 mmol) and thiazole-2-carbaldehyde (19 μL, 0.22 mmol) in dichloroethane (1 mL) with sodium triacetoxyborohydride (62.5 mg, 0.29 mmol). Purification was performed on silica gel using 10% acetone in hexanes. $^1$H-NMR (CDCl$_3$), δ(ppm): 8.47 (dd, 1H), 8.38 (dd, 1H), 7.88 (dd, 1H), 7.67 (m, 2H), 7.29 (d, 1H), 4.03 (dd, 1H), 3.90 (dd, 2H), 3.12 (m, 1H), 2.49 (m, 1H), 1.72 (m, 6H).

Example 49

3-[5-(1-Thiazol-2-ylmethyl-pyrrolidin-2-yl)-[1,2,4]oxadiazol-3-yl]-benzonitrile

3-[5-(1-Thiazol-2-ylmethyl-pyrrolidin-2-yl)-[1,2,4]oxadiazol-3-yl]-benzonitrile (64 mg, 92%) was obtained from 3-(5-pyrrolidin-2-yl-[1,2,4]oxadiazol-3-yl)-benzonitrile (49.5 mg, 0.21 mmol) and thiazole-2-carbaldehyde (19 μL, 0.22 mmol) in dichloroethane (1 mL) with sodium triacetoxyborohydride (62.5 mg, 0.29 mmol). Purification was performed on silica using 15% ethyl acetate, 25% dichloromethane in hexane. $^1$H-NMR (CDCl$_3$), δ(ppm): 8.40 (br s, 1H), 8.32 (d, 1H), 7.78 (d, 1H), 7.69 (d, 1H), 7.60 (t, 1H), 7.27 (partially obscured by CDCl$_3$), 4.32 (m, 1H), 4.27 (d$_{AB}$, 1H), 4.17 (d$_{AB}$, 1H), 3.31 (m, 1H), 2.81 (q, 1H), 2.34–2.44 (m, 1H), 2.09–2.30 (m, 2H), 1.97–2.04 (m, 1H).

Example 50

3-{5-[1-(5-Chloro-pyridin-2-ylmethyl)-piperidin-2-yl]-[1,2,4]oxadiazol-3-yl}-benzonitrile 3-{5-[1-(5-Chloro-pyridin-2-ylmethyl)-piperidin-2-yl]-[1,2,4]oxadiazol-3-yl}-benzonitrile (22 mg, 59%) was obtained from 3-(5-piperidin-2-yl-[1,2,4]oxadiazol-3-yl)-benzonitrile (25.4 mg, 0.1 mmol) with 5-chloro-pyridine-2-carbaldehyde (17 mg, 0.12 mmol) and sodium triacetoxyborohydride (29.7 mg, 0.14 mmol) and dichloroethane (0.5 mL) at room temperature for 2 h. $^1$H NMR (CDCl$_3$), δ(ppm): 8.45 (d, 1H), 8.40 (d, 1H), 8.32 (dd, 1H), 7.80 (dd, 1H), 7.63 (m, 2H), 7.69 (d,1H), 4.14 (t, 1H), 3.73 (dd, 2H), 3.01 (m, 1H), 2.44 (m, 4H), 2.03 (m, 2H), 1.45–1.88 (m, 4H).

Example 51

2-[2-(5-m-Tolyl-[1,2,4]oxadiazol-3-yl)-piperidin-1-ylmethyl]-pyridine

2-[2-(5-m-Tolyl-[1,2,4]oxadiazol-3-yl)-piperidin-1-ylmethyl]-pyridine (29 mg, light yellow oil) was obtained from 2-[5-m-tolyl-[1,2,4]oxadiazol-3-yl]-piperidine (31 mg, 0.13 mmol) and pyridine-2-carbaldehyde (13 μL, 0.13 mmol) in dichloroethane (1 mL) with sodium triacetoxyborohydride (37.8 mg, 0.18 mmol). Purification was performed on silica gel using 10% acetone in hexanes. $^1$H-NMR (CDCl$_3$), δ(ppm): 8.47 (dd, 1H), 8.49 (d, 1H), 7.96 (m, 1H), 7.62 (dt, 1H), 7.49 (d, 1H), 7.39 (dd, 2H), 7.10 (dd, 1H), 3.83 (m, 2H), 3.50 (d, 1H), 3.05 (m, 1H), 2.44 (s, 3H), 2.30 (m, 1H), 1.72 (m, 6H).

Example 52

3-{5-[1-(5-Fluoro-pyridin-2-ylmethyl)-piperidin-2-yl]-[1,2,4]oxadiazol-3-yl}-benzonitrile 3-{5-[1-(5-Fluoro-pyridin-2-ylmethyl)-piperidin-2-yl]-[1,2,4]oxadiazol-3-yl}-benzonitrile (22 mg, 30%) was obtained from 3-(5-piperidin-2-yl-[1,2,4]oxadiazol-3-yl)-benzonitrile (51.4 mg, 0.202 mmol) with 5-fluoro-pyridine-2-carbaldehyde (38 mg, 0.303 mmol) and sodium triacetoxyborohydride (60 mg, 0.283 mmol) and dichloroethane (1.0 mL) at room temperature for 1 h. $^1$H NMR (CDCl$_3$), δ(ppm): 8.41 (d, 1H), 8.31 (m, 2H), 7.77 (dd, 1H), 7.61 (d, 1H), 7.49 (q, 1H), 7.35 (td,1H), 4.13 (t, 1H), 3.72(dd, 2H), 3.00 (m, 1H), 2.42 (m, 4H), 2.02 (m, 2H), 1.45–1.88 (m, 4H). LC-MS MH$^+$364.14.

Example 53

3-[5S-(3-Pyridin-2-ylmethyl-thiazolidin-4-yl)-[1,2,4]oxadiazol-3-yl]-benzonitrile 3-[5S-(3-Pyridin-2-ylmethyl-thiazolidin-4-yl)-[1,2,4]oxadiazol-3-yl]-benzonitrile (13 mg, 16%, light yellow oil) was obtained from 3-(5S-thiazolidin-4-yl-[1,2,4]oxadiazol- 3-yl)-benzonitrile (60 mg, 0.23 mmol) and pyridine-2-carbaldehyde (23 μL, 0.24 mmol) in dichloroethane (2 mL) with sodium triacetoxyborohydride (68.9 mg, 0.33 mmol). Purification was performed on silica gel using 30% ethyl acetate in hexanes. $^1$H-NMR (CDCl$_3$), δ(ppm): 8.57 (d, 1H), 8.39 (bs 1H), 8.30 (m,1H), 7.76 (m, 2H), 7.61 (m, 2H), 7.24 (m, 1H), 4.89 (dd, 1H), 4.39 (d, 1H), 4.22 (d, 1H), 3.97 (dd, 2H), 3.55 (m, 2H).

Example 54

3-{5-[1-(3-Methyl-pyridin-2-ylmethyl)-piperidin-2-yl]-[1,2,4]oxadiazol-3-yl}-benzonitrile 3-{5-[1-(3-Methyl-pyridin-2-ylmethyl)-piperidin-2-yl]-[1,2,4]oxadiazol-3-yl}-benzonitrile (44 mg, 61.3%) was obtained from 3-(5-piperidin-2-yl-[1,2,4]oxadiazol-3-yl)-benzonitrile (50.8 mg, 0.2 mmol) with 3-methyl-pyridine-2-carbaldehyde (96.8 mg, 0.8 mmol) and sodium triacetoxyborohydride (59.3 mg, 0.28 mmol) and dichloroethane (1 mL) at room temperature for 5 min. $^1$H NMR (CDCl$_3$), δ(ppm): 8.42 (d, 1H), 8.34 (m, 2H), 7.78 (dd, 1H), 7.61 (t, 1H), 7.42 (d,1H), 7.06 (dd, 1H), 4.13 (t, 1H), 3.74 (dd, 2H), 2.98 (m, 1H), 2.44 (m, 1H), 2.28 (s, 3H), 2.00 (m, 2H), 1.45–1.93 (m, 4H).

Example 55

3-{5-[1-(4-Methyl-pyridin-2-ylmethyl)-piperidin-2-yl]-[1,2,4]oxadiazol-3-yl}-benzonitrile 3-{5-[1-(4-Methyl-pyridin-2-ylmethyl)-piperidin-2-yl]-[1,2,4]oxadiazol-3-yl}-benzonitrile (40 mg, 55.7%) was obtained from 3-(5-piperidin-2-yl-[1,2,4]oxadiazol-3-yl)-benzonitrile (50.8 mg, 0.2 mmol) with 4-methyl-pyridine-2-carbaldehyde (48.4 mg, 0.4 mmol) and sodium triacetoxyborohydride (59.3 mg, 0.28 mmol) and dichloroethane (1 mL) at room temperature for 5 min. $^1$H NMR (CDCl$_3$), δ(ppm): 8.40 (d, 1H), 8.32 (m, 2H), 7.77 (dd, 1H), 7.60 (t, 1H), 7.26 (s,1H), 6.95 (d, 1H), 4.13 (t, 1H), 3.68 (dd, 2H), 3.03 (m, 1H), 2.42 (m, 1H), 2.27 (s, 3H), 2.03 (m, 2H), 1.45–1.92 (m, 4H).

Example 56

3-{5-[1-(5-Methyl-pyridin-2-ylmethyl)-piperidin-2-yl]-[1,2,4]oxadiazol-3-yl}-benzonitrile 3-{5-[1-(5-Methyl-pyridin-2-ylmethyl)-piperidin-2-yl]-[1,2,4]oxadiazol-3-yl}-benzonitrile (37 mg, 51.5%) was obtained from 3-(5-piperidin-2-yl-[1,2,4]oxadiazol-3-yl)-benzonitrile (50.8 mg, 0.2 mmol) with 5-methyl-pyridine-2-carbaldehyde (48.4 mg, 0.4 mmol) and sodium triacetoxyborohydride (59.3 mg, 0.28 mmol) and dichloroethane (1 mL) at room temperature for 5 min. $^1$H NMR (CDCl$_3$), δ(ppm): 8.41 (s, 1H), 8.33 (d & s, 2H), 7.78 (d, 1H), 7.60 (t, 1H), 7.44 (dd, 1H), 7.32 (d, 1H), 4.13 (t, 1H), 3.69 (dd, 2H), 3.02 (m, 1H), 2.41 (m, 1H), 2.27 (s, 3H), 2.03 (m, 2H), 1.45–1.92 (m, 4H).

Example 57

3-{5-[1-(1-Methyl-1H-benzoimidazol-2-ylmethyl)-piperidin-2-yl]-[1,2,4]oxadiazol-3-yl}-benzonitrile 3-{5-[1-(1-Methyl-1H-benzoimidazol-2-ylmethyl)-piperidin-2-yl]-[1,2,4]oxadiazol-3benzonitrile (63 mg, 79.1%) was obtained from 3-(5-piperidin-2-yl-[1,2,4]oxadiazol-3-yl)-benzonitrile (50.8 mg, 0.2 mmol) with 1-methyl-2-formylbenzimidazole (32 mg, 0.2 mmol), sodium triacetoxyborohydride (59.3 mg, 0.28 mmol) and dichloroethane (1 mL) at room temperature for 5 min. $^1$H NMR (CDCl$_3$), δ(ppm): 8.30 (s, 1H), 8.27 (d, 1H), 7.76 (d, 1H), 7.62 (d, 1H), 7.59 (t, 1H), 7.30 (d, 1H), 7.20 (m, 2H), 4.02 (t, 1H), 3.90(dd & s, 5H), 3.00 (m, 1H), 2.43 (m, 1H), 2.01 (s, 2H), 1.48–1.88 (m, 4H).

Example 58

3-[5-(6-Methyl-1-pyridin-2-ylmethyl-piperidin-2-yl)-[1,2,4]oxadiazol-3-yl]-benzonitrile 3-[5-(6-Methyl-1-pyridin-2-ylmethyl-piperidin-2-yl)-[1,2,4]oxadiazol-3-yl]-benzonitrile (4.5 mg, 12.5%) was obtained from 3-[5-(6-methyl-piperidin-2-yl)-[1,2,4]oxadiazol-3-yl]-benzonitrile hudrochloride (30.5 mg, 0.1 mmol) with pyridine-2-carbaldehyde (12.9 mg, 0.12 mmol), sodium triacetoxyborohydride (31.8 mg, 0.15 mmol) and triethylamine (50 μL) in dichloroethane (1 mL) at room temperature overnight. $^1$H NMR (CDCl$_3$), δ(ppm): 8.49(d, 1H), 8.30 (d, 1H), 8.23 (dd, 1H), 7.75 (dd, 1H), 7.61 (m, 3H), 7.05(td, 1H), 4.20 (dd, 1H), 3.86 (dd, 2H), 2.70 (m, 1H), 1.50–2.10 (m, 6H), 1.05 (d, 3H).

Example 59

3-[5-(4,4-Difluoro-1-pyridin-2-ylmethyl-piperidin-2-yl)-[1,2,4]oxadiazol-3-yl]-benzonitrile 3-[5-(4,4-Difluoro-1-pyridin-2-ylmethyl-piperidin-2-yl)-[1,2,4]oxadiazol-3-yl]-benzonitrile (13.5 mg, 35.4%) was obtained from 3-[5-(4,4-difluoro-piperidin-2-yl)-[1,2,4]oxadiazol-3-yl]-benzonitrile (29 mg, 0.1 mmol) with pyridine-2-carbaldehyde (12.9 mg, 0.12 mmol), sodium triacetoxyborohydride (31.8 mg, 0.15 mmol) and dichloroethane (1 mL) at room temperature overnight. $^1$H NMR (CDCl$_3$), δ(ppm): 8.53 (d, 1H), 8.39 (d, 1H), 8.31 (dd, 1H), 7.79 (dd, 1H), 7.68 (m, 2H), 7.44 (d, 1H), 7.18 (dd, 1H), 4.37 (dd, 1H), 3.88 (dd, 2H), 3.25 (m, 1H), 2.73 (m, 1H), 2.40–2.65 (m, 2H), 2.00–2.22 (m, 2H).

Example 60

3-[5-(4,4-Difluoro-1-thiazol-2-ylmethyl-piperidin-2-yl)-[1,2,4]oxadiazol-3-yl]-benzonitrile 3-[5-(4,4-Difluoro-1-thiazol-2-ylmethyl-piperidin-2-yl)-[1,2,4]oxadiazol-3-yl]-benzonitrile (9.1 mg, 23.5%) was obtained from 3-[5-(4,4-difluoro-piperidin-2-yl)-[1,2,4]oxadiazol-3-yl]-benzonitrile (29 mg, 0.1 mmol) with thiazole-2-carbaldehyde (13.6 mg, 0.12 mmol), sodium triacetoxyborohydride (31.8 mg, 0.15 mmol) and dichloroethane (1 mL) at room temperature overnight. $^1$H NMR (CDCl$_3$), δ(ppm): 8.40 (d, 1H), 8.34 (d, 1H), 7.80 (dd, 1H), 7.71 (d, 1H), 7.62 (t, 1H), 7.32 (d, 1H), 4.47 (dd, 1H), 4.17 (dd, 2H), 3.37(m, 1H), 2.85 (m, 1H), 2.40–2.75 (m, 2H), 2.05–2.25 (m, 2H).

Example 61

3-[5-(1-Quinolin-2-ylmethyl-piperidin-2-yl)-[1,2,4]oxadiazol-3-yl]-benzonitrile 3-(5-Piperidin-2-yl-[1,2,4]oxadiazol-3-yl)-benzonitrile (50.8 mg, 0.2 mmol) was mixed with 2-(chloromethyl)quinoline monohydrochloride (47.1 mg, 0.22 mmol) and diisopropylethylamine (129.3 mg, 1.0 mmol) in DMF (2 mL) at 80° C. for 20 h. The reaction mixture was poured into water and extracted with dichloromethane. The organic layer was washed with water and brine, dried with sodium sulfate, purified by column chromatography with 5~10% ethyl acetate in hexanes to give a colorless sticky oil. This sticky oil was mixed with 1 M HCl in ether (0.4 mL) and triturated with ethyl acetate to give an off-white solid, 45 mg (48%). $^1$H NMR (CDCl$_3$+DMSO-d$_6$), δ(ppm): 8.92 (d, 1H), 8.70 (d, 1H), 8.16 (m, 3H), 8.07 (d, 1H), 8.00 (t, 1H), 7.84 (m, 2H), 7.63 (m, 1H), 4.64 (m, 3H), 3.30 (m, 1H), 2.86(m, 1H), 2.04–2.38 (m, 2H), 1.57–1.90 (m, 4H).

Examples 62 to 79 were prepared as described for Example 61.

Example 62

3-{5-[1-(1H-Benzimidazole-2-ylmethyl)-piperidin-2-yl]-[1,2,4]oxadiazol-3-yl}-benzonitrile 3-{5-[1-(1H-Benzimidazole-2-ylmethyl)-piperidin-2-yl]-[1,2,4]oxadiazol-3-yl}-benzonitrile (15 mg, 19.6%) was obtained from 3-(5-piperidin-2-yl-[1,2,4]oxadiazol-3-yl)-benzonitrile (50.8 mg, 0.2 mmol) with 2-(chloromethyl)benzimidazole (33.3 mg, 0.20 mmol) and diisopropylethylamine (129.3 mg, 1.0 mmol) in DMF (2 mL) at 80° C. for 18 h. $^1$H NMR (CDCl$_3$+CD$_3$OD), δ(ppm): 8.27 (d, 1H), 8.25 (s, 1H), 7.83 (d, 1H, 7.65–7.76 (m, 3H), 7.53 (t, 2H), 4.67 (m, 3H), 3.23 (m, 1H), 2.82(m, 1H), 2.24 (m, 2H), 1.65–1.90 (m, 4H).

Example 63

3-{5-[1-(2-Methyl-thiazol-4-ylmethyl)-piperidin-2-yl]-[1,2,4]oxadiazol-3-yl}-benzonitrile 3-{5-[1-(2-Methyl-thiazol-4-ylmethyl)-piperidin-2-yl]-[1,2,4]oxadiazol-3-yl}-benzonitrile (18 mg, 49.2%) was obtained from 3-(5-piperidin-2-yl-[1,2,4]oxadiazol-3-yl)-benzonitrile (25.4 mg, 0.1 mmol) with 4-chloromethyl-2-methyl-thiazole hydrochloride (22.08 mg, 0.12 mmol) and diisopropylethylamine (64.6 mg, 0.5 mmol) in DMF (1 mL) at 80° C. for 60 h. $^1$H NMR (CDCl$_3$), δ(ppm): 8.43 (d, 1H), 8.35 (dd, 1H1), 7.78 (d, 1H), 7.61 (t, 1H), 6.94 (s, 1H), 4.12(t, 1H), 3.74 (dd, 2H), 3.10(m, 1H), 2.62 (s, 3H), 2.54 (m, 1H), 2.00 (m, 2H), 1.55–1.90 (m, 4H).

Example 64

3-{5-[1-(1-Benzyl-1H-imidazol-2-ylmethyl)-piperidin-2-yl]-[1,2,4]oxadiazol-3-yl}-benzonitrile 3-{5-[1-(1-Benzyl-1H-imidazol-2-ylmethyl)-piperidin-2-yl]-[1,2,4]oxadiazol-3yl}-benzonitrile (8 mg, 18.8%) was obtained from 3-(5-piperidin-2-yl-[1,2,4]oxadiazol-3-yl)-benzonitrile (25.4 mg, 0.1 mmol) with 1-benzyl-2-chloromethyl-1H-imidazole hydrochloride (29.2 mg, 0.12 mmol) and diisopropylethylamine (64.6 mg, 0.5 mmol) in DMF (1 mL) at 80° C. for 60 h. $^1$H NMR (CDCl$_3$), δ(ppm): 8.31 (s, 1H), 8.24 (dd, 1H), 7.76 (dd, 1H), 7.58 (t, 1H), 7.28 (m, 3H), 7.10(d, 2H), 6.93 (s, 1H), 6.86 (s, 1H), 5.36 (s, 2H), 3.93 (t, 1H), 3.66 (dd, 2H), 2.93(m, 1H), 2.34 (m, 1H), 1.92 (m, 2H), 1.45–1.80 (m, 4H).

Example 65

3-[5-(4-Pyridine-2-ylmethyl-morpholin-3-yl)-[1,2,4]oxadiazol-3-yl)-benzonitrile

3-[5-(4-Pyridine-2-ylmethyl-morpholin-3-yl)-[1,2,4]oxadiazol-3-yl)-benzonitrile (28 mg, 28%, light yellow oil) was obtained from 3-(3-morpholin-3-yl-[1,2,4]oxadiazol-5-yl)-benzonitrile (75 mg, 0.29 mmol), 2-picolyl chloride hydrochloride (72, 0.44 mmol) and diisopropylethylamine (0.15 mL, 0.88 mmol) in DMF (3 mL). $^1$H-NMR (CDCl$_3$), δ(ppm): 8.54 (t, 1H), 8.41 (d, 1H), 8.35 (m, 1H), 7.79 (m, 1H), 7.67 (m, 2H), 7.43 (d, 1H), 7.18 (dd, 1H), 4.21 (t, 1H), 4.06 (d, 2H), 3.86 (overlapping, m, 4H), 3.18 (m, 1H), 2.61 (m, 1H).

Example 66

3-{5-[1-(6-Bromo-pyridin-2-ylmethyl)-piperidin-2-yl]-[1,2,4]oxadiazol-3-yl}-benzonitrile 2-Bromo-6-bromomethyl-pyridine was prepared from 2-bromo-6-methylpyridine (465 mg, 2.7 mmol) with NBS (540 mg, 3.03 mmol) and AIBN (50 mg) in tetrachlorocarbon. 3-{5-[1-(6-Bromo-pyridin-2-ylmethyl)-piperidin-2-yl]-[1,2,4]oxadiazol-3-yl}-benzonitrile (380 mg, 90.5%) was obtained from 3-(5-piperidin-2-yl-[1,2,4]oxadiazol-3-yl)-benzonitrile (254 mg, 1.0 mmol) with 2-bromo-6-bromomethyl-pyridine (466 mg, 1.39 mmol) and diisopropylethylamine (517 mg, 4.0 mmol) in DMF (10 mL) at 80° C. for 18 h. $^1$H NMR (CDCl$_3$), δ(ppm): 8.40 (d, 1H), 8.32 (dd, 1H), 7.79 (dd, 1H), 7.61 (t, 1H), 7.54 (d, 2H), 7.33 (m, 1H), 4.15 (t, 1H), 3.75(dd, 2H), 3.04 (m, 1H), 2.49 (m, 1H), 2.04 (m, 2H), 1.50–1.86 (m, 4H).

Example 67

3–15-[1-(4-Methoxy-3,5-dimethyl-pyridin-2-ylmethyl)-piperidin-2-yl]-[1,2,4]oxadiazol-3-yl}-benzonitrile 3-{5-[1-(4-Methoxy-3,5-dimethyl-pyridin-2-ylmethyl)-piperidin-2-yl]-[1,2,4]oxadiazol-3-yl}-benzonitrile (64 mg, 79.3%) was obtained from 3-(5-piperidin-2-yl-[1,2,4]oxadiazol-3-yl)-benzonitrile (50.8 mg, 0.2 mmol) with 2-chloromethyl-4-methoxy-3,5-dimethyl-pyridine (44.5 mg, 0.24 mmol) and diisopropylethylamine (129.3 mg, 1.0 mmol) in DMF (2 mL) at 80° C. for 22 h. $^1$H NMR (CDCl$_3$), δ(ppm): 8.40 (d, 1H), 8.32 (dd, 1H), 8.10 (s, 1H), 7.78(dd, 1H), 7.62 (t, 1H), 4.10 (t, 1H), 3.72(dd & s, 5H), 2.97 (m, 1H), 2.43 (m, 1H), 2.27 (s, 3H), 2.18 (s, 3H), 2.04 (m, 2H), 1.46–1.82 (m, 4H).

Example 68

3-{5-[1-(6-Chloro-pyridin-2-ylmethyl)-piperidin-2-yl]-[1,2,4]oxadiazol-3-yl}-benzonitrile 2-Chloro-6-bromomethyl-pyridine was prepared from 2-chloro-6-methylpyridine (638 mg, 5.0 mmol) with NBS (996.5 mg, 5.6 mmol) and AIBN (92 mg) in tetrachlorocarbon. 3-{5-[1-(6-chromo-pyridin-2-ylmethyl)-piperidin-2-yl]-[1,2,4]oxadiazol-3-yl}-benzonitrile (450 mg, quantitative) was obtained from 3-(5-piperidin-2-yl-[1,2,4] oxadiazol-3-yl)-benzonitrile (300 mg, 1.18 mmol) with crude 2-chloro-6-bromomethyl-pyridine (640 mg, 3.12 mmol) and diisopropylethylamine (762.5 mg, 5.0 mmol) in DMF (8 mL) at 80° C. for 18 h. $^1$H NMR (CDCl$_3$), δ(ppm): 8.40 (d, 1H), 8.33 (dd, 1H), 7.79 (dd, 1H), 7.62 (q, 2H), 7.49 (d, 1H), 7.18 (d, 1H), 4.16 (t, 1H), 3.75(dd, 2H), 3.04 (m, 1H), 2.49 (m, 1H), 2.04 (m, 2H), 1.50–1.86 (m, 4H).

Example 69

3-[5-(1-Pyrazin-2-ylmethyl-piperidin-2-yl)-[1,2,4]oxadiazol-3-yl]-benzonitrile

2-Bromomethyl-pyrazine was prepared from 2-methyl-pyrazine (94 mg, 1.0 mmol) with NBS (199 mg, 1.12 mmol) and AIBN (18.4 mg) in tetrachlorocarbon (2 mL). 3-[5-(1-Pyrazin-2-ylmethyl-piperidin-2-yl)-[1,2,4]oxadiazol-3-yl]-benzonitrile (16 mg, 39.1%) was obtained from 3-(5-piperidin-2-yl-[1,2,4]oxadiazol-3-yl)-benzonitrile (30 mg, 0.118 mmol) with crude 2-bromomethyl-pyrazine (1.0 mmol) and diisopropylethylamine (76.2 mg, 0.59 mmol) in DMF (1.5 mL) at 80° C. for 50 h. $^1$H NMR (CDCl$_3$), δ(ppm): 8.74 (s, 1H), 8.44 (dd, 4H), 7.79 (dd, 1H), 7.62 (t, 1H), 4.19 (t, 1H), 3.82 (dd, 2H), 3.03 (m, 1H), 2.49 (m, 1H), 2.06 (m, 2H), 1.50–1.86 (m, 4H).

Example 70

3-[5-(1-Pyrimidin-4-ylmethyl-piperidin-2-yl)-[1,2,4]oxadiazol-3-yl]-benzonitrile 2-Bromomethyl-pyrimidine was prepared from 2-methyl-pyrimidine (94 mg, 1.0 mmol) with NBS (200 mg, 1.13 mmol) and AIBN (18.4 mg) in tetrachlorocarbon (2 mL). 3-[5-(1-Pyrimidin-4-ylmethyl-piperidin-2-yl)-[1,2,4]oxadiazol-3-yl]-benzonitrile (10 mg, 24%) was obtained from 3-(5-piperidin-2-yl-[1,2,4]oxadiazol-3-yl)-benzonitrile (30.5 mg, 0.12 mmol) with crude 2-bromomethyl-pyrimidine (1.0 mmol) and diisopropylethylamine (129.25 mg, 1.0 mmol) in DMF (1.0 mL) at 80° C. for an h. $^1$H NMR (CDCl$_3$), δ(ppm): 9.10 (s, 1H), 8.70 (d, 1H), 8.40 (s, 1H), 8.32(d, 1H), 7.79 (d, 1H), 7.61 (dd, 2H), 4.20 (t, 1H), 3.77 (dd, 2H), 3.03 (m, 1H), 2.49 (m, 1H), 2.09 (m, 2H), 1.50–1.86 (m, 4H).

Example 71

3-{5-[1-(5-Methyl-1,2,4]oxadiazol-3-ylmethyl)-piperidin-2-yl]-[1,2,4]oxadiazol-3-yl}-benzonitrile 3-{5-[1-(5-Methyl-[1,2,4]oxadiazol-3-ylmethyl)-piperidin-2-yl]-[1,2,4]oxadiazol-3-yl}-benzonitrile (16.2 mg, 23%) was obtained from 3-(5-piperidin-2-yl-[1,2,4]oxadiazol-3-yl)-benzonitrile (50.8 mg, 0.2 mmol) with 3-chloromethyl-5-methyl-[1,2,4]oxadiazole (59 mg, 0.445 mmol) and diisopropylethylamine (103.5 mg, 0.801 mmol) in DMF (1.5 mL) at 80° C. for 20 h. $^1$H NMR (CDCl$_3$), δ(ppm): 8.44 (s, 1H), 8.36(d, 1H), 7.79 (d, 1H), 7.62 (t, 1H), 4.25 (t, 1H), 3.83 (s, 2H), 3.12 (m, 1H), 2.61 (m, 1H), 2.57 (s, 3H), 2.06 (m, 2H), 1.50–1.85 (m, 4H).

Example 72

3-{5-[1-(4-Chloro-pyridin-2-ylmethyl)-piperidin-2-yl]-[1,2,4]oxadiazol-3-yl}-benzonitrile 2-Bromomethyl-4-chloropyridine was prepared from 2-methyl-pyridine (127.57 mg, 1.0 mmol) with NBS (199.2 mg, 1.12 mmol) and AIBN (18.4 mg) in tetrachlorocarbon (2 mL). 3-{5-[1-(4-Chloro-pyridin-2-ylmethyl)-piperidin-2-yl]-[1,2,4]oxadiazol-3-yl}-benzonitrile (51 mg, 67.1%) was obtained from 3-(5-piperidin-2-yl-[1,2,4]oxadiazol-3-yl)-benzonitrile (50.8 mg, 0.2 mmol) with crude 2-bromomethyl-4-chloropyridine (1.0 mmol) and diisopropylethylamine (129.25 mg, 1.0 mmol) in DMF (1.5 mL) at 80° C. for 20 h. $^1$H NMR (CDCl$_3$), δ(ppm): 8.39 (dd, 2H), 8.31 (dd, 1H), 7.79 (dd, 1H), 7.61 (t, 1H), 7.55 (d, 1H), 7.15 (dd, 2H), 4.16 (t, 1H), 3.74 (dd, 2H), 3.00 (m, 1H), 2.45 (m, 1H), 2.05 (m, 2H), 1.50–1.86 (m, 4H).

Example 73

2-{2-[3-(3-Cyano-phenyl)-[1,2,4]oxadiazol-5-yl]-piperidin-1-ylmethyl}-thiazole-4-carbonitrile 2-Bromomethyl-thiazole-4-carbonitrile was prepared from 2-methyl-1,3-thiazole-4-carbonitrile (124 mg, 1.0 mmol) with NBS (199.3 mg, 1.12 mmol) and AIBN (18.4 mg) in tetrachlorocarbon (2 mL). 2-{2-[3-(3-Cyano-phenyl)-[1,2,4]oxadiazol-5-yl]-piperidin-1-ylmethyl}-thiazole-4-carbonitrile (56 mg, 74.4%) was obtained from 3-(5-piperidin-2-yl-[1,2,4]oxadiazol-3-yl)-benzonitrile (50.8 mg, 0.2 mmol) with crude 2-bromomethyl-thiazole-4-carbonitrile (1.0 mmol) and diisopropylethylamine (129.25 mg, 1.0 mmol) in DMF (1.5 mL) at 80° C. for 20 h. $^1$H NMR (CDCl$_3$), δ(ppm): 8.38 (d, 1H), 8.31 (dd, 1H), 7.97 (s, 1H), 7.80 (dd, 1H), 7.62 (d, 1H), 4.30 (t, 1H), 4.00 (dd, 2H), 3.07 (m, 1H), 2.62 (m, 1H), 2.11 (m, 2H), 1.60–1.80 (m, 4H).

Example 74

3-[5-(1-Benzothiazol-2-ylmethyl-piperidin-2-yl)-[1,2,4]oxadiazol-3-yl]benzonitrile 2-Bromomethyl-benzothiazole was prepared from 2-methyl-benzothiazole (149.21 mg, 1.0 mmol) with NBS (199.3 mg, 1.12 mmol) and AIBN (18.4 mg) in tetrachlorocarbon (2 mL). 3-[5-(1-Benzothiazol-2-ylmethyl-piperidin-2-yl)-[1,2,4]oxadiazol-3-yl]-benzonitrile (3.1 mg, 6.6%) was obtained from 3-(5-piperidin-2-yl-[1,2,4]oxadiazol-3-yl)-benzonitrile (30 mg, 0.118 mmol) with crude 2-bromomethyl-benzothiazole (1.0 mmol) and diisopropylethylamine (129.25 mg, 1.0 mmol) in DMF (1.5 mL) at 80° C. for 20 h. $^1$H NMR (CDCl$_3$), δ(ppm): 8.40(s, 1H), 8.33 (d, 1H), 7.93 (d, 1H), 7.88 (d, 1H), 7.77 (d, 1H), 7.61 (t, 1H), 7.44 (t, 1H), 7.36 (t,1H), 4.35 (t, 1H), 4.16 (dd, 2H), 3.16 (m, 1H), 2.72 (m, 1H), 2.14 (m, 2H), 1.60–1.82 (m, 4H).

Example 75

6-{2-[3-(3-Cyano-phenyl)-[1,2,4]oxadiazol-5-yl]-piperidin-1-ylmethyl}-nicotinonitrile 6-Bromomethyl-nicotinonitrile was prepared from 6-methyl-nicotinonitrile (148.14 mg, 1.0 mmol) with NBS (199.3 mg, 1.12 mmol) and AIBN (18.4 mg) in tetrachlorocarbon (2 mL). 6-{2-[3-(3-Cyano-phenyl)-[1,2,4]oxadiazol-5-yl]-piperidin-1-ylmethyl}-nicotinotrile (28 mg, 64%) was obtained from 3-(5-piperidin-2-yl-[1,2,4]oxadiazol-3-yl)-benzonitrile (30 mg, 0.118 mmol) with crude 6-bromomethyl-nicotinonitrile (1.0 mmol) and diisopropylethylamine (129.25 mg, 1.0 mmol) in DMF (1.5 mL) at 80° C. for 20 h. $^1$H NMR (CDCl$_3$), δ(ppm): 8.76(d, 1H), 8.38 (d, 1H), 8.31 (dd, 1H), 7.95 (dd, 1H), 7.79 (d, 1H), 7.71 (d, 1H), 7.61 (t, 1H), 4.17 (t, 1H), 3.83 (dd, 2H), 3.00 (m, 1H), 2.45 (m, 1H), 2.04 (m, 2H), 1.50–1.90 (m, 4H).

Example 76

3-{5-[1-(5-Methyl-isoxazol-3-ylmethyl)-piperidin-2-yl]-[1,2,4]oxadiazol-3-yl}-benzonitrile 3-{5-[1-(5-Methyl-isoxazol-3-ylmethyl)-piperidin-2-yl]-[1,2,4]oxadiazol-3-yl}-benzonitrile -benzonitrile (29.2 mg, 64%) was obtained from 3-(5-piperidin-2-yl-[1,2,4]oxadiazol-3-yl)-benzonitrile (25.4 mg, 0.10 mmol) with 3-bromomethyl-5-methyl-isoxazole (26.4 mg, 0.15 mmol) and diisopropylethylamine (129.25 mg, 1.0 mmol) in DMF (1.5 mL) at 80° C. for 20 h. $^1$H NMR (CDCl$_3$), δ(ppm): 8.42(d, 1H), 8.35 (dd, 11H), 7.80 (dd, 1H), 7.62 (t, 1H), 6.02 (d, 1H), 4.07 (dd, 1H), 3.64 (dd, 2H), 3.03 (m, 1H), 2.45 (m, 1H), 2.40 (s, 3H), 1.97 (m, 2H), 1.45–1.86 (m, 4H).

Example 77

3-Methoxy-5-[3-(1-pyridin-2-ylmethyl-piperidin-2-yl)-[1,2,4]oxadiazol-5-yl]-benzonitrile 3-Methoxy-5-[3-(1-pyridin-2-ylmethyl-piperidin-2-yl)-[1,2,4]oxadiazol-5-yl]-benzonitrile (2.8 mg, 5%) was obtained from 3-methoxy-5-(3-piperidin-2-yl-[1,2,4]oxadiazol-5-yl)-benzonitrile (40.6 mg, 0.14) with 2-chloromethyl-pyridine hydrochloride (35.1 mg, 0.21 mmol) and diisopropylethylamine (124 μL, 0.71 mmol) in DMF (1 mL) at 80° C. overnight. 1H NMR (CDCl$_3$), δ(ppm): 8.51 (d, 1H), 8.04 (m, 1H), 7.90 (d, 1H), 7.61 (t, 1H), 7.46 (d, 1H), 7.35 (d, 1H), 7.13 (m, 1H), 3.94 (s, 3H), 3.88 (m, 1H), 3.82 (d, 1H), 3.52 (d 1H), 3.02 (m, 1H), 2.32 (m, 1H), 2.12–1.80 (m, 3H), 1.80–1.20 (m, 3H).

Example 78

2-{2-[5-(3-Methoxy-phenyl)-[1,2,4]oxadiazol-3-yl]-piperidin-1-ylmethyl}-pyridine 2-{2-[5-(3-Methoxy-phenyl)-[1,2,4]oxadiazol-3-yl]-piperidin-1-ylmethyl}-pyridine (4.9 mg, yellow oil) was obtained from 2-[5-(3-methoxy-phenyl)-[1,2,4]oxadiazol-3-yl]-piperidine (60 mg, 0.23 mmol), 2-picolyl chloride hydrochloride (75.9 mg, 0.46 mmol), diisopropylethylamine (0.20 mL, 1.16 mmol) and DMF (3 mL) at 120° C. for 1 h. $^1$H-NMR (CDCl$_3$), δ(ppm): 8.49 (d, 1H), 7.66 (m, 3H), 7.44 (m, 2H), 7.10 (m, 2H), 3.86 (m, 5H), 3.50 (d, 1H), 3.05 (m, 1H), 2.26 (m, 1H), 1.82 (m, 5H), 1.69 (m, 1H).

Example 79

3-[5-(1-Pyridin-2-ylmethyl-pyrrolidin-2-yl)-[1,2,4]oxadiazol-3-yl]-benzonitrile

3-[5-(1-Pyridin-2-ylmethyl-pyrrolidin-2-yl)-[1,2,4]oxadiazol-3-yl]-benzonitrile (35 mg, 50%) was obtained from 3-(5-pyrrolidin-2-yl-[1,2,4]oxadiazol-3-yl)-benzonitrile (51 mg, 0.21 mmol), 2-picolyl chloride hydrochloride (83 mg, 0.51 mmol), diisopropylethylamine (0.25 mL, 1.4 mmol) and DMF (2 mL) at 80° C. for 16 h. Purification was performed on silica using 5–33% ethyl acetate in dichloromethane. $^1$H-NMR (CDCl$_3$), δ(ppm): 8.49 (d, 1H), 8.37 (br s, 1H), 8.31 (d, 1H), 7.77 (d, 1H), 7.57–7.62 (m, 2H), 7.38 (d, 1H), 7.11 (m, 1H), 4.22 (m, 1H), 4.02 (d$_{AB}$, 1H), 3.89 (d$_{AB}$, 1H), 3.20 (m, 1H), 2.70 (q, 1H), 2.37 (m, 1H), 2.05–2.30 (m, 2H), 1.90–2.04 (m, 1H). (note: NMR also indicated traces of DMF present).

Example 80

2-{2-[3-(3-Methoxy-phenyl)-[1,2,4]oxadiazol-5-yl]-piperidin-1-ylmethyl}-pyridine 1-Pyridin-2-ylmethyl-piperidine-2-carboxylic acid methyl ester (50 mg, 0.213 mmol) was mixed with N-hydroxy-3-methoxy-benzamidine (29 mg, 0.174 mmol) and sodium tert-butoxide (19 mg, 0.20 mmol) in toluene (0.5 mL) in a sealed vial at 130° C. for 10 min. The reaction mixture was cooled down and diluted with dichloromethane, washed with water. The title compound was purified by silica gel colomn chromatography with 20~30% ethyl acetate in hexanes to give a colorless oil, 20 mg (32.7%). $^1$H NMR (CDCl$_3$), δ(ppm): 8.50 (d, 1H), 7.66 (m, 3H), 7.47 (d, 1H), 7.38 (t, 1H), 7.13 (dd, 1H), 7.03 (dd, 1H), 4.11 (t, 1H), 3.88 (s, 3H), 3.73 (dd, 2H), 3.04 (m, 1H), 2.42 (m, 1H), 2.03 (m, 2H), 1.46-1.90 (m, 4H).

Examples 81 to 86 were prepared as described for Example 80.

Example 81

(RS)-2–12-(3-Thiophen-2-yl-[1,2,4]oxadiazol-5-yl)-piperidin-1-ylmethyl]-pyridine)

(RS)-2-[2-(3-Thiophen-2-yl-[1,2,4]oxadiazol-5-yl)-piperidin-1-ylmethyl]-pyridine (3.7 mg, 5.67%) was obtained from (S)-1-pyridin-2-ylmethyl-piperidine-2-carboxylic acid methyl ester (46.8 mg, 0.2 mmol) with N-hydroxy-thiophene-2-carboxamidine (28.4 mg, 0.2 mmol) and sodium tert-butoxide (19.2 mg, 0.2 mmol) in toluene (1.0 mL) in a sealed vial at 110° C. for 20 h. $^1$H NMR (CDCl$_3$), δ(ppm): 8.51 (d, 1H), 7.81(dd, 1H), 7.63 (td, 1H), 7.49 (m, 2H), 7.14 (m, 2H), 4.10 (dd, 1H), 3.72 (dd, 2H), 3.02 (m, 1H), 2.41 (m, 1H), 2.01 (m, 2H), 1.45–1.90 (m, 4H).

Example 82

2-[2-(3-Phenyl-11,2,4]oxadiazol-5-yl)-piperidin-1-ylmethyl]-pyridine

2-[2-(3-Phenyl-[1,2,4]oxadiazol-5-yl)-piperidin-1-ylmethyl]-pyridine (16.4 mg, 24%, clear oil) was obtained from N-hydroxy-benzamidine (29.1 mg, 0.21 mmol) and 1-pyridin-2-ylmethyl-piperidine-2-carboxylic acid methyl ester (50 mg, 0.21 mmol) with sodium tert-butoxide (20.5 mg, 0.21 mmol) in toluene (1 mL) at 120° C. overnight. Purification was performed on silica gel using 10% acetone in hexanes. $^1$H-NMR (CDCl$_3$), δ(ppm): 8.51 (d, 1H), 8.10 (d, 2H), 7.65 (t, 1H), 7.49 (m, 4H), 7.14 (dd, 1H), 4.12 (t, 1H), 3.73 (dd, 2H), 3.04 (m, 1H), 2.43 (m, 1H), 2.05 (m, 2H), 1.69 (m, 4H).

Example 83

2-[2-(3-m-Tolyl-[1,2,4]oxadiazol-5-yl)-piperidin-1-ylmethyl]-pyridine

2-[2-(3-m-Tolyl-[1,2,4]oxadiazol-5-yl)-piperidin-1-ylmethyl]-pyridine (16.4 mg, 24%, light yellow oil) was obtained from N-hydroxy-3-methyl-benzamidine (32.0 mg, 0.21 mmol) and 1-pyridin-2-ylmethyl-piperidine-2-carboxylic acid methyl ester (50 mg, 0.21 mmol) with sodium tert-butoxide (20.5 mg, 0.21 mmol) in toluene (1 mL) at 120° C. overnight. Purification was performed on silica gel using 10% acetone in hexanes to isolate the title compound. $^1$H-NMR (CDCl$_3$), δ(ppm): 8.51 (d, 1H), 7.90 (m, 2H), 7.64 (dt, 1H), 7.48 (d, 1H), 7.34 (m, 2H), 7.14 (dd, 1H), 4.11 (t, 1H), 3.70 (dd, 2H), 3.04 (m, 1H), 2.44 (m, 4H), 2.04 (m, 2H), 1.61 (m, 4H).

Example 84

(RS)-2-[2-(3-m-Tolyl-[1,2,4]oxadiazol-5-yl)-piperidin-1-ylmethyl]-pyridine (RS)-2-[2-(3-m-Tolyl-[1,2,4]oxadiazol-5-yl)-piperidin-1-ylmethyl]-pyridine (6.2 mg, 9.3%) was obtained from (S)-1-pyridin-2-ylmethyl-piperidine-2-carboxylic acid methyl ester (46.8 mg, 0.2 mmol) with N-hydroxy-3-methyl-benzamidine (30 mg, 0.2 mmol) and sodium tert-butoxide (19.2 mg, 0.2 mmol) in toluene (1.0 mL) in a sealed vial at 110° C. for 20 h.

Example 85

(RS)-2-{2-[3-(3-Fluoro-5-imidazol-1-yl-phenyl)-[1,2,4]oxadiazol-5-yl]-piperidin-1-ylmethyl}-pyridine (RS)-2-{2-[3-(3-Fluoro-5-imidazol-1-yl-phenyl)-[1,2,4]oxadiazol-5-yl]-piperidin-1-ylmethyl}-pyridine (3.4 mg, 4.2%) was obtained from (S)-1-pyridin-2-ylmethyl-piperidine-2-carboxylic acid methyl ester (46.8 mg, 0.2 mmol) with 3-fluoro-N-hydroxy-5-imidazol-1-yl-benzamidine (44 mg, 0.2 mmol) and sodium tert-butoxide (19.2 mg, 0.2 mmol) in toluene (1.0 mL) and ethanol (0.5 mL) in a sealed vial at 110° C. for 20 h. $^1$H NMR (CDCl$_3$), δ(ppm): 8.52 (d, 1H), 7.96 (dd, 2H), 7.83 (dd, 1H), 7.65 (td, 1H) 7.48 (m, 1H), 7.37 (d, 1H), 7.29 (m, 2H), 7.15 (dd, 1H), 4.13 (t, 1H), 3.70 (dd, 2H), 3.04 (m, 1H), 2.45 (m, 1H), 2.05 (m, 2H), 1.44–1.90 (m, 4H).

Example 86

2-{2-[3-(3-Ethyl-phenyl)-[1,2,4]oxadiazol-5-yl]-piperidin-1-ylmethyl}-pyridine

2-{2-[3-(3-Ethyl-phenyl)-[1,2,4]oxadiazol-5-yl]-piperidin-1-ylmethyl}-pyridine (16 mg, 22%) was obtained from 1-pyridin-2-ylmethyl-piperidine-2-carboxylic acid methyl ester (58 mg, 0.247 mmol) with 3-ethyl-N-hydroxy-benzamidine (34 mg, 0.207 mmol) and sodium tert-butoxide (18 mg, 0.183 mmol) in toluene (1.0 mL) at 120° C. for 4 h. $^1$H NMR (CDCl$_3$), δ(ppm): 8.51 (d, 1H), 7.92 (s & d, 2H), 7.64 (td, 1H), 7.48 (d, 1H), 7.34 (m, 2H), 7.13 (dd, 1H), 4.11 (t, 1H), 3.72 (dd, 2H), 3.04 (m, 1H), 2.72 (q, 2H), 2.42 (m, 1H), 2.04 (m, 2H), 1.46–1.90 (m, 4H), 1.27 (t, 3H).

Example 87

5-Methyl-pyridine-2-carbonitrile

2-Bromo-5-methylpyridine ((8.6 g, 50 mmol) was mixed with Zn(CN)2 (4.1 g, 35 mmol), Pd(dppf)2C12 (0.89 g, mmol) and zinc dust (0.14 g, mmol) in DMF (86 ml) at 155° C. for 15 minutes. The reaction mixture was cooled down to room temperature and quenched with water and ethyl acetate. The mixture was filtered through celite and the organic layer was separated and dried with sodium sulfate. The product was purified by column chromatography with 10~25% ethyl acetate in hexanes to give 3.4 g of 5-methyl-pyridine-2-carbonitrile (yield: 57.6%). $^1$H NMR (CDCl3), δ(ppm): 8.52 (s, 1H), 7.59 (m, 2H), 2.42 (s, 1H).

Example 88

5-Methyl-piperidine-2-carboxylic acid hydrochloride 5-methyl-pyridine-2-carbonitrile(3.34 g, 28.3 mmol)was mixed with 18% HCl (12 ml) and ethanol (6 ml) and refluxed for 40 h. The reaction mixture was concentrated by rotavapor and the residue was triturated with acetone to give off-white solid 5-methyl-pyridine-2-carboxylic acid hydrochloride. This solid was hydrogenated with PtO$_2$ in ethanol for 2 days until no UV active material left. The reaction mixture was filtered, concentrated by vacuum. The residue was triturated with acetone to give 5.3 g of cis and trans 5-methyl-piperidine-2-carboxylic acid hydrochloride as white solid (quantitative).

Example 89

4-Methyl-piperidine-2-carboxylic acid ethyl ester hydrochloride

To a dichloromethane (50 mL) solution of 1-benzhydryl-4-methyl-1,2,3,6-tetrahydro-pyridine-2-carboxylic acid ethyl ester *(5.0 g, 14.9 mmol), 1-chloroethyl chloroformate (2.13 g, 14.9 mmol) was added at room temperature under argon. The reaction mixture was stirred overnight. After the reaction mixture was mixed with methanol (50 mL) and refluxed for an hour, cooled down to room temperature and 10% Pd/C (2 g) was added to reaction mixture and stirred under hydrogen overnight. The reaction mixture was filtered through celite and 1 M HCl in ether (15 mL) was added. After concentration, the residue was triturated with acetone, filtered to 2.03 g (65.5%) of 4-methyl-piperidine-2-carboxylic acid ethyl ester hydrochloride.

*Bailley, Patrick D et al: *Tetrahedron Lett.*; 43(6), 2002: 1067–1070

Example 90

4-Methyl-piperidine-1,2-dicarboxylic acid 1-tert-butyl ester 4-methyl-piperidine-2-carboxylic acid ethyl ester hydrochloride (2.0 g, 9.6 mmol) was mixed with sodium hydroxide (1.155 g, 28.9 mmol) in water (10 mL) and acetone (5 mL) at 60° C. for 30 minutes. The reaction mixture was mixed with, di-tert-butyl dicarbonate (2.7 g, 12.5) and stirred overnight. The reaction mixture was brought to pH2~3 using hydrochloric acid (1 N aqueous) and then extracted with dichloromethane. The organic phase was separated, sequentially washed with water and brine, dried (sodium sulfate), filtered and concentrated in vacuo. The isolated solid was triturated with hexanes to yield 1.89 g (80.7%) of 4-methyl-piperidine-1,2-dicarboxylic acid 1-tert-butyl ester as white solid.

Example 91

3-Methyl-piperidine-2-carboxylic acid hydrochloride

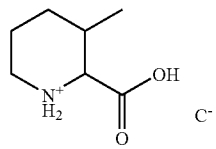

3-Methyl-piperidine-2-carboxylic acid hydrochloride (0.92 g, 79.3%) was obtained from 3-methyl-pyridine-2-carboxylic acid hydrochloride (1.12, 6.45 mmol) by hydrogenateion with PtO2 (50 mg) in ethanol (11 mL) and water (6 mL). $^1$H-NMR(D20) δ(ppm): 3.99 (d, 1H), 3.31 (wd, 1H), 2.89 (m,1H), 2.47 (m, 1H), 1.67 (m, 4H) and 0.90 (d, 3H).

Example 92

3-Methyl-piperidine-1,2-dicarboxylic acid 1-tert-butyl ester

3-Methyl-piperidine-1,2-dicarboxylic acid 1-tert-butyl ester (0.672 g, %) was obtained as described in Example 18 from 3-methyl-piperidine-2-carboxylic acid hydrochloride (0.9 g, 5 mmol) with di-tert-butyl dicarbonate (1.308 g, 6 mmol) and K2CO3 (2.76 g, 20 mmol) in acetone(10 mL) and water (20 mL).

Example 93

(R)- and (S)-2-[3-(3-Cyano-phenyl)-[1,2,4]oxadiazol-5-yl]-piperidine-1-carboxylic acid tert-butyl ester The enantiomers of compound in Example 25 were prepared in an identical manner to that carried out in Example 25 starting from (R)- or (S)-piperidine-1,2-dicarboxylic acid 1-tert-butyl ester, respectively. Deprotection to give the free amine was carried out as in example 34 using formic acid.

Example 94

(R)- and (S)-3-[5-(1-Pyridin-2-ylmethyl-piperidin-2-yl)-[1,2,4]oxadiazol-3-yl]-benzonitrile The enantiomers of compound in Example 43 were prepared from the (R)- or (S)-amine either by SN2 displacement as in Example 61 or by reductive amination as in Example 43.

Example 95

(S)-3-[5-(1-Thiazol-2-ylmethyl-piperidin-2-yl)-[1,2,4]oxadiazol-3-yl]-benzonitrile The (S)-enantiomer of compound in Example 45 was prepared by reductive amination with thiazole-2-carbaldehyde as in example 43 using the chiral amine prepared above.

Example 96

3-(5S-Thiazolidin-4-yl-[1,2,4]oxadiazol-3-yl)-benzonitrile

4-[3-(3-Cyano-phenyl)-[1,2,4]oxadiazol-5-yl]-(S)-thiazolidine-3-carboxylic acid tert-butyl ester (212 mg, 20%, yellow oil) was prepared according to the procedure in Example 25 from Boc-L-thiazolidine-4-carboxylic acid (696 mg, 2.98 mmol) with isobutylchloroformate (0.43 ml, 3.28 mmol) and N-methylmorpholine (0.36 ml, 3.28 mmol) in THF (5 ml) at 40° C. for 2 h. Then 3-cyano-N-hydroxybenzamidine (577 mg, 3.58 mmol) and additional N-methylmorpholine (0.39 ml, 3.58 mmol) and THF (4 ml) at room temperature overnight followed by extraction of the product and addition of DMF (2 ml) and the mixture was heated at 120° C. overnight. The crude residue was purified on silica gel using 20% ethyl acetate.

3-(5S-Thiazolidin-4-yl-[1,2,4]oxadiazol-3-yl)-benzonitrile (134 mg, 88%, brown oil) was obtained as described in Example 39 from 4-[3-(3-cyano-phenyl)-[1,2,4]oxadiazol-5-yl]-(S)-thiazolidine-3-carboxylic acid tert-butyl ester (212 mg) in dichloromethane (4 mL) and trifluoroacetic acid (2 mL) at room temperature for 5 h. $^1$H-NMR (CDCl$_3$), δ(ppm): 8.40 (bs, 1H), 8.32 (d, 1H), 7.80 (d, 1H), 7.62 (t, 1H), 4.77 (t, 1H), 4.36 (dd, 2H), 3.45 (dd, 1H), 3.25 (dd, 1H).

Example 97

(S)-3-(5-Pyrrolidin-2-yl-[1,2,4]oxadiazol-3-yl)-benzonitrile (S)-2-[3-(3-Cyano-phenyl)-[1,2,4]oxadiazol-5-yl]-pyrrolidine-1-carboxylic acid tert-butyl ester (698 mg, 44%) was prepared according to the procedure in Example 25 from (S)-pyrrolidine-1,2-dicarboxylic acid 1-tert-butyl ester (1.00 g, 4.66 mmol) with isobutyl chloroformate (0.64 mL, 4.9 mmol) and triethylamine (1.6 mL, 11.5 mmol) in THF (14 mL). Then 3-cyano-N-hydroxy-benzamidine (753 mg, 4.67 mmol) and DMF (15 mL) were added and the mixture was heated at 120° C. for 18 h.

(S)-3-(5-Pyrrolidin-2-yl-[1,2,4]oxadiazol-3-yl)-benzonitrile (360 mg, 73%) was prepared according to the procedure in Example 39 from (S)-2-[3-(3-cyano-phenyl)-[1,2,4]oxadiazol-5-yl]-pyrrolidine-1-carboxylic acid tert-butyl ester (697 mg, 2.05 mmol) in dichloromethane (15 mL) and trifluoroacetic acid (2.4 mL) at room temperature for 2 h. $^1$H NMR (CDCl$_3$), δ(ppm): 8.39 (s, 1H), 8.32 (d, 1H), 7.78 (d, 1H), 7.60 (t, 1H), 4.58 (dd, 1H), 3.22 (m, 1H), 3.13 (m, 1H), 2.34 (m, 1H), 2.14 (m, 1H), 2.00 (m, 3H).

Example 96

(S)-3-[5-(2,5-Dihydro-1H-pyrrol-2-yl)-[1,2,4]oxadiazol-3-yl]-benzonitrile (S)-2-[3-(3-Cyano-phenyl)-[1,2,4]oxadiazol-5-yl]-2,5-dihydro-pyrrole-1-carboxylic acid tert-butyl ester (372 mg, 42%, slightly impure) was prepared according to the procedure in Example 25 from (S)-2,5-dihydro-pyrrole-1,2-dicarboxylic acid 1-tert-butyl ester (557.8 mg, 2.62 mmol) with isobutyl chloroformate (0.36 mL, 2.77 mmol) and triethylamine (0.73 mL, 5.2 mmol) in THF (7.5 mL). Then 3-cyano-N-hydroxy-benzamidine (424 mg, 2.6 mmol) and DMF (7 mL) were added and the mixture was heated at 120° C. for 16 h. $^1$H-NMR (CDCl$_3$) was consistent with the expected product and showing a mixture of rotomers due to the Boc protecting group.

(S)-3-[5-(2,5-Dihydro-1H-pyrrol-2-yl)-[1,2,4]oxadiazol-3-yl]-benzonitrile (102.4 mg, 39%, 90% purity) was prepared according to the procedure in Example 39 from (S)-2-[3-(3-cyano-phenyl)-[1,2,4]oxadiazol-5-yl]-2,5-dihydro-pyrrole-1-carboxylic acid tert-butyl ester (370 mg, 1.09 mmol) in dichloromethane (10 mL) and trifluoroacetic acid (1.3 mL) at room temperature for 2 h. $^1$H NMR (CDCl$_3$), δ(ppm): 8.36 (s 1H), 8.31 (d, 1H), 7.77 (d, 1H), 7.62 (t, 1H), 6.41 (m, 1H), 6.18 (m, 1H), 5.45 (m, 1H), 4.03 (m, 2H), 2.5–2.9 (br s, 1H). The aromatized pyrrole was also isolated (69.9 mg, 27%) and was found to be identical by $^1$H NMR to the 10% impurity in the title compound. $^1$H NMR (CDCl$_3$), δ(ppm): 9.45 (br s, 1H), 8.44 (s, 1H), 8.37 (d, 1H), 7.81 (d, 1H), 7.64 (t, 1H), 7.27 (m, 1H), 7.17 (m, 1H), 6.44 (m, 1H).

Example 97 trans-3-[5-(5-methyl-piperidin-2-yl)-[1,2,4]oxadiazol-3-yl]-benzonitrile and cis-3-[5-(5-methyl-piperidin-2-yl)-[1,2,4]oxadiazol-3-yl]-benzonitrile 5-methyl-piperidine-1,2-dicarboxylic acid 1-tert-butyl ester (3.3 g, sticky oil) was prepared according to the procedure in Example 18 from 5-methyl-piperidine-2-carboxylic acid hydrochloride (2.0 g, 11.13 mmol), potassium carbonate (7.71 g, 55.88 mmol), di-tert-butyl dicarbonate (3.98 g, 18.16 mmol) in acetone (5 mL) and water (20 mL) at room temperature overnight.

2-[3-(3-Cyano-phenyl)-[1,2,4]oxadiazol-5-yl]-5-methyl-piperidine-1-carboxylic acid tert-butyl ester (1.97 g, 48% in 2 steps, sticky oil) was prepared according to the procedure in Example 30 from 5-Methyl-piperidine-1,2-dicarboxylic acid 1-tert-butyl ester (3.0 g, 12.3 mmol) with 3-cyano-N-hydroxy-benzamidine (1.98 mg, 12.3 mmol), EDCI (2.35 mg, 12.3 mmol) and HOBt (1.66 mg, 12.3 mmol) in DMF (10 mL) overnight. Then the crude product was heated in DMF (5 mL) at 135° C. for 3 h. The product was purified by column chromatography with 5~10% ethyl acetate in hexanes.

This material was deprotected using formic acid at 50° C. for an hour according to the procedure in Example 39. The product was purified by column chromatography with 25%~30% ethyl acetate in hexane to give trans-3-[5-(5-methyl-piperidin-2-yl)-[1,2,4]oxadiazol-3-yl]-benzonitrile (338 mg, 23.6%). $^1$H NMR (CDCl3), δ(ppm): 8.4 (s, 1H), 8.33 (d, 1H), 7.77 (dd,1H), 7.60 (t, 1H), 4.03(dd, 1H), 3.20 (dd,1H), 2.42 (t, 1H), 2.20 (m, 1H), 1.65–2.04 (m, 4H), 1.21 (m, 1H) and 0.91 (d,3H), and with 30%~40% ethyl acetate in hexanes to give cis-3-[5-(5-methyl-piperidin-2-yl)-[1,2,4]oxadiazol-3-yl]-benzonitrile (933 mg, 65.2%) $^1$H NMR (CDCl3), δ(ppm): 8.41 (s, 1H), 8.34 (d, 1H), 7.78 (dd,1H), 7.62 (t, 1H), 4.36 (t, 1H), 2.94 (dd,1H), 2.57(dd, 1H), 2.27 (m, 1H), 2.06 (m, 2H), 1.73 (m, 2H), 1.25 (m, 1H) and 0.90 (d,3H),

Example 98

Trans-2-[3-(3-chloro-phenyl)-[1,2,4]oxadiazol-5-yl]-4-methyl-piperidine and cis-2-[3-(3-chloro-phenyl)-[1,2,4]oxadiazol-5-yl]-4-methyl-piperidine 2-[3-(3-Chloro-phenyl)-[1,2,4]oxadiazol-5-yl]-4-methyl-piperidine-1-carboxylic acid tert-butyl ester (320 mg, 33.9%) was prepared according to the procedure in Example 25 from 4-methyl-piperidine-1,2-dicarboxylic acid 1-tert-butyl ester (607.5 mg, 2.5 mmol), triethylamine (1.01 g, 10 mmol) with isobutyl chloroformate (348 mg, 2.55 mmol) in THF (5 mL). After 30 minutes, 3-Chloro-N-hydroxy-benzamidine (425 mg, 2.5 mmol) in DMF (4 mL) was added and the mixture was heated to 130° C. for 4 h. The product was purified by column chromatography with 10% ethyl acetate in hexanes. Deprotection was carried out according to the procedure in Example 39 from 2-[3-(3-chloro-phenyl)-[1,2,4]oxadiazol-5-yl]-4-methyl-piperidine-1-carboxylic acid tert-butyl ester(320 mg, 0.847 mmol) with trifluoroacetic acid (1.3 ml) and dichloromethane(10 mL) for 3 h. Purification by column chromatography with 50/50 ethyl acetate/hexanes gave trans-2-[3-(3-chloro-phenyl)-[1,2,4]oxadiazol-5-yl]-4-methyl-piperidine 164.8 mg (70%); $^1$H-NMR(CDCl3) δ(ppm): 8.10 (s, 1H), 7.97 (d, 1H), 7.42 (m, 2H), 4.07 (d, 1H), 3.26 (dd, 1H), 2.80 (t, 1H), 2.17 (d, 1H), 1.99 (w, 1H), 1.69 (m, 2H), 1.24 (m, 2H) and 1.02 (d, 3H), and cis-2-[3-(3-chloro-phenyl)-[1,2,4]oxadiazol-5-yl]-4-methyl-piperidine 23.9 mg(10.2%); $^1$H-NMR(CDCl3) δ(ppm): 8.10 (s, 1H), 7.97 (d, 1H), 7.43 (m, 2H), 4.45 (t, 1H), 2.93 (m, 2H), 2.24(m, 2H), 2.68 (m, 3H), 1.29 (m, 1H) and 0.99 (d, 3H).

Example 99

3-[5-(3-methyl-piperidin-2-yl)-[1,2,4]oxadiazol-3-yl]-benzonitrile

2-[3-(3-cyano-phenyl)-[1,2,4]oxadiazol-5-yl]-3-methyl-piperidine-1-carboxylic acid tert-butyl ester (150 mg, 14.7%) was obtained as described in Example 25 from 3-methyl-piperidine-1,2-dicarboxylic acid 1-tert-butyl ester (672 mg, 2.765 mmol) with triethylamine (1.1 g, 11 mmol) in THF (8 mL) with isobutyl chloroformate (377.6 mg, 2.765 mmol). After 30 minutes, 3-chloro-N-hydroxy-benzamidine (445 mg, 2.765 mmol) in DMF (5 mL) was added and then the reaction mixture was heated to 135° C. for 3 h. The product was purified by column chromatography with 5% ethyl acetate in hexanes. 3-[5-(3-methyl-piperidin-2-yl)-[1,2,4]oxadiazol-3-yl]-benzonitrile (85 mg, 77.8%) was obtained as described in Example 25 from 2-[3-(3-Cyano-phenyl)-[1,2,4]oxadiazol-5-yl]-3-methyl-piperidine-1-carboxylic acid tert-butyl ester (150 mg, 0.407 mmol) with trifluoroacetic acid (0.5 mL) and dichloromethane (4 mL) at room temperature for 2 h.

Example 100

3-[5S-(3-Thiazol-2-ylmethyl-thiazolidin-4-yl)-[1,2,4]oxadiazol-3-yl]-benzonitrile 3-[5S-(3-Thiazol-2-ylmethyl-thiazolidin-4-yl)-[1,2,4]oxadiazol-3-yl]-benzonitrile (7.7 mg, 9%, yellow oil) was obtained as described in Example 43 from 3-(5S-thiazolidin-4-yl-[1,2,4]oxadiazol-3-yl)-benzonitrile (60 mg, 0.23 mmol) and thiazole-2-carbaldehyde (21.4 μl, 0.24 mmol) in dichloroethane (2 ml) with sodium triacetoxyborohydride (68.9 mg, 0.33 mmol) (purified on silica gel using 10% ethyl acetate in dichloromethane). $^1$H-NMR (CDCl$_3$), δ(ppm): 8.39 (bs 1H), 8.32 (d,1H), 7.78 (m, 2H), 7.61 (t, 1H), 7.37 (d, 1H), 4.90 (dd, 1H), 4.41 (d, 1H), 4.26 (d, 1H), 4.20 (dd, 2H), 3.52 (m, 2H).

Example 101

(S)-3-[5-(1-Thiazol-2-ylmethyl-pyrrolidin-2-yl)-[1,2,4]oxadiazol-3-yl]-benzonitrile 3-[5-(1-Thiazol-2-ylmethyl-pyrrolidin-2-yl)-[1,2,4]oxadiazol-3-yl]-benzonitrile (63.5 mg, 91%) was obtained as described in Example 43 from (S)-3-(5-pyrrolidin-2-yl-[1,2,4]oxadiazol-3-yl)-benzonitrile (49.8 mg, 0.18 mmol) reacted with thiazole-2-carbaldehyde (35.2 mg, 0.31 mmol) and sodium triacetoxyborohydride (72 mg, 0.34 mmol) is in dichloroethane (3 mL) at room temperature. $^1$H NMR (CDCl$_3$), δ(ppm): 8.39 (s, 1H), 8.32 (d, 1H), 7.78 (d, 1H), 7.68 (d, 1H), 7.60 (t, 1H), 7.27 (d, 1H), 4.32 (dd, 1H), 4.27 (dab, 1H), 4.17 (dab, 1H), 3.31 (m, 1H), 2.81 (q, 1H), 2.39 (m, 1H), 2.25 (m, 1H), 2.14 (m, 1H), 2.04 (m, 1H).

Example 102

(S)-3-[5-(1-Pyridin-2-ylmethyl-pyrrolidin-2-yl)-[1,2,4]oxadiazol-3-yl]-benzonitrile (S)-3-[5-(1-Pyridin-2-ylmethyl-pyrrolidin-2-yl)-[1,2,4]oxadiazol-3-yl]-benzonitrile (52.6 mg, 77%) was obtained as described in Example 43 from (S)-3-(5-pyrrolidin-2-yl-[1,2,4]oxadiazol-3-yl)-benzonitrile (49.8 mg, 0.18 mmol) reacted with pyridine-2-carbaldehyde (36.8 mg, 0.34 mmol) and sodium triacetoxyborohydride (72 mg, 0.34 mmol) in dichloroethane (3 mL) at room temperature. $^1$H NMR (CDCl$_3$), δ(ppm): 8.49 (d, 1H), 8.37 (s, 1H), 8.29 (dd, 1H), 7.77 (dd, 1H), 7.60 (m, 2H), 7.38 (d, 1H), 7.11 (m, 1H), 4.22 (dd, 1H), 4.02 (d$_{AB}$, 1H), 3.89 (d$_{AB}$, 1H), 3.21 (m, 1H), 2.70 (q, 1H), 2.38 (m, 1H), 1.9–2.23 (m, 3H).

Example 103

(S)-3-[5-(1-Pyridin-2-ylmethyl-2,5-dihydro-1H-pyrrol-2-yl)-[1,2,4]oxadiazol-3-yl]-benzonitrile (S)-3-[5-(1-Pyridin-2-ylmethyl-2,5-dihydro-1H-pyrrol-2-yl)-[1,2,4]oxadiazol-3-yl]-benzonitrile (28.1 mg, 40%) was obtained as described in Example 43 from (S)-3-[5-(2,5-dihydro-1H-pyrrol-2-yl)-[1,2,4]oxadiazol-3-yl]-benzonitrile (50 mg, 0.18 mmol) reacted with pyridine-2-carbaldehyde (34.2 mg, 0.32 mmol) and sodium triacetoxyborohydride (72 mg, 0.34 mmol) in dichloroethane (3 mL) at room temperature. $^1$H NMR (CDCl$_3$), δ(ppm): 8.49 (d, 1H), 8.35 (s, 1H), 8.28 (d, 1H), 7.76 (m, 1H), 7.60 (m, 2H), 7.41 (d, 1H), 7.12 (dd, 1H), 6.11 (m, 1H), 5.88 (m, 1H), 5.26 (m, 1H), 4.26 (d$_{AB}$, 1H), 4.10 (d, $_{AB}$, 1H), 4.02 (dm, 1H), 3.65 (dm, 1H). Note: after one week, reanalysis of $^1$H NMR indicated aromatization of the dihydropyrrole to pyrrole (10% aromatic impurity).

Example 104

Trans-3-[5-(5-methyl-1-pyridin-2-ylmethyl-piperidin-2-yl)-[1,2,4]oxadiazol-3-yl]-benzonitrile Trans-3-[5-(5-methyl-1-pyridin-2-ylmethyl-piperidin-2-yl)-[1,2,4]oxadiazol-3-yl]-benzonitrile (32.5 mg, 44%) was obtained as described in Example 43 from the trans-3-[5-(5-methyl-piperidin-2-yl)-[1,2,4]oxadiazol-3-yl]-benzonitrile (53.6 mg, 0.2 mmol) and pyridine-2-carbaldehyde (25.4 mg, 0.24 mmol) in dichloroethane (2 mL) with sodium triacetoxyborohydride (63.6 mg, 0.3 mmol). The product was purified by column chromatography with 50%~100% ethyl acetate in hexanes. $^1$H NMR (CDCl3), δ(ppm): 8.49 (d, 1H), 8.33 (s, 1H), 8.31 (d, 1H), 7.77 (dd,1H), 7.64 (m, 2H), 7.50 (dd, 1H), 7.14 (dd, 1H), 3.86 (m, 1H), 3.74 (d, 1H), 3.50 (dd,1H), 2.96 (d, 1H), 1.91 (m, 5H), 1.10 (m, 1H) and 0.88 (d,3H).

Example 105

Cis-3-[5-(5-methyl-1-pyridin-2-ylmethyl-piperidin-2-yl)-[1,2,4]oxadiazol-3-yl]-benzonitrile cis-3-[5-(5-methyl-1-pyridin-2-ylmethyl-piperidin-2-yl)-[1,2,4]oxadiazol-3-yl]-benzonitrile (64.3 mg, 89%) was obtained as described in Example 43 from cis-3-[5-(5-methyl-piperidin-2-yl)-[1,2,4]oxadiazol-3-yl]-benzonitrile (53.6 mg, 0.2 mmol) and pyridine-2-carbaldehyde (25.4 mg, 0.24 mmol) in dichloroethane (2 mL) with sodium triacetoxyborohydride (63.6 mg, 0.3 mmol). The product was purified by column chromatography with 50%~100% ethyl acetate in hexanes. $^1$H NMR (CDCl3), δ(ppm): 8.52 (d, 1H), 8.41 (s, 1H), 8.34 (d, 1H), 7.77 (dd,1H), 7.63 (m, 2H), 7.44 (d, 1H), 7.15 (dd, 1H), 4.38 (m, 1H), 3.90 (q, 2H), 2.65 (d, 2H), 2.12 (m, 2H), 1.63–1.82 (m, 2H), 1.32 (m, 1H) and 0.89 (d,3H).

Example 106

Cis-3-[5-(5-methyl-1-thiazol-2-ylmethyl-piperidin-2-yl)-11,2,4]oxadiazol-3-yl]-benzonitrile cis-3-[5-(5-methyl-1-thiazol-2-ylmethyl-piperidin-2-yl)-[1,2,4]oxadiazol-3-yl]-benzonitrile (67.5 mg, 92%) was obtained as described in Example 43 from cis-3-[5-(5-methyl-piperidin-2-yl)-[1,2,4]oxadiazol-3-yl]-benzonitrile (53.6 mg, 0.2 mmol) and (27.8 mg, 0.24 mmol) in dichloroethane (2 mL) with sodium triacetoxyborohydride (63.6 mg, 0.3 mmol). The product was purified by column chromatography with 50%~100% ethyl acetate in hexanes. $^1$H NMR (CDCl3), δ(ppm): 8.40 (s, 1H), 8.34 (d, 1H), 7.79 (d,1H), 7.70 (d, 1H), 7.60 (t, 1H), 7.29 (d, 1H), 4,45 (m, 1H), 4.18(s, 2H), 2.76 (dd, 1H), 2.68 (t,1H), 2.17 (m,2H), 1.81 (m, 2H), 1.21 (m, 1H) and 0.89 (d,3H).

Example 107

Cis-2-{2-[3-(3-chloro-phenyl)-[1,2,4]oxadiazol-5-yl]-4-methyl-piperidin-1-ylmethyl}-pyridine cis-2-{2-[3-(3-chloro-phenyl)-[1,2,4]oxadiazol-5-yl]-4-methyl-piperidin-1-ylmethy}pyridine (10.5 mg, 33%) was obtained as described in Example 43 from cis-2-[3-(3- chloro-phenyl)-[1,2,4]oxadiazol-5-yl]-4-methyl-piperidine (23.9 mg, 0.086 mmol) and pyridine-2-carbaldehyde (21.4 mg, 0.2 mmol) in dichloroethane (1 mL) with sodium triacetoxyborohydride (31.8 mg, 0.15 mmol). The product was purified by column chromatography with 3~5% acetone in hexanes. $^1$H NMR (CDCl3), δ(ppm):8.55 (d, 1H), 8.11 (d, 1H), 8.01 (d,1H), 7.64 (dt, 1H), 7.47 (m, 3H), 7.17(m, 1H), 4.45 (m, 1H), 3.91 (q, 2H), 3.08 (td, 1H), 2.73 (m,1H), 2.05 (m,1H), 1.72 (m, 3H), 1.37 (m, 1H), 0.95(d, 3H), Example 108

Cis-3-[5-(3-Methyl-1-pyridin-2-ylmethyl-piperidin-2-yl)-[1,2,4]oxadiazol-3-yl]-benzonitrile and trans-3-[5-(3-Methyl-1-pyridin-2-ylmethyl-piperidin-2-yl)-[1,2,4]oxadiazol-3-yl]-benzonitrile The reaction was carried out as described in Example 43 from 3-[5-(3-methyl-piperidin-2-yl)-[1,2,4]oxadiazol-3-yl]-benzonitrile (29 mg, 0.108 mmol) with pyridine-2-carbaldehyde (13.9 mg, 0.13 mmol) and sodium triacetoxyborohydride (34.3 mg, 0.162 mmol) in dichloroethane (2 mL) to give cis-3-[5-(3-Methyl-1-pyridin-2-ylmethyl-piperidin-2-yl)-[1,2,4]oxadiazol-3-yl]-benzonitrile (20 mg, 51.5%); $^1$H NMR (CDCl3), δ(ppm): 8.55 (d,1H), 8.45 (s, 1H), 8.38 (d, 1H), 7.80 (d,1H), 7.65 (m, 2H), 7.41 (d, 1H), 7.18(m, 1H), 4.40 (d, 1H), 3.76 (d, 1H), 3.53 (d, 1H), 3.03 (m,1H), 2.68 (m,1H), 2.30 (m, 1H), 1.74(m, 4H), 0.82 (d, 3H); and trans-3-[5-(3-methyl-1-pyridin-2-ylmethyl-piperidin-2-yl)-[1,2,4]oxadiazol-3-yl]-benzonitrile (5 mg, 12.9%); $^1$H NMR (CDCl3), δ(ppm): 8.49+ (d,1H), 8.43 (s, 1H), 8.35 (d, 1H), 7.80 (d,1H), 7.65 (m, 2H), 7.55 (d, 1H), 7.14(m, 1H), 3.59 (m, 3H), 3.03 (m, 1H), 2.25 (m, 2H), 1.92 (m,1H), 1.73 (m, 2H), 1.27(m, 1H), 0.87 (d, 3H).

Example 109

Cis-3-[5-(3-Methyl-1-thiazol-2-ylmethyl-piperidin-2-yl)-[1,2,4]oxadiazol-3-yl]-benzonitrile cis-3-[5-(3-methyl-1-thiazol-2-ylmethyl-piperidin-2-yl)-[1,2,4]oxadiazol-3-yl]-benzonitrile (25.8 mg, 70.5%) was obtained as described in Example 43 from 3-[5-(3-Methyl-piperidin-2-yl)-[1,2,4]oxadiazol-3-yl]-benzonitrile (27 mg, 0.1 mmol) with thiazole-2-carbaldehyde (13.5 mg, 0.12 mmol) and sodium triacetoxyborohydride (31.8 mg, 0.15 mmol) in dichloroethane (0.5 mL). $^1$H NMR (CDCl3), δ(ppm): 8.45 (s, 1H), 8.37 (d, 1H), 7.80 (d,1H), 7.69 (d, 1H), 7.63 (t, 1H), 7.31 (d, 1H), 3.87 (s, 2H), 3.73 (d, 1H), 3.12 (m, 1H), 2.45 (m,1H), 2.26 (m, 1H), 1.81(m, 4H), 0.94 (d, 3H).

Example 110

3-[5-(4-Thiazol-2-ylmethyl-morpholin-3-yl)-[1,2,4]oxadiazol-3-yl]-benzonitrile

3-[5-(4-Thiazol-2-ylmethyl-morpholin-3-yl)-[1,2,4]oxadiazol-3-yl]-benzonitrile (55 mg, 50%) was obtained as described in Example 43 from 3-(5-Morpholin-3-yl-[1,2,4]oxadiazol-3-yl)-benzonitrile (80 mg, 0.31 mmol) with 2-thiazolecarboxaldehyde (72 mg, 0.64 mmol) and sodium triacetoxyborohydride (159 mg, 0.75 mmol). The product was purified by SPE chromatography on silica gel using 10–25% ethyl acetate in hexanes. $^1$H NMR (CDCl$_3$), δ(ppm): 8.44 (s, 1H), 8.36 (d, 1H), 7.81 (d, 1H), 7.74 (d, 1H), 7.66 (dd, 1H), 7.35 (d, 1H), 4.31 (t, 1H), 4.15 (m, 4H), 3.88 (m, 2H), 3.30 (m, 1H), 2.73 (m, 1H).

Example 111

3-{5-[4-(4-Methyl-pyridin-2-ylmethyl)-morpholin-3-yl]-[1,2,4]oxadiazol-3-yl}-benzonitrile 3-{5-[4-(4-Methyl-pyridin-2-ylmethyl)-morpholin-3-yl]-[1,2,4]oxadiazol-3-yl}-benzonitrile (44 mg, 43%) was obtained as described in Example 43 from 3-(5-Morpholin-3-yl-[1,2,4]oxadiazol-3-yl)-benzonitrile (72 mg, 0.28 mmol) with 4-Methyl-pyridine-2-carbaldehyde (80 mg, 0.66) and sodium triacetoxyborohydride (185 mg, 0.87 mmol). The product was purified by SPE chromatography on silica gel using 10–5% ethyl acetate in hexanes. $^1$H NMR (CDCl$_3$), δ(ppm): 8.39 (m, 3H), 7.82 (d, 1H), 7.64 (dd, 1H), 7.25 (s, 1H), 7.02 (m, 1H), 4.21 (d, 1H), 4.08 (d, 2H), 3.89 (m, 3H), 3.78 (d, 1H), 3.18 (m, 1H), 2.62 (m, 1H), 2.37 (s, 3H).

Example 112

3-[3-(3-Chloro-phenyl)-[1,2,4]oxadiazol-5-yl]-4-pyridin-2-ylmethyl-morpholine

3-[3-(3-Chloro-phenyl)-[1,2,4]oxadiazol-5-yl]-4-pyridin-2-ylmethyl-morpholine was obtained as described in Example 43 from (63 mg, 59%) 3-[3-(3-Chloro-phenyl)-[1,2,4]oxadiazol-5-yl]-morpholine (80 mg, 0.30 mmol) with 2-pyridinecarboxaldehyde (65 mg, 0.60) and sodium triacetoxyborohydride (89 mg, 0.42 mmol). The product was purified by SPE chromatography on silica gel using 20–30% ethyl acetate in hexanes. $^1$H NMR (CDCl$_3$), δ(ppm): 8.55 (d, 1H), 8.13 (s, 1H), 8.02 (d, 1H), 7.68 (dd, 1H), 7.49 (m, 3H), 7.20 (dd, 1H), 4.21 (t, 1H), 4.07 (d, 2H), 3.87 (m, 4H), 3.18 (m, 1H), 2.62 (m, 1H).

Example 113

3-[3-(3-Chloro-phenyl)-[1,2,4]oxadiazol-5-yl]-4-thiazol-2-ylmethyl-morpholine

3-[3-(3-Chloro-phenyl)-[1,2,4]oxadiazol-5-yl]-4-pyridin-2-ylmethyl-morpholine was obtained as described in Example 43 from (48 mg, 44%) 3-[3-(3-Chloro-phenyl)-[1,2,4]oxadiazol-5-yl]-morpholine (80 mg, 0.30 mmol) with 2-thiazolecarboxaldehyde (68 mg, 0.60) and sodium triacetoxyborohydride (89 mg, 0.42 mmol). The product was purified by SPE chromatography on silica gel using 20–60% ethyl acetate in hexanes. $^1$H NMR (CDCl$_3$), δ(ppm): 8.13 (s, 1H), 8.01 (d, 1H), 7.75 (d, 1H), 7.47 (m, 2H), 7.33 (d, 1H), 4.29 (m, 1H), 4.15 (m, 4H), 3.88 (m, 2H), 3.30 (m, 1H), 2.70 (m, 1H).

Example 114

2-{2-[3-(3-Chloro-phenyl)-[1,2,4]oxadiazol-5-yl]-piperidin-1-ylmethyl}-pyridine

2-{2-[3-(3-chloro-phenyl)-[1,2,4]oxadiazol-5-yl]-piperidin-1-ylmethyl}-pyridine (8.6 mg, 12%) was obtained as described in Example 80 from 3-chloro-N-hydroxy-benzamidine (34 mg, 0.2 mmol), 1-pyridin-2-ylmethyl-piperidine-2-carboxylic acid methyl ester (46.8 mg, 0.2 mmol) and sodium t-butoxide (19.2 mg, 0.2 mmol) in toluene (1.5 mL) and ethanol (1 mL) at 110° C. overnight. The reaction mixture was concentrated with silica gel and purified by column chromatography with 5% acetone in hexanes. $^1$H NMR (CDCl3), δ(ppm): 8.51 (d, 1H), 8.11 (d, 1H), 7.99

(d,1H), 7.65 (m, 1H), 7.44 (m, 3H), 7.13 (m, 1H), 4.13 (m, 1H), 3.74(q, 2H), 3.04 (m, 1H), 2.44 (m,1H), 2.02 (m,2H), 1.60(m, 4H).

Example 115

2-[3-(3-Chloro-phenyl)-[1,2,4]oxadiazol-5-yl]-1-thiazol-2-ylmethyl-piperidine

2-[3-(3-Chloro-phenyl)-[1,2,4]oxadiazol-5-yl]-1-thiazol-2-ylmethyl-piperidine (8.8 mg 12.2%) was obtained as described in Example 80 from 3-chloro-N-hydroxy-benzamidine (34 mg, 0.2 mmol), 1-thiazol-2-ylmethyl-piperidine-2-carboxylic acid methyl ester (46.8 mg, 0.2 mmol) and sodium t-butoxide (19.2 mg, 0.2 mmol) in toluene (1.5 mL) and ethanol (1 mL) at 110° C. overnight. The reaction mixture was concentrated with silica gel and purified by column chromatography with 5% acetone in hexanes. $^1$H NMR (CDCl3), δ(ppm): 8.11 (s, 1H), 8.00 (d,1H), 7.70 (d, 1H), 7.44 (m, 2H), 7.29(d, 1H), 4.26 (t, 1H), 4.05(d, 2H), 3.11 (m, 1H), 2.61 (m,1H), 2.08 (m,2H), 1.62(m, 4H).

Pharmaceutical Examples

FLIPR Assay of Group I Receptor Antagonist Activity

For FLIPR analysis, cells were seeded on collagen coated clear bottom 96-well plates with black sides and analysis of $[Ca^{2+}]_i$ mobilization was performed 24 hours following seeding. Cell cultures in the 96-well plates were loaded with a 4 μM solution of acetoxymethyl ester form of the fluorescent calcium indicator fluor-3 (Molecular Probes, Eugene, Oreg.) in 0.01% pluronic. All assays were performed in a buffer containing 127 mM NaCl, 5 mM KCl, 2 mM $MgCl_2$, 0.7 mM $NaH_2PO_4$, 2 mM $CaCl_2$, 0.422 mg/ml $NaHCO_3$, 2.4 mg/ml HEPES, 1.8 mg/ml glucose and 1 mg/ml BSA Fraction IV (pH 7.4).

FLIPR experiments were done using a laser setting of 0.800 W and a 0.4 second CCD camera shutter speed with excitation and emission wavelengths of 488 nm and 562 nm, respectively. Each FLIPR experiment was initiated with 160 μL of buffer present in each well of the cell plate. A 40 μL addition from the antagonist plate was followed by a 50 μL addition from the agonist plate. After each addition the fluorescence signal was sampled 50 times at 1 second intervals followed by 3 samples at 5 second intervals. Responses were measured as the peak height of the response within the sample period. $EC_{50}/IC_{50}$ determinations were made from data obtained from 8 point concentration response curves (CRC) performed in duplicate. Agonist CRC were generated by scaling all responses to the maximal response observed for the plate. Antagonist block of the agonist challenge was normalized to the average response of the agonist challenge in 14 control wells on the same plate.

Measurement of Inositol Phosphate (IP3) Turnover in Intact Whole Cells

GHEK stably expressing the human mGluR5d receptor were seeded onto 24 well poly-L-lysine coated plates at $40 \times 10^4$ cells/well in media containing 1 μCi/well [3H] myo-inositol. Cells were incubated overnight (16 h), then washed three times and incubated for 1 hour at 37° C. in HEPES buffered saline (146 mM NaCl, 4.2 mM KCl, 0.5 mM $MgCl_2$, 0.1% glucose, 20 mM HEPES, pH 7.4) supplemented with 1 unit/ml glutamate pyruvate transaminase and 2 mM pyruvate. Cells were washed once in HEPES buffered saline and pre-incubated for 10 minutes in HEPES buffered saline containing 10 mM LiCl. Compounds (agonists) were added and incubated at 37° C. for 30 minutes. Antagonist activity was determined by pre-incubating test compounds for 15 minutes, then incubating in the presence of glutamate (80 μM) or DHPG (30 μM) for 30 minutes. The reaction was terminated by the addition of 0.5 ml perchloric acid (5%) on ice, with incubation at 4° C. for at least 30 minutes. Samples were collected in 15 ml Falcon tubes and inositol phosphates were separated using Dowex columns, as described below.

Assay For Inositol Phosphates Using Gravity-Fed Ion-Exchange Columns a) Preparation of Ion-Exchange Columns Ion-exchange resin (Dowex AG1-X8 formate form, 200–400 mesh, BIORAD) was washed three times with distilled water and stored at 4° C. 1.6 ml resin was added to each column and washed with 3 ml 2.5 mM HEPES, 0.5 mM EDTA, pH 7.4.

b) Sample Treatment

Samples were collected in 15 ml Falcon tubes and neutralized with 0.375 M HEPES, 0.75 M KOH. 4 ml of HEPES/EDTA (2.5/0.5 mM, pH 7.4) were added to precipitate the potassium perchlorate. Supernatant was added to the prepared Dowex columns.

c) Inositol Phosphate Separation

Elute glycero phosphatidyl inositols with 8 ml 30 mM ammonium formate.

Elute total inositol phosphates with 8 ml 700 mM ammonium formate/100 mM formic acid and collect eluate in scintillation vials. Count eluate mixed with 8 ml scintillant.

Results

Typical $IC_{50}$ values as measured in the assays described above are 10 μM or less. In one aspect of the invention the $IC_{50}$ is below 2 μM. In another aspect of the invention the $IC_{50}$ is below 0.2 μM. In a further aspect of the invention the $IC_{50}$ is below 0.05 μM.

The invention claimed is:

1. A compound having the formula I

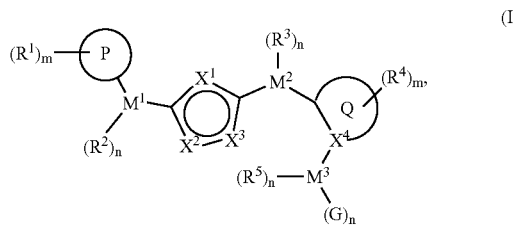

wherein:
P is a 5- or 6-membered ring containing one or more atoms independently selected from C, N, O or S, wherein said ring may be fused with a 5- or 6-membered ring containing one or more atoms independently selected from C, N, O or S;
$R^1$ is selected from the group consisting of hydrogen, hydroxy, halo, nitro, $C_{1-6}$alkylhalo, $OC_{1-6}$alkylhalo, $C_{1-6}$alkyl, $OC_{1-6}$alkyl, $C_{2-6}$alkenyl, $OC_{2-6}$alkenyl, $C_{2-6}$alkynyl, $OC_{2-6}$alkynyl, $C_{0-6}$alkyl$C_{3-6}$cycloalkyl, $OC_{0-6}$alkyl$C_{3-6}$cycloalkyl, $C_{0-6}$alkylaryl, $OC_{0-6}$alkylaryl, $(CO)R^8$, $O(CO)R^8$, $O(CO)OR^8$, $C_{1-6}$alkyl$OR^8$, $OC_{2-6}$alkyl$OR^8$, $C_{1-6}$alkyl(CO)$R^8$, $OC_{1-6}$alkyl(CO)$R^8$, $C_{0-6}$alkyl$CO_2R^8$, $OC_{1-6}$alkyl$CO_2R^8$, $C_{0-6}$alkylcyano, $OC_{2-6}$alkylcyano, $C_{0-6}$alkyl$NR^8R^9$, $OC_{2-6}$alkyl$NR^8R^9$, $C_{1-6}$alkyl(CO)$NR^8R^9$, $OC_{1-6}$alkyl(CO)$NR^8R^9$, $C_{0-6}$alkyl$NR^8$(CO)$R^9$, $OC_{2-6}$alkyl$NR^8$(CO)$R^9$, $C_{0-6}$alkyl$NR^8$(CO)$NR^8R^9$, $C_{0-6}$alkyl$SR^8$, $OC_{2-6}$alkyl$SR^8$, $C_{0-6}$alkyl(SO)$R^8$, $OC_{2-6}$alkyl(SO)$R^8$, $C_{0-6}$alkyl$SO_2R^8$, $OC_{2-6}$alkyl$SO_2R^8$, $C_{0-6}$alkyl($SO_2$)$NR^8R^9$, $OC_{2-6}$alkyl($SO_2$)$NR^8R^9$, $C_{0-6}$alkyl$NR^8$($SO_2$)$R^9$, $OC_{2-6}$alkyl$NR^8$($SO_2$)$R^9$, $C_{0-6}$alkyl$NR^8$($SO_2$)$NR^8R^9$, $OC_{2-6}$alkyl$NR^8$($SO_2$)$NR^8R^9$, (CO)$NR^8R^9$, O(CO)$NR^8R^9$, $NR^8OR^9$, $C_{0-6}$alkyl$NR^8$(CO)$OR^9$, $OC_{0-6}$ alkyl$NR^8$(CO)$OR^9$, $SO_3R^8$ and a 5- or 6-membered ring containing one or more atoms independently selected from C, N, O or S, wherein said ring may be substituted by one or more A;

$M^1$ is selected from the group consisting of a bond, $C_{1-3}$alkyl, $C_{2-3}$alkenyl, $C_{2-3}$alkynyl, $C_{0-4}$alkyl(CO)$C_{0-4}$alkyl, $C_{0-3}$alkyl$OC_{0-3}$alkyl, $C_{0-3}$alkyl(CO)$NR^8$, $C_{0-3}$alkyl(CO)$NR^8C_{1-3}$alkyl, $C_{0-4}$alkyl$NR^8R^9$, $C_{0-3}$alkyl$SC_{0-3}$alkyl, $C_{0-3}$alkyl(SO)$C_{0-3}$alkyl and $C_{0-3}$alkyl($SO_2$)$C_{0-3}$alkyl;

$R^2$ is selected from the group consisting of hydrogen, hydroxy, oxo, =$NR^8$, =$NOR^8$, $C_{1-4}$alkylhalo, halo, $C_{1-4}$alkyl, O(CO)$C_{1-4}$alkyl, $C_{1-4}$alkyl(SO)$C_{0-4}$alkyl, $C_{1-4}$alkyl($SO_2$)$C_{0-4}$alkyl, (SO)$C_{0-4}$alkyl, ($SO_2$)$C_{0-4}$alkyl, $OC_{1-4}$alkyl, $C_{0-4}$alkylcyano, $C_{1-4}$alkyl$OR^8$ and $C_{0-4}$alkyl$NR^8R^9$;

$X^1$ and $X^2$ are N;

$X^3$ is O;

$M^2$ is a bond;

$R^3$ is selected from the group consisting of hydrogen, hydroxy, oxo, =$NR^8$, =$NOR^8$, $C_{1-4}$alkylhalo, halo, $C_{1-4}$alkyl, O(CO)$C_{1-4}$alkyl, $C_{1-4}$alkyl(SO)$C_{0-4}$alkyl, $C_{1-4}$alkyl($SO_2$)$C_{0-4}$alkyl, (SO)$C_{0-4}$alkyl, ($SO_2$)$C_{0-4}$alkyl, $OC_{1-4}$alkyl, $C_{0-4}$alkylcyano, $C_{1-4}$alkyl$OR^8$ and $C_{0-4}$alkyl$NR^8R^9$;

Q is a 4, 5, or 6-membered ring containing one or more atoms independently selected from C, N, O or S, wherein said ring may be fused with a 5- or 6-membered ring containing one or more atoms independently selected from C, N, O or S;

$X^4$ is N;

$R^4$ is selected from the group consisting of hydrogen, hydroxy, oxo, =$NR^8$, =$NOR^8$, $C_{1-4}$alkylhalo, halo, $C_{1-4}$alkyl, $OC_{0-6}$alkylaryl, O(CO)$C_{1-4}$alkyl, $C_{1-4}$alkyl(SO)$C_{0-4}$alkyl, $C_{1-4}$alkyl($SO_2$)$C_{0-4}$alkyl, (SO)$C_{0-4}$alkyl, ($SO_2$)$C_{0-4}$alkyl, $OC_{1-4}$alkyl, $C_{1-4}$alkyl$OR^8$, $C_{0-4}$alkylcyano and $C_{0-4}$alkyl$NR^8R^9$;

$M^3$ is $C_{1-4}$alkyl;

$R^5$ is selected from the group consisting of hydrogen, hydroxy, oxo, =$NR^8$, =$NOR^8$, $C_{1-4}$alkylhalo, halo, $C_{1-4}$alkyl, O(CO)$C_{1-4}$alkyl, $C_{1-4}$alkyl(SO)$C_{0-4}$alkyl, $C_{1-4}$alkyl($SO_2$)$C_{0-4}$alkyl, (SO)$C_{0-4}$alkyl, ($SO_2$)$C_{0-4}$alkyl, $OC_{1-4}$alkyl, $C_{0-4}$alkylcyano, $C_{1-4}$alkyl$OR^8$ and $C_{0-4}$alkyl$NR^8R^9$;

G is a 5 or 6 membered ring containing one or more atoms selected from C, N, O or S, wherein said ring may be fused with a 5 or 6-membered ring containing one or more atoms independently selected from C, N, O or S, and wherein either of said rings may be substituted by one or more A;

$R^6$ is selected from the group consisting of hydrogen and a 5- or 6-membered ring containing one or more atoms independently selected from C, N, O or S, wherein said ring may be fused with a 5- or 6-membered ring containing one or more atoms independently selected from C, N, O or S, and wherein any of the rings may be substituted by one or more A;

$R^8$ and $R^9$ are independently selected from hydrogen, $C_{1-6}$alkyl, $C_{0-6}$alkyl$C_{3-6}$cycloalkyl, $C_{0-6}$alkylaryl, $C_{0-6}$alkylheteroaryl and a 5- or 6-membered ring containing one or more atoms independently selected from C, N, O or S;

wherein any $C_{1-6}$alkyl, $C_{2-6}$alkenyl, $C_{2-6}$alkynyl, $C_{0-6}$alkyl$C_{3-6}$cycloalkyl, $C_{0-6}$alkylaryl, $C_{0-6}$alkylheteroary and 5- or 6-membered ring containing one or more atoms independently selected from C, N, O or S as defined under $R^1$, $R^2$, $R^3$, $R^4$, $R^5$, $R^6$, $R^8$, and $R^9$ may be substituted by one or more A;

A is selected from the group consisting of hydrogen, hydroxy, oxo, halo, nitro, $C_{1-6}$alkyl, $C_{0-6}$alkyl$C_{3-6}$cycloalkyl, $C_{1-6}$alkylhalo, $OC_{1-6}$alkylhalo, $C_{2-6}$alkenyl, $OC_{1-6}$alkyl, $C_{0-3}$alkylaryl, $C_{1-6}$alkyl$OR^8$, $OC_{2-6}$alkyl$OR^8$, $C_{1-6}$alkyl$SR^8$, $OC_{2-6}$alkyl$SR^8$, (CO)$R^8$, O(CO)$R^8$, $OC_{2-6}$alkylcyano, $C_{0-6}$alkylcyano, $C_{0-6}$alkyl$CO_2R^8$, $OC_{1-6}$alkyl$CO_2R^8$, O(CO)$OR^8$, $OC_{1-6}$ alkyl(CO)$R^8$, $C_{1-6}$alkyl(CO)$R^8$, $NR^8OR^9$, $C_{0-6}$alkyl$NR^8R^9$, $OC_{2-6}$alkyl$NR^8R^9$, $C_{0-6}$alkyl(CO)$NR^8R^9$, $OC_{1-6}$alkyl(CO)$NR^8R^9$, $OC_{2-6}$alkyl$NR^8$(CO)$R^9$, $C_{0-6}$alkyl$NR^8$(CO)$R^9$, $C_{0-6}$alkyl$NR^8$(CO)$NR^8R^9$, O(CO)$NR^8R^9$, $NR^8$(CO)$OR^9$, $C_{0-6}$alkyl($SO_2$)$NR^8R^9$, $OC_{2-6}$alkyl($SO_2$)$NR^8R^9$, $C_{0-6}$alkyl$NR^8$($SO_2$)$R^9$, $OC_{2-6}$alkyl$NR^8$($SO_2$)$R^9$, $SO_3R^8$, $C_{1-6}$alkyl$NR^8$($SO_2$)$NR^8R^9$, $OC_{2-6}$alkyl($SO_2$)$R^8$, $C_{0-6}$alkyl($SO_2$)$R^8$, $C^{0-6}$alkyl(SO)$R^8$ and $OC_{2-6}$alkyl(SO)$R^8$;

m is selected from 0, 1, 2, 3 or 4; and n is selected from 0, 1, 2 or 3;

or salt thereof, with the proviso that the compound is not 1,2,4-oxadiazole 3-(2,3-dimethoxyphenyl)-5-[1-(phenylmethyl)-2-pyrrolidinyl]- or Piperidine, 2-[3-(2,3-dimethoxyphenyl)-1,2,4-oxadiazol-5-yl]-1-(phenylmethyl)-.

2. A pharmaceutical formulation comprising as an active ingredient a therapeutically effective amount of a compound according to claim 1 in association with one or more pharmaceutically acceptable diluents, excipients and/or inert carriers.

3. The pharmaceutical formulation according to claim 2, for use in the prevention and/or treatment of mGluR5 receptor-mediated disorders.

4. A compound according to claim 1, for use in therapy.

5. The compound according to claim 4, for use in prevention and/or treatment of mGluR5 receptor-mediated disorders.

6. A method of treatment of mGluR5 receptor-mediated disorders selected from the group consisting of stroke, head trauma, anoxic injuries, ischemic injuries, hypoglycemia, epilepsy, neurodegenerative disorders, Alzheimer's disease and pain, comprising administering to a mammal in need of such treatment, a therapeutically effective amount of a compound according to claim 1.

7. The method according to claim 6, wherein said mammal is a human.

8. The method according to claim 6, wherein said mGluR5 receptor-mediated disorders are psychiatric disorders.

9. The method according to claim 6, wherein said mGluR5 receptor-mediated disorders are neurological disorders.

10. The method according to claim 6, wherein said mGluR5 receptor-mediated disorders are chronic and acute pain disorders.

11. A compound according to claim 1 selected from the group consisting of: 3-[5-(1-Pyridin-2-ylmethyl-piperidin-2-yl)-[1,2,4]oxadiazol-3-yl]-benzonitrile, 3-[3-(1-Pyridin-2-ylmethyl-piperidin-2-yl)-[1,2,4]oxadiazol-5-yl]-benzonitrile, 3-[5-(1-Thiazol-2-ylmethyl-piperidin-2-yl)-[1,2,4] oxadiazol-3-yl]-benzonitrile, 3-{5-[1-(1-Methyl-1H-imidazol-2-ylmethyl)-piperidin-2yl]-[1,2,4]oxadiazol-3-yl}-benzonitrile, 3-{5-[1-(6-Methyl-pyridin-2-ylmethyl)-piperidin-2-yl]-[1,2,4]oxadiazol-3-yl}-benzonitrile, 3-[3-(1-Thiazol-2-ylmethyl-piperidin-2-yl)-[1,2,4]oxadiazol-5-yl]-benzonitrile, 3-[5-(1-Thiazol-2-ylmethyl-pyrrolidin-2-yl)-[1,2,4]oxadiazol-3-yl]-benzonitrile, 3-{5-[1-(5-Chloro-pyridin-2-ylmethyl)-piperidin-2-yl]-[1,2,4]oxadiazol-3-yl}-benzonitrile, 2-[2-(5-m-Tolyl-[1,2,4]oxadiazol-3-yl)-piperidin-1-ylmethyl]-pyridine, 3-{5-[1-(5-Fluoro-pyridin-2-ylmethyl)-piperidin-2-yl]-[1,2,4]oxadiazol-3-yl}-benzonitrile, 3-[5S-(3-Pyridin-2-ylmethyl-thiazolidin-4-yl)-[1,2,4]oxadiazol-3-yl]-benzonitrile, 3-{5-[1-(3-Methyl-pyridin-2-ylmethyl)-piperidin-2-yl]-[1,2,4]oxadiazol-3-yl}-benzonitrile, 3-{5-[1-(4-Methyl-pyridin-2-ylmethyl)-piperidin-2-yl]-[1,2,4]oxadiazol-3-yl}-benzonitrile, 3-{5-[1-(5-Methyl-pyridin-2-ylmethyl)-piperidin-2-yl]-[1,2,4]oxadiazol-3-yl}-benzonitrile, 3-{5-[1-(1-Methyl-1H-benzoimidazol-2-ylmethyl)-piperidin-2-yl]-[1,2,4]oxadiazol-3-yl}-benzonitrile, 3-[5-(6-Methyl-1-pyridin-2-ylmethyl-piperidin-2-yl)-[1,2,4]oxadiazol-3-yl]-benzonitrile, 3-[5-(4,4-Difluoro-1-pyridin-2-ylmethyl-piperidin-2-yl)-[1,2,4]oxadiazol-3-yl]-benzonitrile, 3-[5-(4,4-Difluoro-1-thiazol-2-ylmethyl-piperidin-2-yl)-[1,2,4]oxadiazol-3-yl]-benzonitrile, 3-[5-(1-Quinolin-2-ylmethyl-piperidin-2-yl)-[1,2,4]oxadiazol-3-yl]-benzonitrile, 3-{5-[1-(1H-Benzimidazole-2-ylmethyl)-piperidin-2-yl]-[1,2,4]oxadiazol-3-yl}-benzonitrile, 3-{5-[1-(2-Methyl-thiazol-4-ylmethyl)-piperidin-2-yl]-[1,2,4]oxadiazol-3-yl}-benzonitrile, 3-{5-[1-(1-Benzyl-1H-imidazol-2-ylmethyl)-piperidin-2-yl]-[1,2,4]oxadiazol-3-yl}-benzonitrile, 3-[5-(4-Pyridine-2-ylmethyl-morpholin-3-yl)-[1,2,4]oxadiazol-3-yl)-benzonitrile, 3-{5-[1-(6-Bromo-pyridin-2-ylmethyl)-piperidin-2-yl]-[1,2,4]oxadiazol-3-yl}-benzonitrile, 3-{5-[1-(4-Methoxy-3,5-dimethyl-pyridin-2-ylmethyl)-piperidin-2-yl]-[1,2,4]oxadiazol-3-yl}-benzonitrile, 3-{5-[-(6-Chloro-pyridin-2-ylmethyl)-piperidin-2-yl]-[1,2,4]oxadiazol-3-yl}-benzonitrile, 3-[5-(1-Pyrazin-2-ylmethyl-piperidin-2-yl)-[1,2,4]oxadiazol-3-yl]-benzonitrile, 3-[5-(1-Pyrimidin-4-ylmethyl-piperidin-2-yl)-[1,2,4]oxadiazol-3-yl]-benzonitrile, 5 3-{5-[1-(5-Methyl-[1,2,4]oxadiazol-3-ylmethyl)-piperidin-2-yl]-[1,2,4]oxadiazol-3-yl}-benzonitrile, 3-{5-[1-(4-Chloro-pyridin-2-ylmethyl)-piperidin-2-yl]-[1,2,4]oxadiazol-3-yl}-benzonitrile, 2-{2-[3-(3-Cyano-phenyl)-[1,2,4]oxadiazol-5-yl]-piperidin-1-ylmethyl}-thiazole-4-carbonitrile, 3-[5-(1-Benzothiazol-2-ylmethyl-piperidin-2-yl)-[1,2,4]oxadiazol-3-yl]benzonitrile, 6-{2-[3-(3-Cyano-phenyl)-[1,2,4]oxadiazol-5-yl]-piperidin-1-ylmethyl}-nicotinonitrile 3-{5-[1-(5-Methyl-isoxazol-3-ylmethyl)-piperidin-2-yl]-[1,2,4]oxadiazol-3-yl}-benzonitrile, 3-Methoxy-5-[3-(1-pyridin-2-ylmethyl-piperidin-2-yl)-[1,2,4]oxadiazol-5-yl]-benzonitrile, 2-{2-[5-(3-Methoxy-phenyl)-[1,2,4]oxadiazol-3-yl]-piperidin-1-ylmethyl}-pyridine, 3-[5-(1-Pyridin-2-ylmethyl-pyrrolidin-2-yl)-[1,2,4]oxadiazol-3-yl]-benzonitrile, 2-{2-[3-(3-Methoxy-phenyl)-[1,2,4]oxadiazol-5-yl]-piperidin-1-ylmethyl}-pyridine, (RS)-2-[2-(3-Thiophen-2-yl-[1,2,4]oxadiazol-5-yl)-piperidin-1-ylmethyl]-pyridine, 2-[2-(3-Phenyl-[1,2,4]oxadiazol-5-yl)-piperidin-1-ylmethyl]-pyridine, 2-[2-(3-m-Tolyl-[1,2,4]oxadiazol-5-yl)-piperidin-1-ylmethyl]-pyridine, (RS)-2-[2-(3-m-Tolyl-[1,2,4]oxadiazol-5-yl)-piperidin-1-ylmethyl]-pyridine, (RS)-2-{2-[3-(3-Fluoro-5-imidazol-1-yl-phenyl)-[1,2,4]oxadiazol-5-yl]-piperidin-1-methyl}-pyridine and 2-{2-[3-(3-Ethyl-phenyl)-[1,2,4]oxadiazol-5-yl]-piperidin-1-ylmethyl}-pyridine, and a salt thereof.

12. A compound according to claim 1 selected from the group consisting of: (R)- and (S)-3-[5-(1-Pyridin-2-ylmethyl-piperidin-2-yl)-[1,2,4]oxadiazol-3-yl]-benzonitrile; (S)-3-[5-(1-Thiazol-2-ylmethyl-piperidin-2-yl)-[1,2,4]oxadiazol-3-yl]-benzonitrile; 3-[5S-(3-Thiazol-2-ylmethyl-thiazolidin-4-yl)-[1,2,4]oxadiazol-3-yl]-benzonitrile; (S)-3-[5-(1-Thiazol-2-ylmethyl-pyrrolidin-2-yl)-[1,2,4]oxadiazol-3-yl]-benzonitrile; (S)-3-[5-(1-Pyridin-2-ylmethyl-pyrrolidin-2-yl)-[1,2,4]oxadiazol-3-yl]-benzonitrile; (S)-3-[5-(1-Pyridin-2-ylmethyl-2,5-dihydro-1H-pyrrol-2-yl)-[1,2,4]oxadiazol-3-yl]-benzonitrile; Trans-3-[5-(5-methyl-1-pyridin-2-ylmethyl-piperidin-2-yl)-[1,2,4]oxadiazol-3-yl]-benzonitrile; Cis-3-[5-(5-methyl-1-pyridin-2-ylmethyl-piperidin-2-yl)-[1,2,4]oxadiazol-3-yl]-benzonitrile; Cis-3-[5-(5-methyl-1-thiazol-2-ylmethyl-piperidin-2-yl)-[1,2,4]oxadiazol-3-yl]-benzonitrile; Cis-2-{2-[3-(3-chloro-phenyl)-[1,2,4]oxadiazol-5-yl]-4-methyl-piperidin-1-ylmethyl}-pyridine; Cis-3-[5-(3-Methyl-1-pyridin-2-ylmethyl-piperidin-2-yl)-[1,2,4]oxadiazol-3-yl]-benzonitrile; Trans-3-[5-(3-Methyl-1-pyridin-2-ylmethyl-piperidin-2-yl)-[1,2,4]oxadiazol-3-yl]-benzonitrile; Cis-3-[5-(3-Methyl-1-thiazol-2-ylmethyl-piperidin-2-yl)-[1,2,4]oxadiazol-3-yl]-benzonitrile; 3-[5-(4-Thiazol-2-ylmethyl-morpholin-3-yl)-[1,2,4]oxadiazol-3-yl]-benzonitrile; 3-{5-[4-(4-Methyl-pyridin-2-ylmethyl)-morpholin-3-yl]-[1,2,4]oxadiazol-3-yl}-benzonitrile; 3-[3-(3-Chloro-phenyl)-[1,2,4]oxadiazol-5-yl]-4-pyridin-2-ylmethyl-morpholine;

3-[3-(3-Chloro-phenyl)-[1,2,4]oxadiazol-5-yl]-4-thiazol-2-ylmethyl-morpholine; 2-{2-[3-(3-Chloro-phenyl)-[1,2,4]oxadiazol-5-yl]-piperidin-1-ylmethyl}-pyridine; and 2-[3-(3-Chloro-phenyl)-[1,2,4]oxadiazol-5-yl]-1-thiazol-2-ylmethyl-piperidine; and a salt thereof.

\* \* \* \* \*

UNITED STATES PATENT AND TRADEMARK OFFICE
CERTIFICATE OF CORRECTION

PATENT NO. : 7,074,809 B2 Page 1 of 1
APPLICATION NO. : 10/636977
DATED : July 11, 2006
INVENTOR(S) : David Wensbo et al.

It is certified that error appears in the above-identified patent and that said Letters Patent is hereby corrected as shown below:

Title page, item (73) Assignees: AstraZeneca AB, Sodertaljeje̶j̶l̶e̶ (SE);

Signed and Sealed this

Seventeenth Day of October, 2006

JON W. DUDAS
*Director of the United States Patent and Trademark Office*